Figure 1:
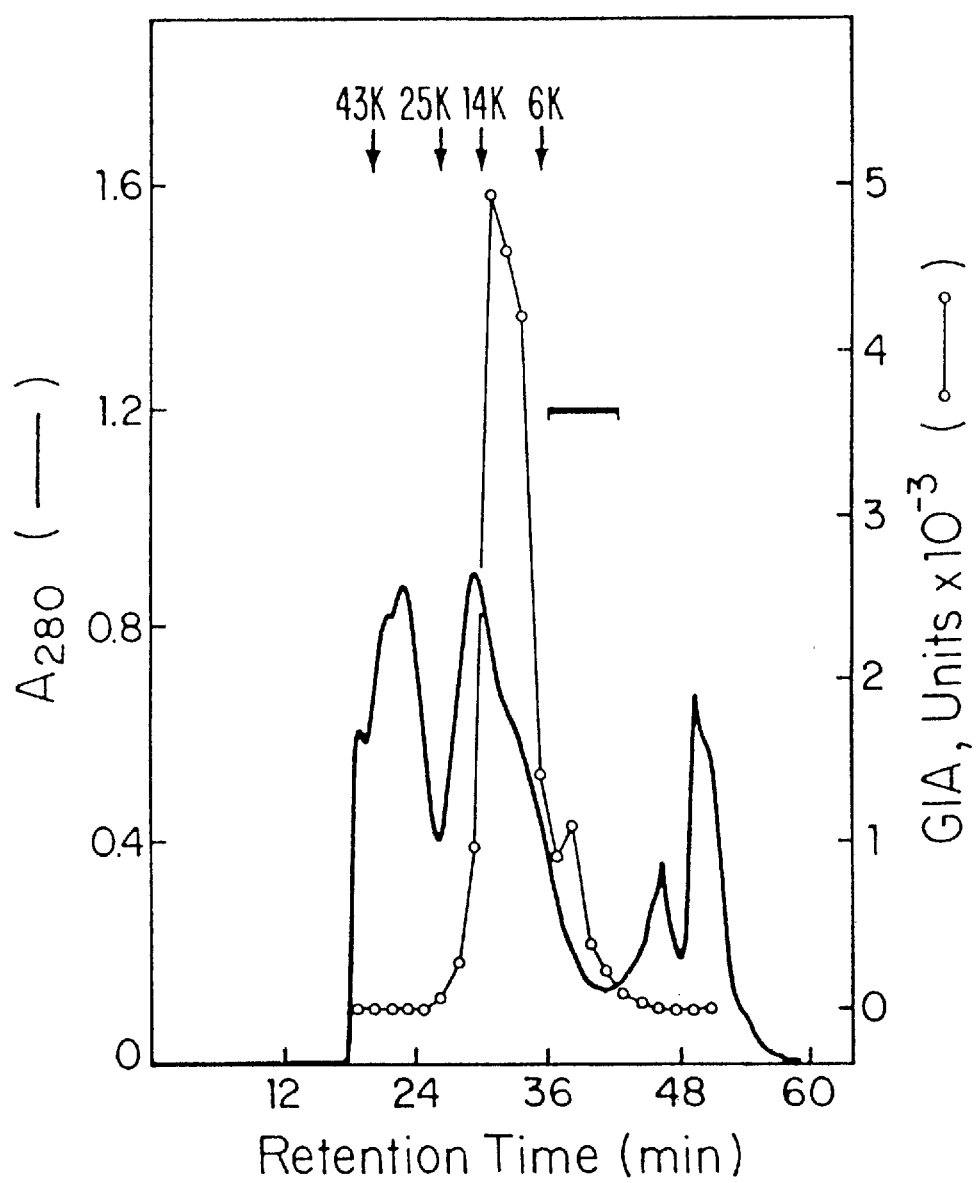

United States Patent [19]

Shoyab et al.

[11] Patent Number: 5,885,961
[45] Date of Patent: Mar. 23, 1999

[54] METHODS OF USING EPITHELINS TO MODULATE CELL PROLIFERATION

[75] Inventors: Mohammed Shoyab; Gregory D. Plowman, both of Seattle, Wash.

[73] Assignee: Bristol-Myers Squibb Company, New York, N.Y.

[21] Appl. No.: 429,998

[22] Filed: Apr. 27, 1995

Related U.S. Application Data

[60] Division of Ser. No. 668,648, Mar. 13, 1991, Pat. No. 5,416,192, which is a continuation-in-part of Ser. No. 504,508, Apr. 3, 1990, abandoned.

[51] Int. Cl.⁶ ................................................... A61K 38/18
[52] U.S. Cl. ............................................ 514/12; 530/399
[58] Field of Search ................................ 514/12; 530/324

*Primary Examiner*—John Ulm
*Assistant Examiner*—Karen E. Brown
*Attorney, Agent, or Firm*—Brian W. Poor

[57] ABSTRACT

A novel family of growth regulatory proteins termed "epithelins" are described. The epithelins comprise several distinct members sharing significant structural homology. Two members of the epithelin family, epithelin 1 and epithelin 2, have been purified from natural sources. In addition, cDNA and PCR clones encoding mature and precursor epithelins from various chordate sources have been obtained and sequenced, including the complete human, mouse and rat epithelin precursors. The recombinant expression of rat epithelin precursor and mature forms is described. Purified epithelin 1 s a bifunctional growth regulator, capable of stimulating the growth of some cell types while inhibiting the growth of others. Purified epithelin 2 is functionally similar to epithelin 1 with respect to growth inhibitory bioactivity. In contrast, however, epithelin 2 is apparently not capable of eliciting the growth stimulatory activity characteristic of epithelin 1 and, in fact, antagonizes this epithelin 1 activity.

15 Claims, 33 Drawing Sheets

Figure 18

```
M  W  I  L  V  S  W  L  A  L  V  A  R  L  V  A  G  T  Q  C
ATGTGGATCCTGGTGAGCTGGCTGGCCTTAGTGGCAAGGCTGGTGGCTGGAACACAGTGC      90

P  D  G  Q  F  C  P  V  A  C  C  L  D  Q  G  G  A  N  Y  S
CCAGATGGTCAATTCTGCCCTGTTGCCTGCTGCCTTGACCAGGGAGGAGCCAACTACAGC     150

C  C  N  P  L  L  D  T  W  P  I  I  T  S  R  R  L  D  G  S
TGCTGTAACCCTCTTCTGGACACATGGCCTATAATAACGAGCCGTCGTCTAGATGGCTCC    210

C  Q  I  R  D  H  C  P  D  G  Y  S  C  L  L  T  V  S  G  T
TGCCAGATCCGTGACCACTGTCCTGATGGCTACTCTTGTCTTCTCACTGTGTCTGGGACT    270

S  S  C  C  P  F  S  E  G  V  S  C  D  D  G  Q  H  C  C  P
TCCAGCTGCTGCCCGTTCTCTGAGGGTGTATCTTGTGATGATGGCCAGCACTGCTGCCCC    330

R  G  F  H  C  S  A  D  G  K  S  C  S  Q  I  S  D  S  L  L
CGGGGCTTCCACTGTAGTGCGGATGGGAAATCCTGCTCTCAGATATCAGATAGCCTCTTG    390

G  A  V  Q  C  P  G  S  Q  F  E  C  P  D  S  A  T  C  C  I
GGTGCTGTCCAGTGTCCTGGTAGCCAGTTCGAATGTCCTGACTCCGCCACCTGCTGTATT    450

M  I  D  G  S  W  G  C  C  P  M  P  Q  A  S  C  C  E  D  R
ATGATTGATGGTTCCTGGGGGTGCTGCCCCATGCCCCAGGCCTCTTGCTGTGAAGACAGA    510

V  H  C  C  P  H  G  A  S  C  D  L  V  H  T  R  C  I  S  P
GTGCATTGCTGTCCCCACGGGGCCTCCTGTGACCTGGTTCACACGCGATGCATTTCACCC    570

T  G  T  H  P  L  L  K  K  F  P  A  Q  R  T  N  R  A  V  A
ACGGGCACCCACCCCTTACTAAAGAAATTCCCCGCACAAAGGACCAACAGGGCAGTGGCT    630

F  P  F  S  V  V  C  P  D  A  K  T  Q  C  P  D  D  S  T  C
TTCCCTTTTTCCGTGGTGTGCCCTGATGCTAAGACCCAGTGCCCTGATGACTCTACCTGC    690

C  E  L  P  T  G  K  Y  G  C  C  P  M  P  N  A  I  C  C  S
TGTGAGCTACCCACTGGGAAGTATGGCTGTTGTCCAATGCCCAACGCCATCTGCTGTTCC    750

D  H  L  H  C  C  P  Q  D  T  V  C  D  L  I  Q  S  K  C  I
GACCACCTGCACTGCTGCCCCAGGACACTGTATGTGACCTGATCCAGAGCAAGTGCATA    810

S  K  D  Y  T  T  D  L  M  T  K  L  P  G  Y  P  V  N  E  V
TCCAAGGACTACACCACAGATCTCATGACCAAGCTGCCTGGATACCCAGTGAATGAGGTG    870

K  C  D  L  E  V  S  C  P  D  G  Y  T  C  C  R  L  N  T  G
AAGTGCGACTTGGAGGTGAGCTGTCCTGATGGCTACACCTGCTGCCGCCTCAACACTGGG    930

A  W  G  C  C  P  F  T  K  A  V  C  C  E  D  H  I  H  C  C
GCCTGGGGCTGCTGTCCATTCACCAAGGCTGTGTGTTGTGAAGACCACATTCACTGCTGC    990

P  A  G  F  Q  C  H  T  E  T  G  T  C  E  L  G  V  L  Q  V
CCAGCCGGGTTTCAGTGTCACACAGAGACAGGAACCTGTGAACTGGGAGTCCTTCAGGTA   1050

P  W  M  K  K  V  T  A  S  L  S  L  P  D  P  Q  I  L  K  N
CCCTGGATGAAAAAGGTCACGGCCTCCCTCAGCCTGCCAGACCCACAGATCTTGAAGAAT   1110
```

Figure 18 (cont.)

```
D   V   P   C   D   D   F   S   S   C   P   S   N   N   T   C   C   R   L   S
GATGTCCCCTGTGATGACTTCAGTAGCTGTCCTTCTAACAATACCTGCTGCAGACTCAGT              1170

S   G   D   W   G   C   C   P   I   P   E   A   V   C   C   L   D   H   Q   H
TCTGGGGACTGGGGCTGCTGTCCCATCCCAGAGGCTGTCTGCTGCTTAGACCACCAGCAT              1230

C   C   P   Q   G   F   K   C   M   D   E   G   Y   C   Q   K   G   D   R   M
TGCTGCCCTCAGGGTTTCAAATGTATGGATGAGGGGTACTGTCAGAAGGGAGACAGAATG              1290

V   A   G   L   E   K   M   P   V   R   Q   T   T   L   L   Q   H   G   D   I
GTGGCTGGCCTGGAGAAGATGCCTGTCCGCCAGACAACTCTGCTCCAACATGGAGATATT              1350

G   C   D   Q   H   T   S   C   P   V   G   Q   T   C   C   P   S   L   K   G
GGTTGTGACCAGCATACCAGCTGCCCAGTAGGGCAAACATGCTGCCCAAGCCTGAAGGGA              1410

S   W   A   C   C   Q   L   P   H   A   V   C   C   E   D   R   Q   H   C   C
AGTTGGGCCTGCTGCCAGTTGCCCCATGCTGTGTGCTGTGAGGACCGGCAGCACTGTTGC              1470

P   A   G   Y   T   C   N   V   K   A   R   T   C   E   K   D   A   G   S   V
CCGGCTGGGTACACCTGCAACGTGAAGGCGAGAACCTGTGAGAAGGATGCAGGCTCTGTC              1530

Q   P   S   M   D   L   T   F   G   S   K   V   G   N   V   E   C   G   A   G
CAGCCTTCCATGGACCTGACCTTTGGCTCTAAGGTTGGGAATGTGGAATGTGGTGCCGGA              1590

H   F   C   H   D   N   Q   S   C   C   K   D   S   Q   G   G   W   A   C   C
CATTTCTGCCATGATAACCAGTCCTGTTGTAAAGACAGCCAAGGAGGCTGGGCCTGCTGT              1650

P   Y   V   K   G   V   C   C   R   D   G   R   H   C   C   P   I   G   F   H
CCCTATGTAAAGGGTGTCTGCTGTAGAGATGGACGTCACTGTTGTCCCATTGGCTTCCAC              1710

C   S   A   K   G   T   K   C   L   R   K   K   T   P   R   W   D   I   L   L
TGTTCAGCCAAGGGAACCAAGTGTTTGCGGAAGAAGACCCCTCGCTGGGACATACTTTTG              1770

R   D   P   A   P   R   P   L   L
AGGGATCCAGCCCCAAGACCGCTACTG                                                1797
```

Figure 21A

| | | |
|---|---|---|
| Human | ..T....V..T.G.....R.................P...S....R....K..TTL..H.G .P | 60 |
| Rat | MWILVSWLALVARLVAGTQCPDGQFCPVACCLDQGGANYSCCNPLLDTWPIITSRRLD GS | 60 |
| Mouse | ..V.M....FA.G........................R...HH.. .. | 60 |
| Human | ..VDA..SA.H..IF...........P.A.A.G..H..............R..F. RSGNNS | 120 |
| Rat | CQIRDHCPDGYSCLLTVSGTSSCCPFSEGVSCDDGQHCCPRGFHCSADGKSCSQ -ISDSL | 119 |
| Mouse | ..THG...A...................K....G...Y....Q..........F. -M..NP | 119 |
| Human | V.. I...D.......FS...V.V....................F........T | 180 |
| Rat | LGA VQCPGSQFECPDSATCCIMIDGSWGCCPMPQASCCEDRVHCCPHGASCDLVHTRCIS | 179 |
| Mouse | ... .....................V...........................V. | 179 |
| Human | .......A..L..........LSS. .M....RSR...G........S..... ......T.. | 240 |
| Rat | PTGTHPLLKKFPAQRTNRAVAFPFS VVCPDAKTQCPDDSTCCELPTGKYGCCPMPNAICC | 239 |
| Mouse | .....T........K.....SL... ................................. | 239 |
| Human | ....................L. .ENA....L....AHT.GD ....M..........Q | 300 |
| Rat | SDHLHCCPQDTVCDLIQSKCIS KDY-TTDLMTKLPGYPVNE VKCDLEVSCPDGYTCCRLN | 298 |
| Mouse | ....................L. .N.-....L........K. ....M.....E........ | 298 |
| Human | S.........Q.............T.D.QK....Q .PH.....E.AP.H........A. | 360 |
| Rat | TGAWGCCPFTKAVCCEDHIHCCPAGFQCHTETGTCEL GVLQVPWMKKVTASLSLPDPQIL | 358 |
| Mouse | ................A............K....M .I..........I.PRR....... | 358 |
| Human | .R. ....NV.....SD...Q.T..E.............S↓.........YT.VA..Q..R .S | 420 |
| Rat | KND VPCDDFSSCPSNNTCCRLSSGDWGCCPIPEAVCCLDHQHCCPQGFKCMDEGYCQK GD | 418 |
| Mouse | .S. T.....TR..T......K.N..............S.N.........T.LAQ..... .. | 418 |
| Human | EI........A.RAS.SHPR. .....................G...............↓... | 480 |
| Rat | RMVAGLEKMPVRQTTLLQHGD IGCDQHTSCPVGQTCCPSLKGSWACCQLPHAVCCEDRQH | 478 |
| Mouse | T.......I.A....P..I.. ............................................ | 478 |
| Human | ..............S... EVV.A..ATF.ARSPH..VKD ....E........T...R.NRQ. | 540 |
| Rat | CCPAGYTCNVKARTCEK DAGSVQPSMDLTFGSKVG--N VECGAGHFCHDNQSCCKDSQGG | 536 |
| Mouse | .................. .VDFI..PVL..L.P...--. ....E........T....A.V | 536 |
| Human | ......RQ....A.R.....A..R.A.R...... REA....AP.....L.Q.. | 593 |
| Rat | WACCPYVKGVCCRDGRHCCPIGFHCSAKGTKCLR KKTPRWDILLRDPAPRPLL | 589 |
| Mouse | ......L.............G......R....... ..I....MF....V..... | 589 |

Figure 21B

```
Rat 1    GSC-QIRDHCPDGYSCLLTVSGTSSCCPFSEGVSCDDGQHCCPRGFHCSADGKSCSQ
Rat 2    VQCPGSQFECPDSATCCIMIDGSWGCCPMPQASCCEDRVHCCPHGASCDLVHTRCIS
Rat 3    VVCPDAKTQCPDDSTCCELPTGKYGCCPMPNAICCSDHLHCCPQDTVCDLIQSKCIS
Rat 4    VKC-DLEVSCPDGYTCCRLNTGAWGCCPFTKAVCCEDHIHCCPAGFQCHTETGTCEL
Rat 5    VPC-DDFSSCPSNNTCCRLSSGDWGCCPIPEAVCCLDHQHCCPQGFKCMDEG-YCQK
Rat 6    IGC-DQHTSCPVGQTCCPSLKGSWACCQLPHAVCCEDRQHCCPAGYTCNVKARTCEK
Rat 7    VEC-GAGHFCHDNQSCCKDSQGGWACCPYVKGVCCRDGRHCCPIGFHCSAKGTKCLR

Mouse 1  GSC-QTHGHCPAGYSCLLTVSGTSSCCPFSKGVSCGDGYHCCPQGFHCSADGKSCFQ
Mouse 2  VQCPGSQFECPDSATCCIMVDGSWGCCPMPQASCCEDRVHCCPHGASCDLVHTRCVS
Mouse 3  VVCPDAKTQCPDDSTCCELPTGKYGCCPMPNAICCSDHLHCCPQDTVCDLIQSKCLS
Mouse 4  VKC-DMEVSCPEGYTCCRLNTGAWGCCPFAKAVCCEDHIHCCPAGFQCHTEKGTCEM
Mouse 5  TPC-DDFTRCPTNNTCCKLNSGDWGCCPIPEAVCCSDNQHCCPQGFTCLAQG-YCQK
Mouse 6  IGC-DQHTSCPVGQTCCPSLKGSWACCQLPHAVCCEDRQHCCPAGYTCNVKARTCEK
Mouse 7  VEC-GEGHFCHDNQTCCKDSAGVWACCPYLKGVCCRDGRHCCPGGFHCSARGTKCLR Human 1  GPC-QVDAHCSAGHSCIFTVSGTSSCCPFPEAVACGDGHHCCPRGFHCSADGRSCFQ
Human 2  IQCPDSQFECPDFSTCCVMVDGSWGCCPMPQASCCEDRVHCCPHGAFCDLVHTRCIT
Human 3  VMCPDARSRCPDGSTCCELPSGKYGCCPMPNATCCSDHLHCCPQDTVCDLIQSKCLS
Human 4  VKC-DMEVSCPDGYTCCRLQSGAWGCCPFTQAVCCEDHIHCCPAGFTCDTQKGTCEQ
Human 5  VPC-DNVSSCPSSDTCCQLTSGEWGCCPIPEAVCCSDHQHCCPQGYTCVAEG-QCQR
Human 6  IGC-DQHTSCPVGQTCCPSLGGSWACCQLPHAVCCEDRQHCCPAGYTCNVKARSCEK
Human 7  VEC-GEGHFCHDNQTCCRDNRQGWACCPYRQGVCCADRRHCCPAGFRCAARGTKCLR
```

Figure 21C $$vxCx_{5-6}Cx_5CCx_8CCx_6CCxDx_2HCCPx_4Cx_{5-6}Cx_2$$

Figure 21D

| | | |
|---|---|---|
| Tomato Protease | TEC-DEYSQCAVGTTCCCILQFRRSCFSWGCCP |
| Epithelin 1 | VKC-DLEVSCPDGYTCC----RLNTGAWGCCP |
| Epithelin 2 | VVCPDAKTQCPDDSTCC----ELPTGKYGCCP |

| | | |
|---|---|---|
| Tomato Protease | LEGATCCEDHYSCCPHDYPICNVRQGTCSM |
| Epithelin 1 | FTKAVCCEDHIHCCPAGF-QCHTETGTCEL |
| Epithelin 2 | MPNAICCSDHLHCCPQDT-VCDLIQSKCIS |

Figure 22

```
M  W  T  L  V  S  W  V  A  L  T  A  G  L  V  A  G  T  R  C
ATGTGGACCCTGGTGAGCTGGGTGGCCTTAACAGCAGGGCTGGTGGCTGGAACGCGGTGC        100

P  D  G  Q  F  C  P  V  A  C  C  L  D  P  G  G  A  S  Y  S
CCAGATGGTCAGTTCTGCCCTGTGGCCTGCTGCCTGGACCCCGGAGGAGCCAGCTACAGC        160

C  C  R  P  L  L  D  K  W  P  T  T  L  S  R  H  L  G  G  P
TGCTGCCGTCCCCTTCTGGACAAATGGCCCACAACACTGAGCAGGCATCTGGGTGGCCCC       220

C  Q  V  D  A  H  C  S  A  G  H  S  C  I  F  T  V  S  G  T
TGCCAGGTTGATGCCCACTGCTCTGCCGGCCACTCCTGCATCTTTACCGTCTCAGGGACT       280

S  S  C  C  P  F  P  E  A  V  A  C  G  D  H  H  C  C  P
TCCAGTTGCTGCCCCTTCCCAGAGGCCGTGGCATGCGGGGATGGCCATCACTGCTGCCCA        340

R  G  F  H  C  S  A  D  G  R  S  C  F  Q  R  S  G  N  N  S
CGGGGCTTCCACTGCAGTGCAGACGGGCGATCCTGCTTCCAAAGATCAGGTAACAACTCC      400

V  G  A  I  Q  C  P  D  S  Q  F  E  C  P  D  F  S  T  C  C
GTGGGTGCCATCCAGTGCCCTGATAGTCAGTTCGAATGCCCGGACTTCTCCACGTGCTGT      460

V  M  V  D  G  S  W  G  C  C  P  M  P  Q  A  S  C  C  E  D
GTTATGGTCGATGGCTCCTGGGGGTGCTGCCCCATGCCCCAGGCTTCCTGCTGTGAAGAC       520

R  V  H  C  C  P  H  G  A  F  C  D  L  V  H  T  R  C  I  T
AGGGTGCACTGCTGTCCGCACGGTGCCTTCTGCGACCTGGTTCACACCCGCTGCATCACA      580

P  T  G  T  H  P  L  A  K  K  L  P  A  Q  R  T  N  R  A  V
CCCACGGGCACCCACCCCCTGGCAAAGAAGCTCCCTGCCCAGAGGACTAACAGGGCAGTG      640

A  L  S  S  S  V  M  C  P  D  A  R  S  R  C  P  D  G  S  T
GCCTTGTCCAGCTCGGTCATGTGTCCGGACGCACGGTCCCGGTGCCCTGATGGTTCTACC      700

C  C  E  L  P  S  G  K  Y  G  C  C  P  M  P  N  A  T  C  C
TGCTGTGAGCTGCCCAGTGGGAAGTATGGCTGCTGCCCAATGCCCAACGCCACCTGCTGC      760

S  D  H  L  H  C  C  P  Q  D  T  V  C  D  L  I  Q  S  K  C
TCCGATCACCTGCACTGCTGCCCCCAAGACACTGTGTGTGACCTGATCCAGAGTAAGTGC      820

L  S  K  E  N  A  T  T  D  L  L  T  K  L  P  A  H  T  V  G
CTCTCCAAGGAGAACGCTACCACGGACCTCCTCACTAAGCTGCCTGCGCACACAGTGGGG     880

D  V  K  C  D  M  E  V  S  C  P  D  G  Y  T  C  C  R  L  Q
GATGTGAAATGTGACATGGAGGTGAGCTGCCCAGATGGCTATACCTGCTGCCGTCTACAG     940

S  G  A  W  G  C  C  P  F  T  Q  A  V  C  C  E  D  H  I  H
TCGGGGGCCTGGGGCTGCTGCCCTTTTACCCAGGCTGTGTGCTGTGAGGACCACATACAC    1000

C  C  P  A  G  F  T  C  D  T  Q  K  G  T  C  E  Q  G  P  H
TGCTGTCCCGCGGGGTTTACGTGTGACACGCAGAAGGGTACCTGTGAACAGGGGCCCCAC    1060
```

Figure 22 (cont.)

```
  Q   V   P   W   M   E   K   A   P   A   H   L   S   L   P   D   P   Q   A   L
CAGGTGCCCTGGATGGAGAAGGCCCCAGCTCACCTCAGCCTGCCAGACCCACAAGCCTTG          1120

K   R   D   V   P   C   D   N   V   S   S   C   P   S   S   D   T   C   C   Q
AAGAGAGATGTCCCCTGTGATAATGTCAGCAGCTGTCCCTCCTCCGATACCTGCTGCCAA          1180

L   T   S   G   E   W   G   C   C   P   I   P   E   A   V   C   C   S   D   H
CTCACGTCTGGGGAGTGGGGCTGCTGTCCAATCCCAGAGGCTGTCTGCTGCTCGGACCAC          1240

Q   H   C   C   P   Q   G   Y   T   C   V   A   E   G   Q   C   Q   R   G   S
CAGCACTGCTGCCCCCAGGGCTACACGTGTGTAGCTGAGGGGCAGTGTCAGCGAGGAAGC          1300

E   I   V   A   G   L   E   K   M   P   A   R   R   A   S   L   S   H   P   R
GAGATCGTGGCTGGACTGGAGAAGATGCCTGCCCGCCGGGCTTCCTTATCCCACCCCAGA          1360

D   I   G   C   D   Q   H   T   S   C   P   V   G   Q   T   C   C   P   S   L
GACATCGGCTGTGACCAGCACACCAGCTGCCCGGTGGGGCAGACCTGCTGCCCGAGCCTG          1420

G   G   S   W   A   C   C   Q   L   P   H   A   V   C   C   E   D   R   Q   H
GGTGGGAGCTGGGCCTGCTGCCAGTTGCCCCATGCTGTGTGCTGCGAGGATCGCCAGCAC          1480

C   C   P   A   G   Y   T   C   N   V   K   A   R   S   C   E   K   E   V   V
TGCTGCCCGGCTGGCTACACCTGCAACGTGAAGGCTCGATCCTGCGAGAAGGAAGTGGTC          1540

S   A   Q   P   A   T   F   L   A   R   S   P   H   V   G   V   K   D   V   E
TCTGCCCAGCCTGCCACCTTCCTGGCCCGTAGCCCTCACGTGGGTGTGAAGGACGTGGAG          1600

C   G   E   G   H   F   C   H   D   N   Q   T   C   C   R   D   N   R   Q   G
TGTGGGGAAGGACACTTCTGCCATGATAACCAGACCTGCTGCCGAGACAACCGACAGGGC          1660

W   A   C   C   P   Y   R   Q   G   V   C   C   A   D   R   R   H   C   C   P
TGGGCCTGCTGTCCCTACCGCCAGGGCGTCTGTTGTGCTGATCGGCGCCACTGCTGTCCT          1720

A   G   F   R   C   A   A   R   G   T   K   C   L   R   R   E   A   P   R   W
GCTGGCTTCCGCTGCGCAGCCAGGGGTACCAAGTGTTTGCGCAGGGAGGCCCCGCGCTGG          1780

D   A   P   L   R   D   P   A   L   R   Q   L   L
GACGCCCCTTTGAGGGACCCAGCCTTGAGACAGCTGCTG                               1819
```

METHODS OF USING EPITHELINS TO MODULATE CELL PROLIFERATION

This application is a divisional of application Ser. No. 07/668,648, filed Mar. 13, 1991, now U.S. Pat. No. 5,416,192, which is a continuation in part of application Ser. No. 07/504,508, filed Apr. 3, 1990, now abandoned, the contents of which are hereby incorporated by reference.

1. Introduction
2. Background of the Invention
3. Summary of the Invention
4. Brief Description of the Figures
5. Detailed Description of the Invention
   5.1. Production of Epithelins
      5.1.1. Isolation and Purification of Epithelins From Natural Cell Sources
      5.1.2. Chemical Synthesis of Epithelins
      5.1.3. Synthesis of Epithelins Using Recombinant DNA Technology
         5.1.3.1. Isolation or Generation of Epithelin Genes
         5.1.3.2. Construction of Epithelin Expression Vectors
         5.1.3.3. Identification of Transfectants or Transformants Expressing Epithelin Gene Products
      5.1.4. Epithelin Derivatives, Analogs and Peptides
   5.2. Anti-Epithelin Antibodies
   5.3. Biological Profile of the Epithelins
   5.4. Uses of the Epithelins, Epithelin-Encoding Nucleic Acid Molecules, Anti-Epithelin Antibodies and Epithelin Receptors
      5.4.1. Epithelin Proteins
      5.4.2. Epithelin-Encoding Nucleic Acid Molecules
6. Example: Preparation of Purified Epithelin 1 and And Epithelin 2 From Rat Kidney
   6.1. Purification Procedures
      6.1.1. Acid Ethanol Extraction
      6.1.2. Preparative Gel Permeation Chromatography
      6.1.3. Reversed-Phase HPLC of Preparative TSK-250 Fractions
      6.1.4. Further Purification of Epithelin 1 By Reversed-Phase and Gel Permeation HPLC
      6.1.5. Further Purification of Epithelin 2 By Reversed-Phase and Gel Permeation HPLC
   6.2. Bioassays
      6.2.1. Cell Growth Inhibitory Assay Using $^{125}$I-deoxyuridine Incorporation Into DNA
      6.2.2. Cell Growth Inhibitory and Stimulatory Assay Using Murine Keratinocytes
      6.2.3. Soft Agar Colony Assay
   6.3. Primary Structure Determinations
      6.3.1. Reduction and S-Pyridylethylation
      6.3.2. Enzymatic Cleavage of SPE-Epithelin 1 and SPE-Epithelin 2
      6.3.3. Peptide Isolation
      6.3.4. Amino Acid Analysis
      6.3.5. Amino Acid Sequence Determination
      6.3.6. Tricine-Sodium Dodecyl Sulfate-Polyacrylamide Gel Electrophoresis.
   6.4. Characteristics of the Epithelins I and II.
      6.4.1. Physical and Chemical Properties
      6.4.2. Purification of Epithelin 1 and Epithelin 2 and Certain Physical Properties
      6.4.3. Chemical Structure of Epithelin 1 and Epithelin 2
      6.4.4. Biological Properties of Epithelin 1 and Epithelin 2
7. Example: cDNA Cloning of the Epithelin Precursor and Transient Expression of Precursor and Mature Forms
   7.1 PCR cDNA Cloning
   7.2 Expression in COS Cells

1. INTRODUCTION

The present invention relates to a novel family of growth regulatory proteins which applicants have termed "epithelins", to methods for the production of epithelins, and to their diagnostic and therapeutic uses. Applicants have purified two members of the epithelin family, epithelin 1 and epithelin 2, from natural cell sources and have isolated cDNAs encoding several different epithelins. Epithelin 1 and epithelin 2 share substantial structural similarity yet are functionally distinct proteins. Epithelin 1 is a bifunctional growth regulator, capable of stimulating the growth of some cell types while inhibiting the growth of others. Epithelin 2 is functionally similar to epithelin 1 with respect to growth inhibitory bioactivity. In contrast, however, epithelin 2 is apparently not capable of eliciting the growth stimulatory activity characteristic of epithelin 1 and, in fact, antagonizes this epithelin 1 activity.

2. BACKGROUND OF THE INVENTION

Cellular growth and differentiation appear to be initiated, promoted, maintained, and regulated by a multiplicity of stimulatory, inhibitory, and synergistic factors and hormones. The alteration and/or breakdown of the cellular homeostasis mechanism seems to be a fundamental cause of growth-related diseases, including neoplasia. Growth modulatory factors are implicated in a wide variety of pathological and physiological processes including signal transduction, cell communication, growth and development, embryogenesis, immune response, hematopoiesis, cell survival and differentiation, inflammation, tissue repair and remodeling, atherosclerosis and cancer.

Epidermal growth factor (EGF), transforming growth factor-$\alpha$ (TGF$\alpha$), platelet-derived growth factor (PDGF), fibroblast growth factor (FGF), nerve growth factor (NGF), transforming growth factor-$\beta$ (TFG$\beta$), insulin growth factor I and II (IGF I, IGF II), hematopoietic growth factors such as erythropoietin, colony-stimulating factors (CSF 1 and 2), interleukins (IL-1 to 8), interferons (IFN $\alpha$, $\beta$, $\gamma$), tumor necrosis factor $\alpha$ and $\beta$ (TNF $\alpha$ and $\beta$), leukoregulin, oncostatin M, amphiregulin (AR) and other less defined factors are growth and differentiation modulatory proteins produced by a variety of cell types either under normal physiological conditions or in response to exogenous stimuli. Most of these factors appear to act in autocrine and paracrine fashions. (For reviews see: Goustin et al., 1986, Cancer Res. 46:1015–1029; Rozengurt, 1986, Science 234:161–166; Pardee, 1987, Cancer Res. 47:1488–1491; Sachs, 1986, Sci. Amer. 254:40–47; Marshall, 1987, Cell 50:5–6; Melcher and Anderson, 1987, Cell 30:715–720; Namen et al., .1988, J. Exp. Med. 167:988–1002; Baggiolini et al., 1989, J. Clin. Invest. 84:1045–1049; Clemens and McNurlan, 1985, Biochem, J. 226:345–360; Nathan, 1987, J. Clin. Invest. 79:319–326; Sporn and Roberts, 1986, J. Clin. Invest. 78:329–332; Old, 1987, Nature 326:330–331; Beutler and Cerami, 1987, New Engl. J. Med. 316:379–385; Weinstein, 1987, J. Cell. Biochem. 33:213–224; Zarling et al., 1987, Proc. Natl. Acad. Sci. USA 83:9739–9744; Shoyab et al., 1988, Proc. Natl. Acad. Sci. USA, 85:6528–6532; Shoyab et al., 1989, Science 243:1074–1076; Sporn and Todaro, 1985, N. Engl. J. Med. 303:878–880; Sporn and Roberts, 1985, Nature 313:745–747).

There is a great deal of interest in isolating, characterizing, and defining the functional mechanisms of growth modulatory factors because of their potential use in the diagnosis, prognosis, and treatment of cancer. Moreover, acquiring knowledge of these factors will aid in the understanding of the basic mechanisms behind normal growth control and the loss thereof in cancer cells.

3. SUMMARY OF THE INVENTION

The present invention is directed to epithelins, a novel family of low molecular weight, cysteine-rich proteins exhibiting bifunctional growth regulatory activities, to the use of epithelins in the diagnosis and treatment of human diseases, and to methods for the production of biologically active epithelins. Two members of the epithelin family, epithelin 1 and epithelin 2, have been identified and purified to apparent homogeneity, enabling applicants to determine the primary structures, physical properties and functional characteristics of these novel growth modulators. Several other members of the epithelin family have been identified by cDNA cloning. Epithelin 1 is a polypeptide comprising 56 amino acids, while epithelin 2 comprises 57 amino acids. Structurally, epithelin 1 and epithelin 2 share 47% homology at the amino acid level and each contains 12 identically positioned cysteine residues.

Epithelins may be produced by isolation and purification from natural sources, by chemical synthesis, or by recombinant DNA technology. In a particular embodiment of the invention, described more fully by way of example herein (Section 6,infra), epithelin 1 and epithelin 2 are isolated from rat kidney tissue and subsequently purified to apparent homogeneity using a combination of gel permeation and reversed phase high performance liquid chromatography (HPLC). As further described in Section 6, infra, applicants have thoroughly characterized the purified epithelins I and II with respect to their structural, physical, chemical, and functional characteristics.

4. BRIEF DESCRIPTION OF THE FIGURES

FIG. 1. Preparative gel permeation HPLC of crude extract.

Figure 2:
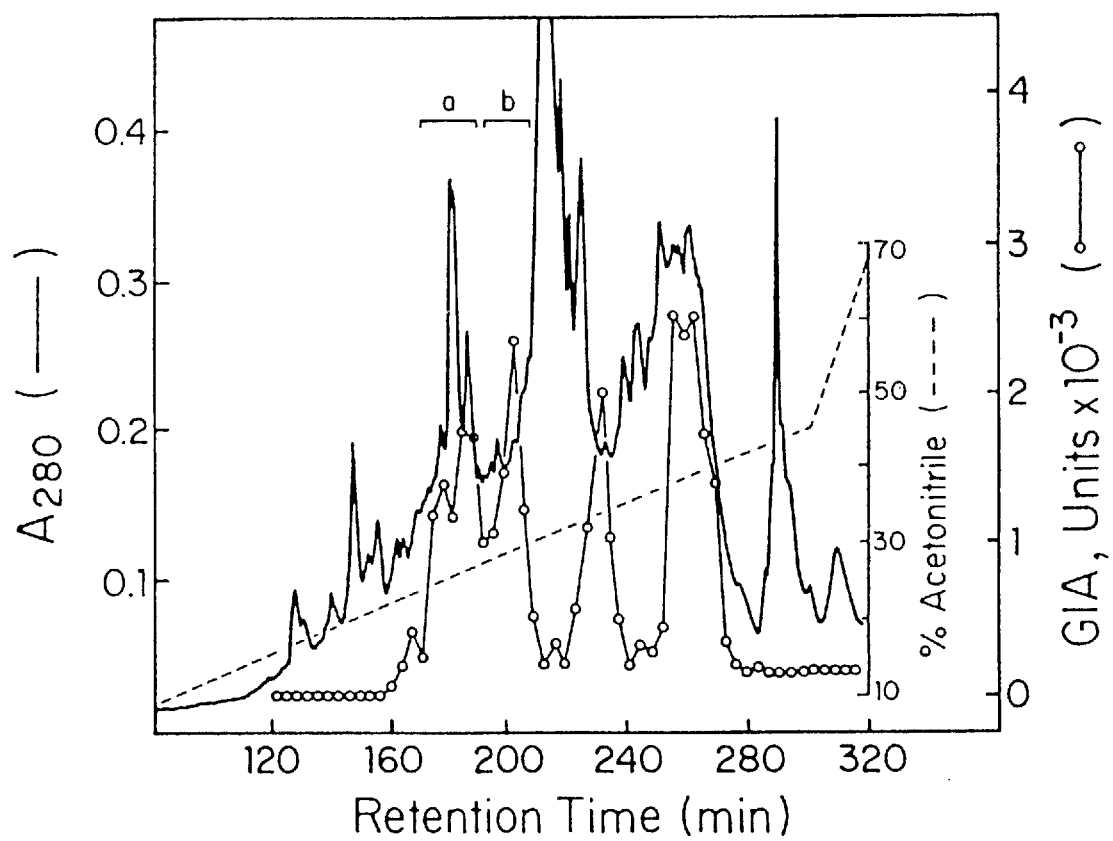

FIG. 2. Preparative reversed phase HPLC of pooled fractions 25–28 from 28 runs of FIG. 1.

Figure 3:
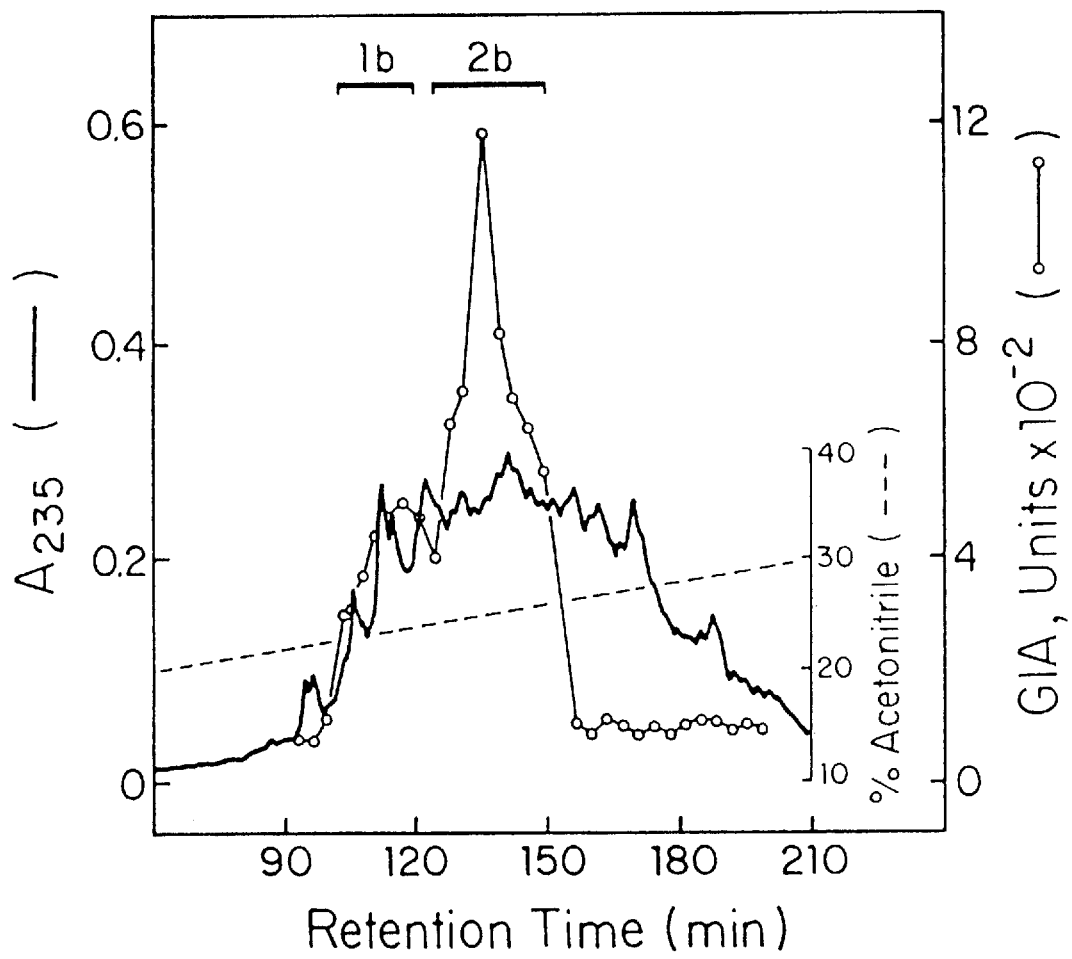

FIG. 3. Semi-preparative reversed phase HPLC of pooled fractions 55–59 from FIG. 2.

Figure 4:
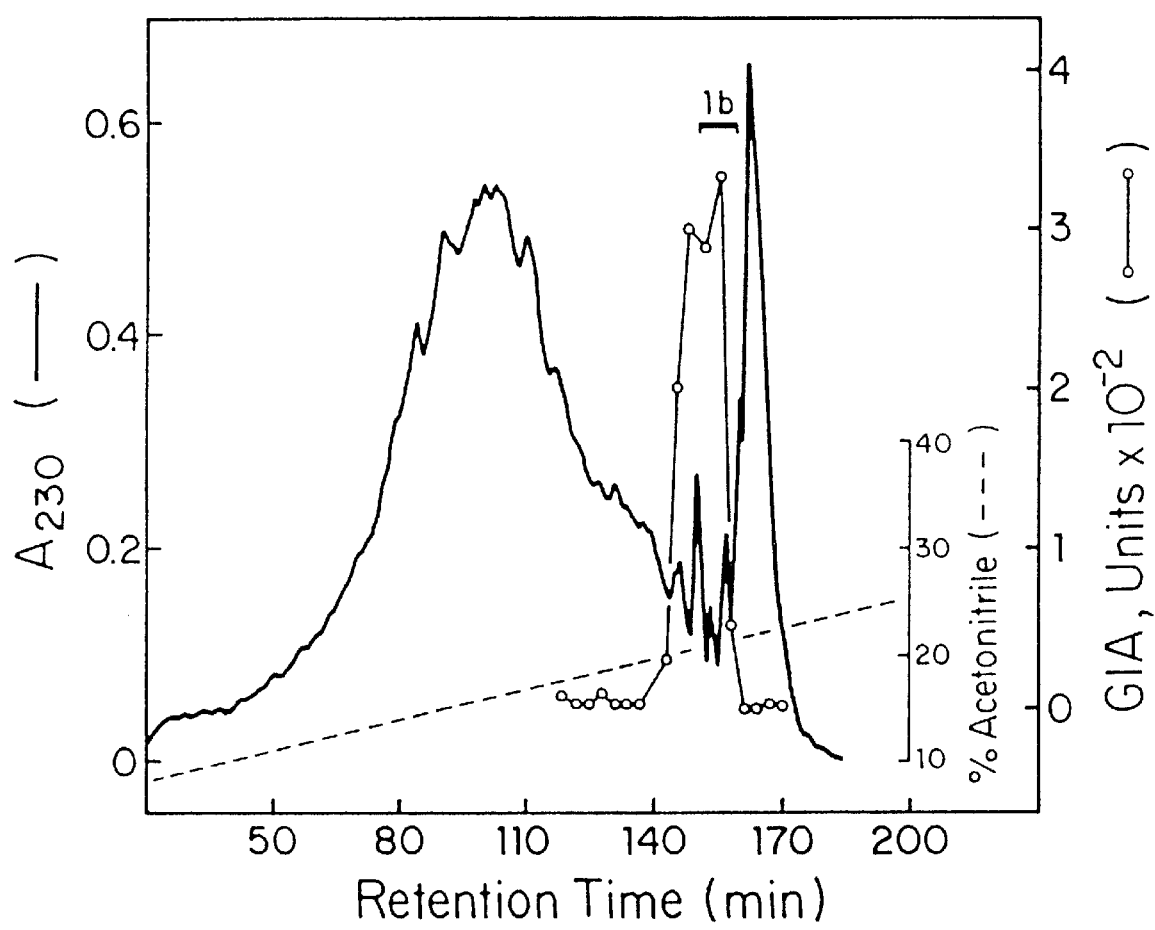

FIG. 4. Analytical reversed phase HPLC of pool 1b from previous run.

Figure 5:
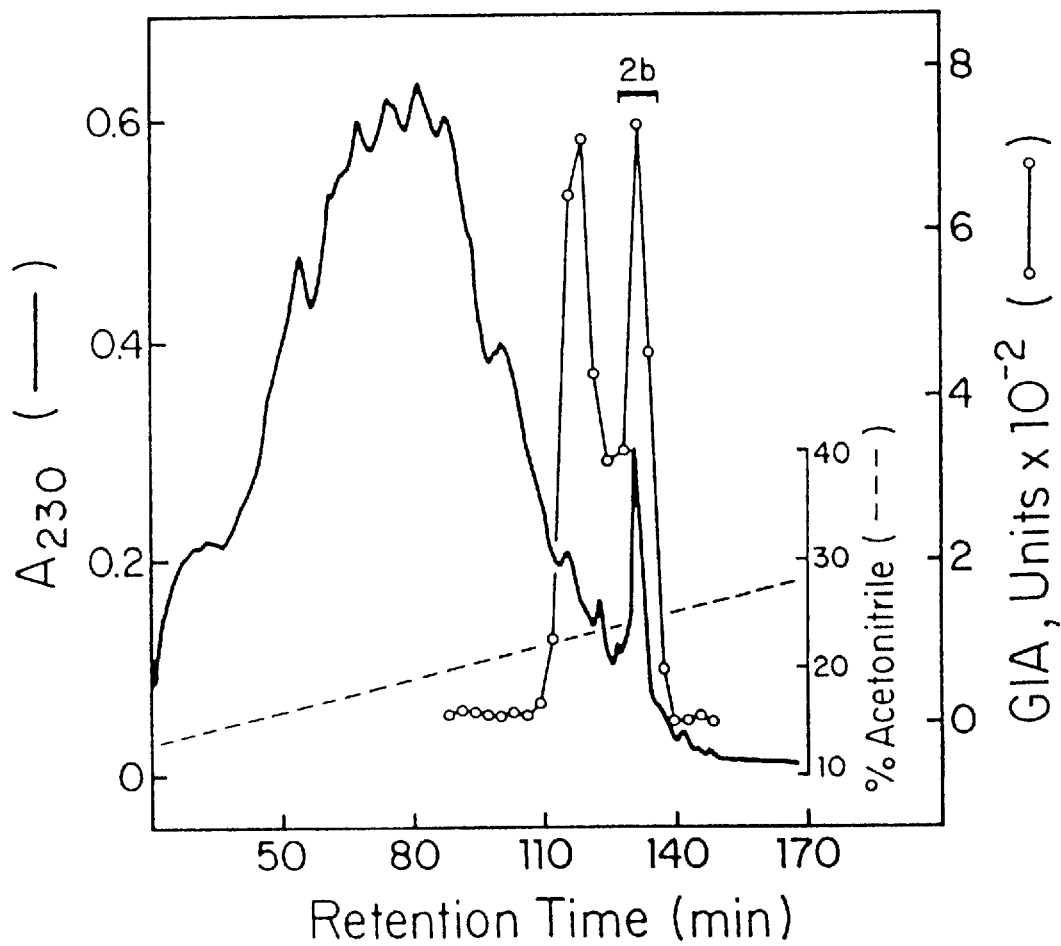

FIG. 5. Analytical reversed phase HPLC of pool 2b from FIG. 3.

Figure 6A:
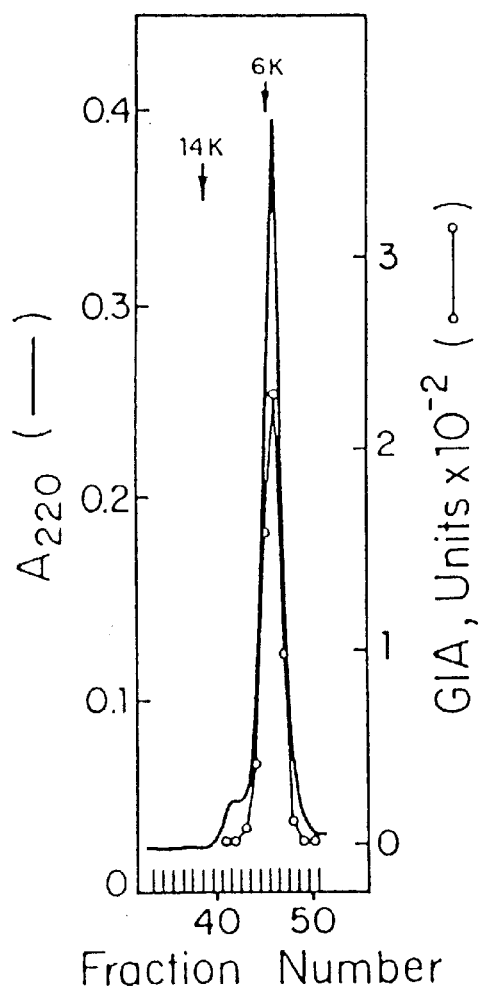
Figure 6B:
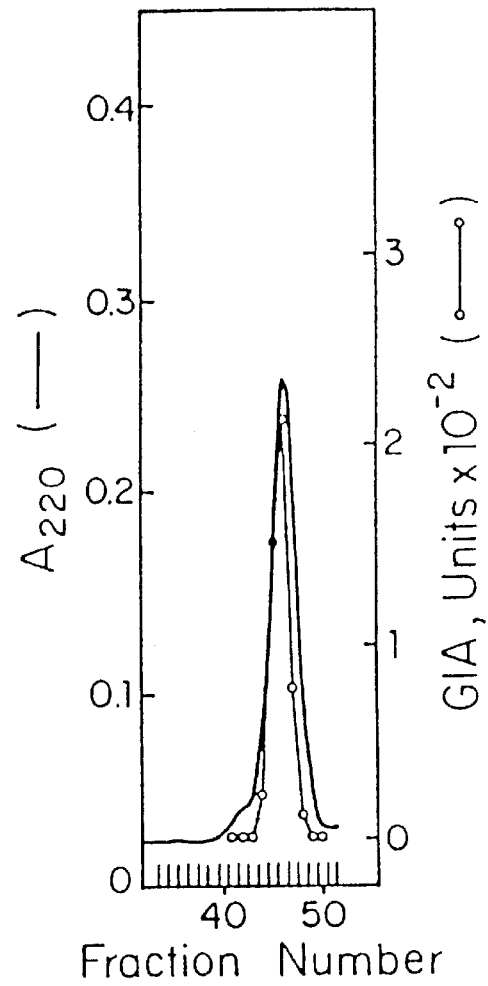

FIG. 6(A–B). Analytical gel permeation chromatography of the concentrated fractions 51(FIG. 6A) and 52(FIG. 6B) from FIG. 4.

Figure 7A:
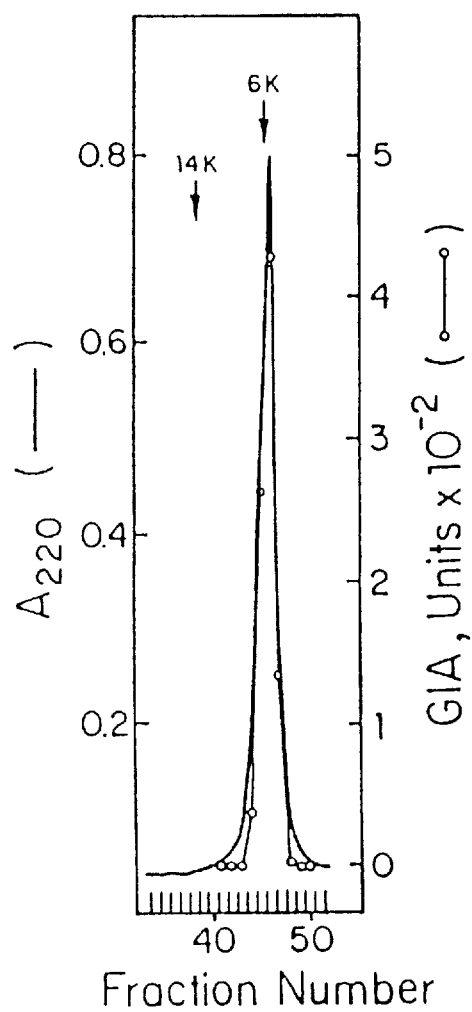
Figure 7B:
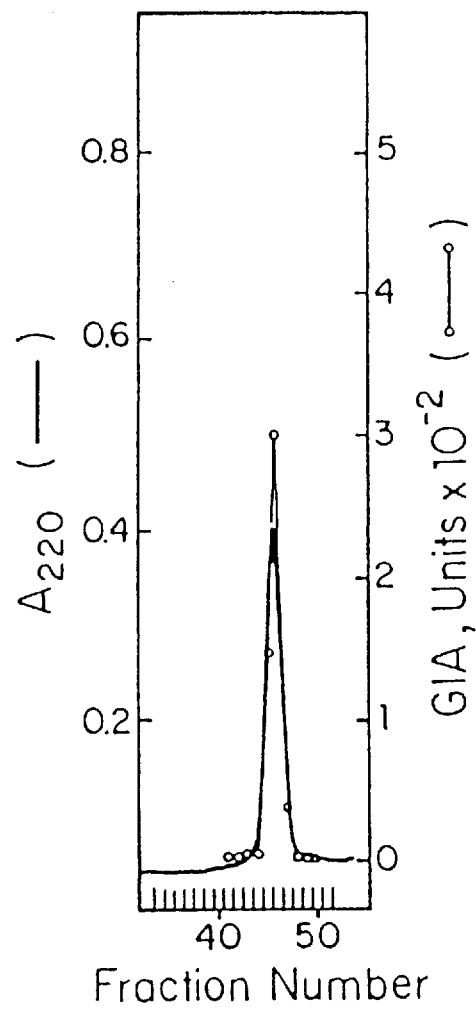

FIG. 7(A–B). Analytical gel permeation chromatography of the concentrated fractions 44(FIG. 7A) and 45(FIG. 7B) from FIG. 5.

Figure 8:
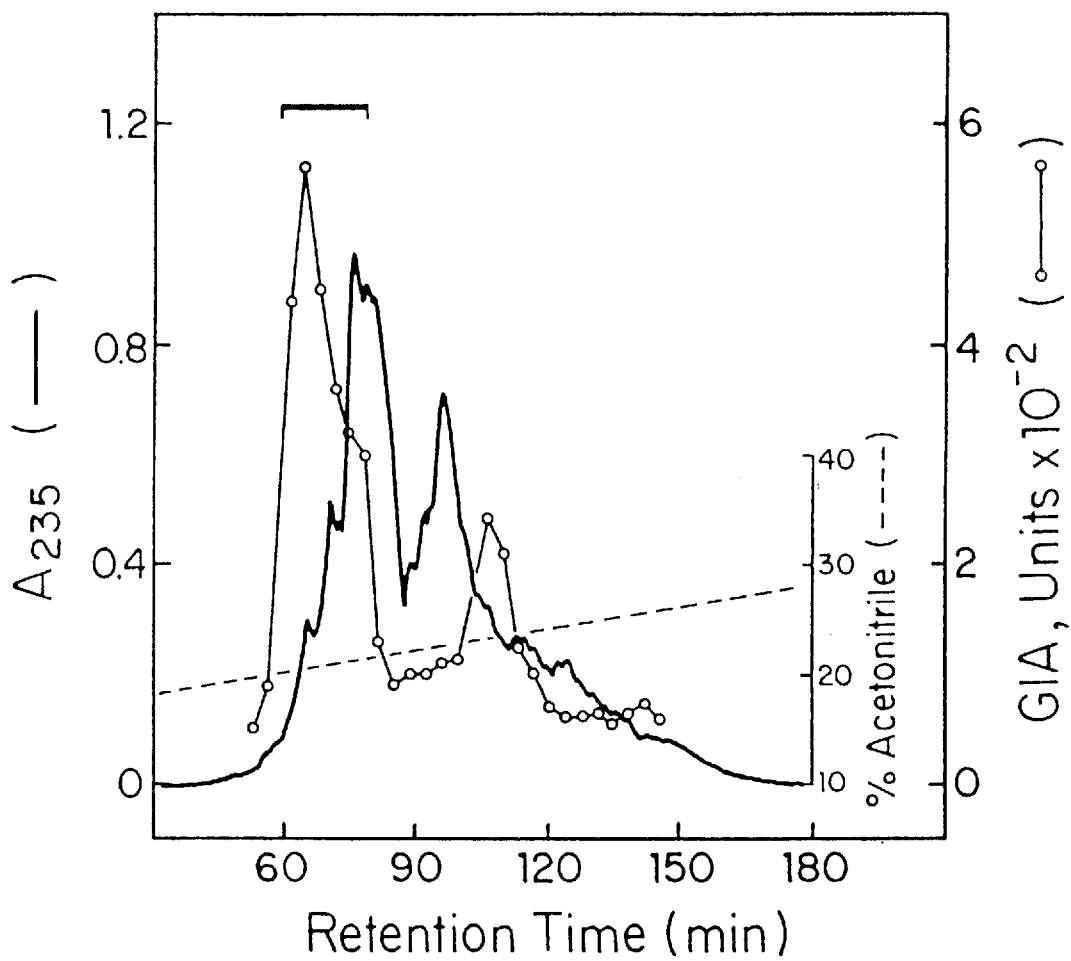

FIG. 8. Semi-preparative reversed phase HPLC of fractions 50–54 from FIG. 2.

Figure 9:
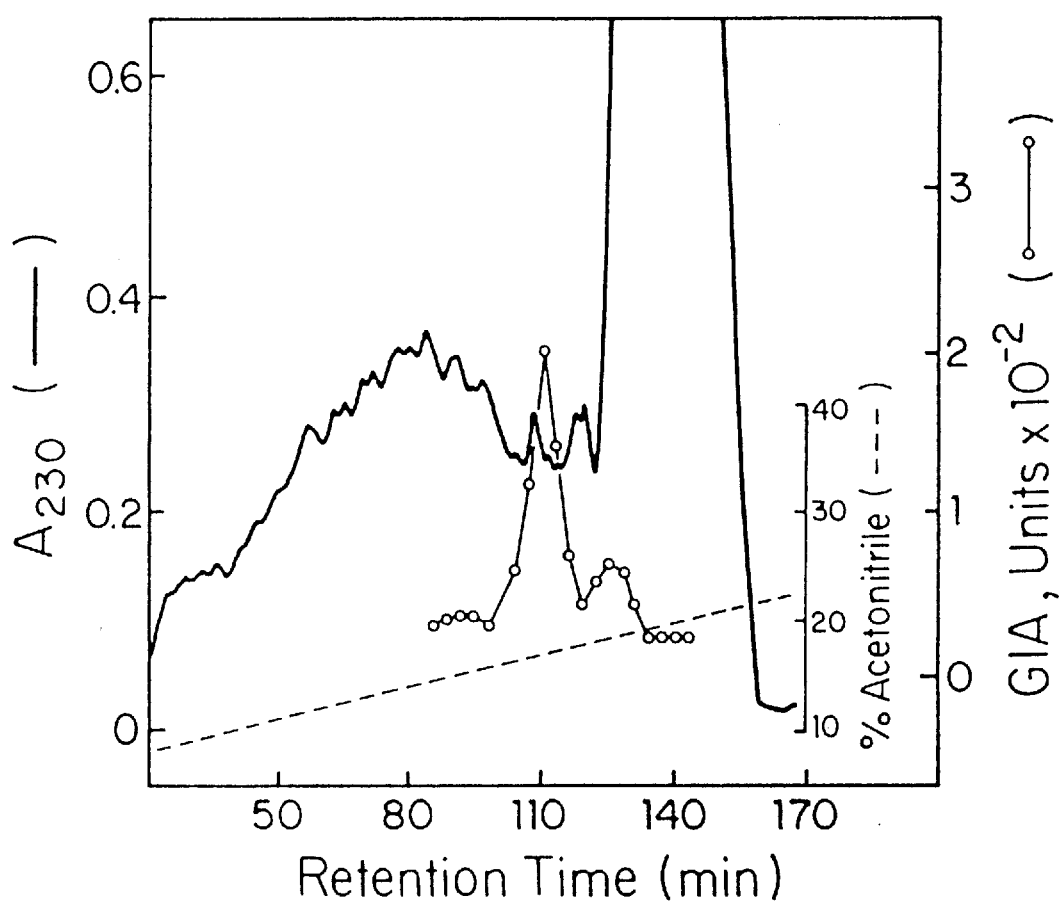

FIG. 9. Analytical reversed phase HPLC of fractions 18–23 from previous run.

FIG. 10(A–B). Analytical gel permeation chromatography of fractions from FIG. 9. Chromatography was performed as described in Section 6.1., infra. (FIG. 10A) HPLC of concentrated fraction 36; (FIG. 10B) HPLC of concentrated fraction 37; (FIG. 10C) HPLC of concentrated fraction 38; (FIG. 10D) rechromatography of pooled fractions 48 and 49 from A–C, then concentrated.

Figure 11:
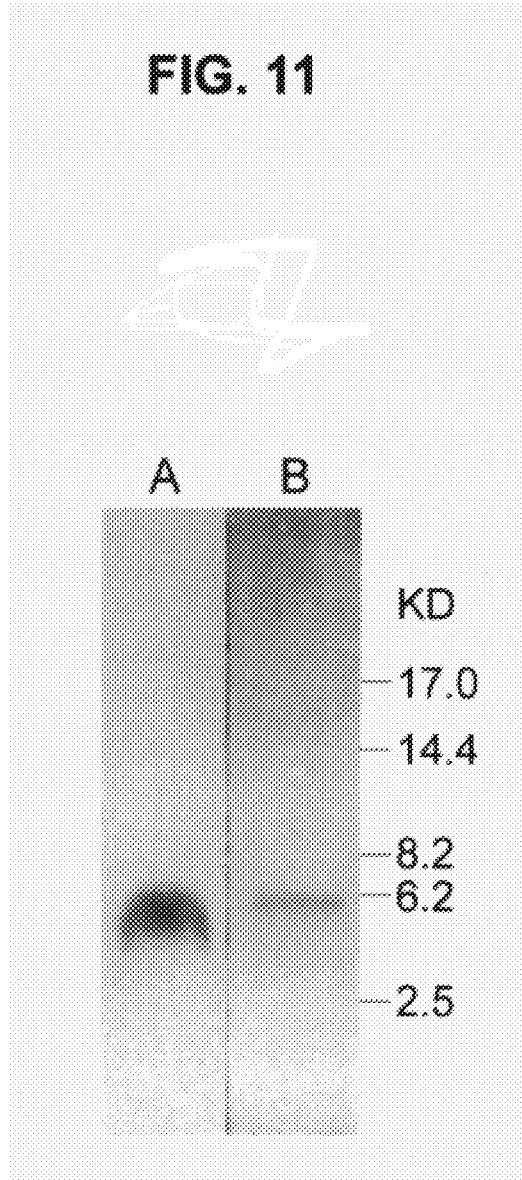

FIG. 11(A–B). Tricene-SDS-PAGE analysis of epithelin 1 and epithelin 2. An 18% minigel (0.75 mm×10 cm×7 cm) was run at room temperature at a constant voltage of 90 volts for 4.5 hr in a Bio-Rad mini-protein II electrophoresis apparatus. Dried samples were suspended in 10 µl sample buffer (50 nM Tris pH 6.8, 12% glycerol (w/v), 4% SDS, 4% mercaptoethanol (v/v) and 0.01% serva blue G.) incubated at 95° C. for five minutes and then applied on the gel. The molecular weight markers were five polypeptides from the cleavage of the horse heart myoglobin by cyanogen bromide (Sigma Chem. Co.). (FIG. 11A) epithelin 1; (FIG. 11B) epithelin 2.

Figure 12:
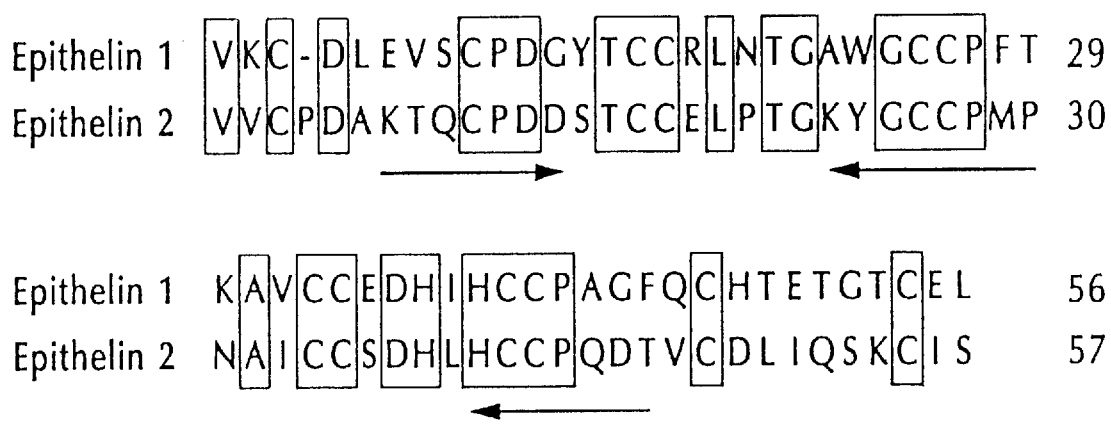

FIG. 12. Amino acid sequences and alignment of epithelin 1 (amino acid residues 272 through 335 of SEQ ID NO:2) and epithelin 2 (amino acid residues 205 through 261 of SEQ ID NO:2) purified from rat kidney. The standard single letter code for amino acids is used: Alanine (A); Arginine (R); Asparagine (N); Aspartic acid (D); Cysteine (C); Glutamine (Q); Glutamic acid (E); Glycine (G); Histidine (H); Isoleucine (I); Leucine (L); Lysine (K); Methionine (M); Phenylalanine (F); Proline (P); Serine (S); Threonine (T); Tryptophan (W); Tyrosine (Y); and Valine (V). The peptide sequences used to design oligonucleotide primers and probes are underlined.

Figure 13:
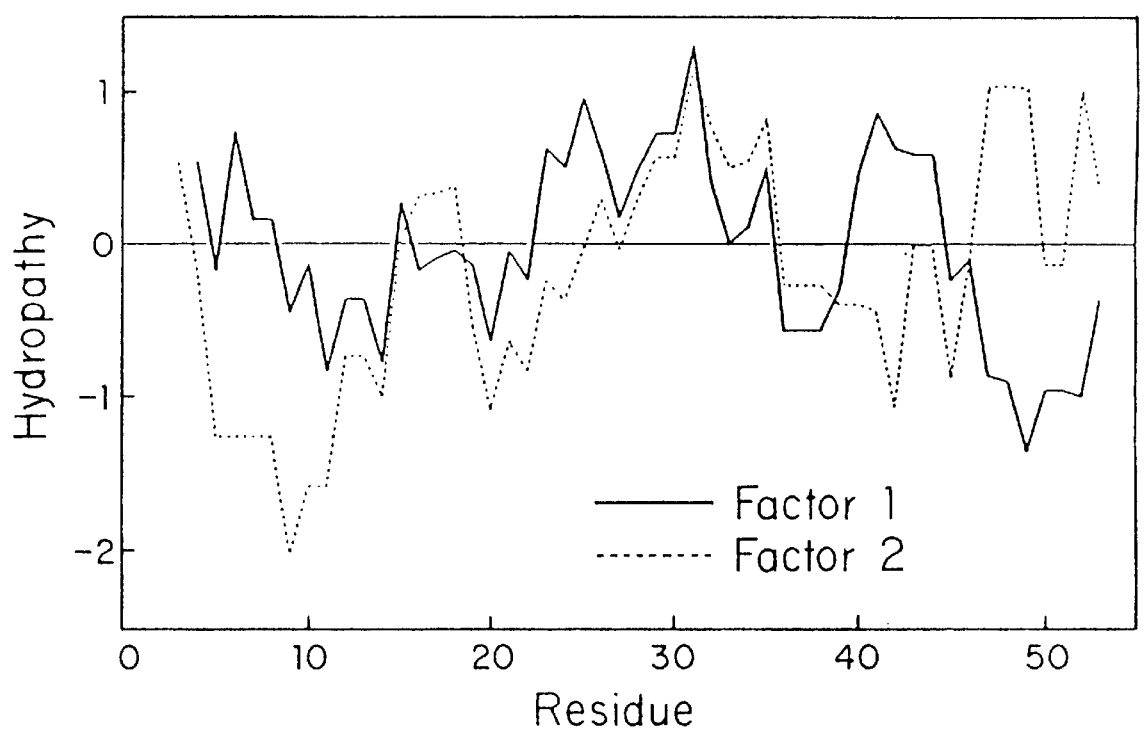

FIG. 13. Hydropathy analysis of epithelin 1 and 2 (Kyte and Doolittle). ___, epithelin 1; . . . , epithelin 2.

Figure 14:
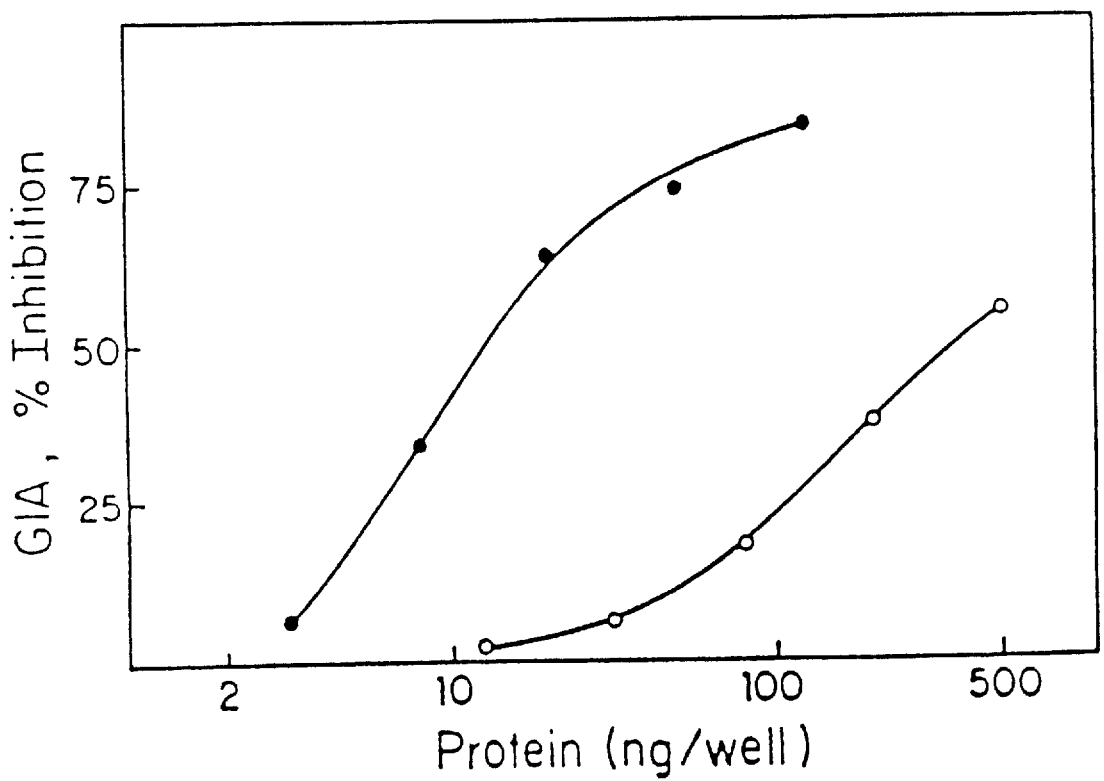

FIG. 14. Dose response curve of epithelin 1 and epithelin 2 on the inhibition of $^{125}$I-deoxyuridine incorporation into DNA of A431 cells. ●, epithelin 1; o, epithelin 2.

Figure 15A:
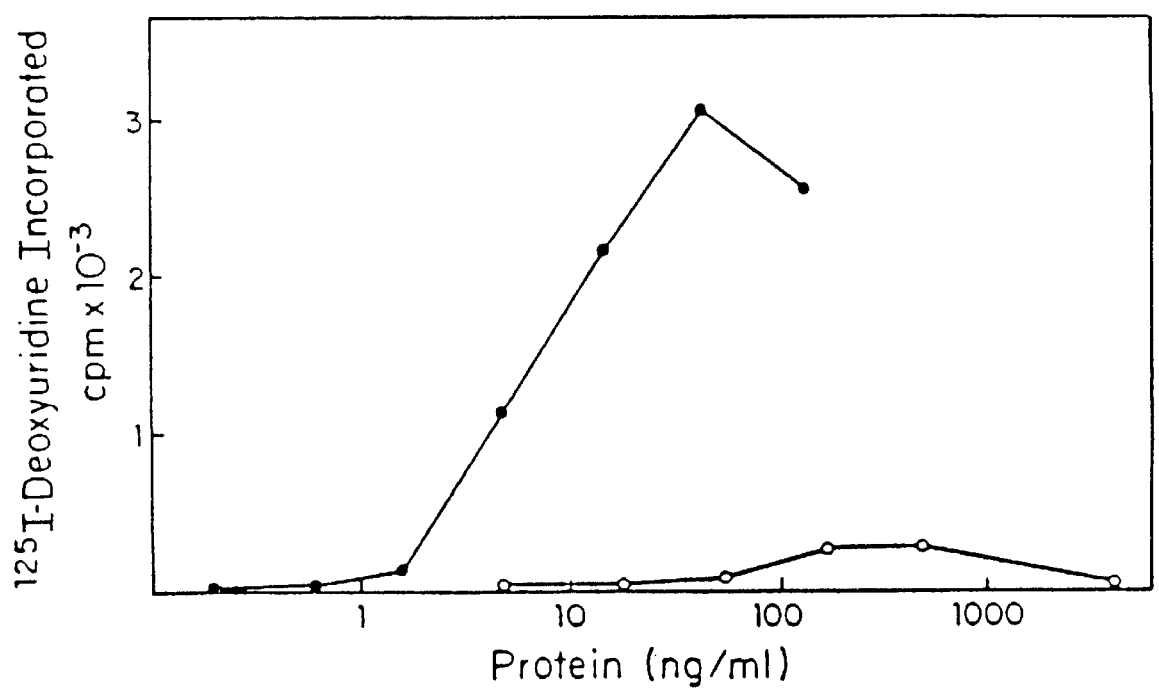
Figure 15B:
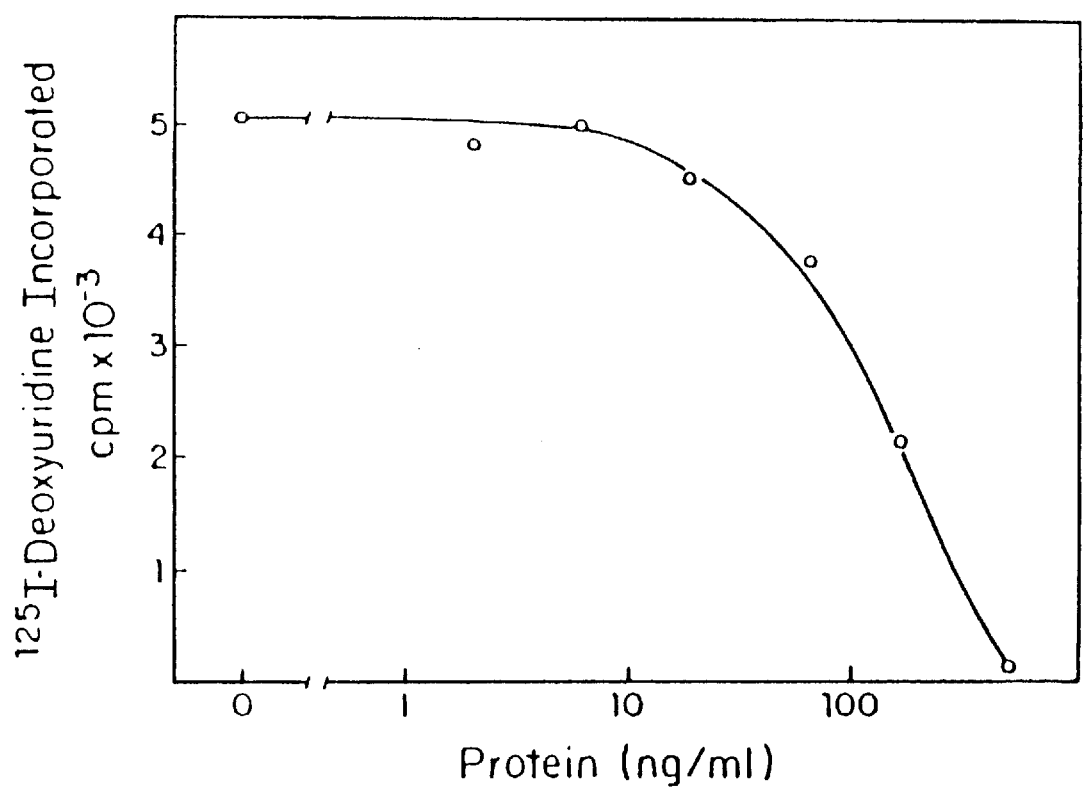

FIG. 15(A–B). (FIG. 15A) Effect of epithelin 1 and epithelin 2 on the stimulation of $^{125}$I-deoxyuridine incorporation into DNA of the murine keratinocyte cell line Balb/MK. 2,000–4,000 cells were plated per well in 96 well plates in low-calcium medium containing 5% dialyzed FBS. Then GSA assays were performed as described in Section 6.2., infra. ●, epithelin 1; o, epithelin 2. (FIG. 15B) Effect of various concentrations of epithelin 2 on epithelin 1 (20 ng/ml) elicited incorporation of $^{125}$I-deoxyuridine into DNA of Balb/MK cells.

Figure 16A:
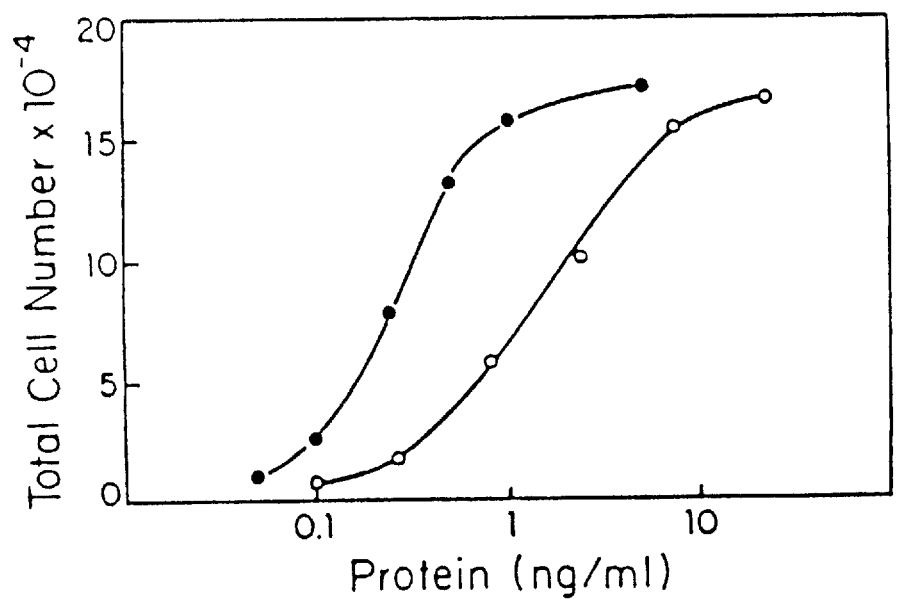
Figure 16B:
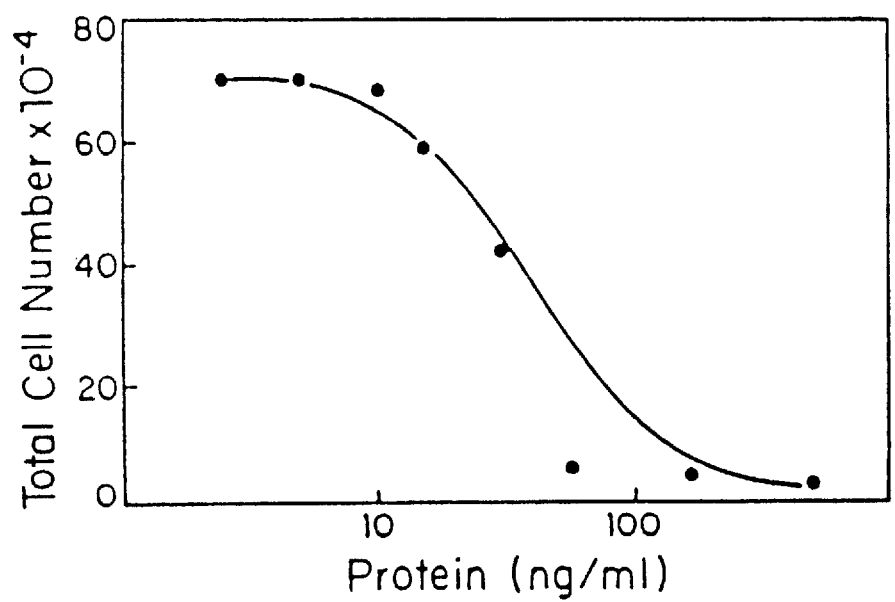

FIG. 16(A–B). (FIG. 16A) Effect of epithelin 1 and epidermal growth factor (EGF) on the growth of Balb/MK cells. Assays were performed as described in Section 6.2., infra. ●, epithelin 1; o, EGF (FIG. 16B) Effect of various concentrations of epithelin 2 on the epithelin 1 (20 ng/ml) induced growth of murine keratinocytes.

Figure 17:
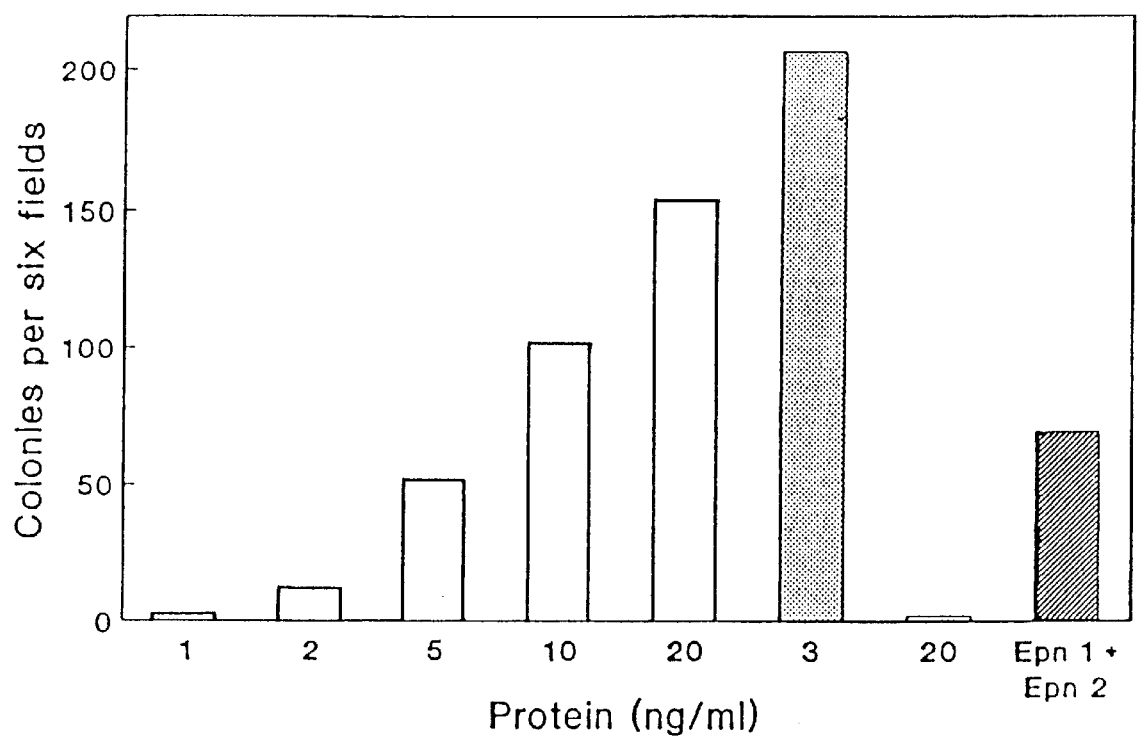

FIG. 17. Effect of epithelin 1 and 2 on NRK-SA6 cell colony formation in soft agar in the presence of TFGβ (1 ng/ml). The colony formation assay used is described in Section 6.2.3, infra. Solid bars, epithelin 1; stippled bar, epidermal growth factor; open bar, epithelin 2; hatched bar, 20 ng/ml epithelin 1 plus 500 ng/ml epithelin 2.

FIG. 18. Dot matrix alignment of the 589 amino acid rat epithelin precursor compared against itself. Each point represents a stretch of five out of ten identical residues.

Figure 19:
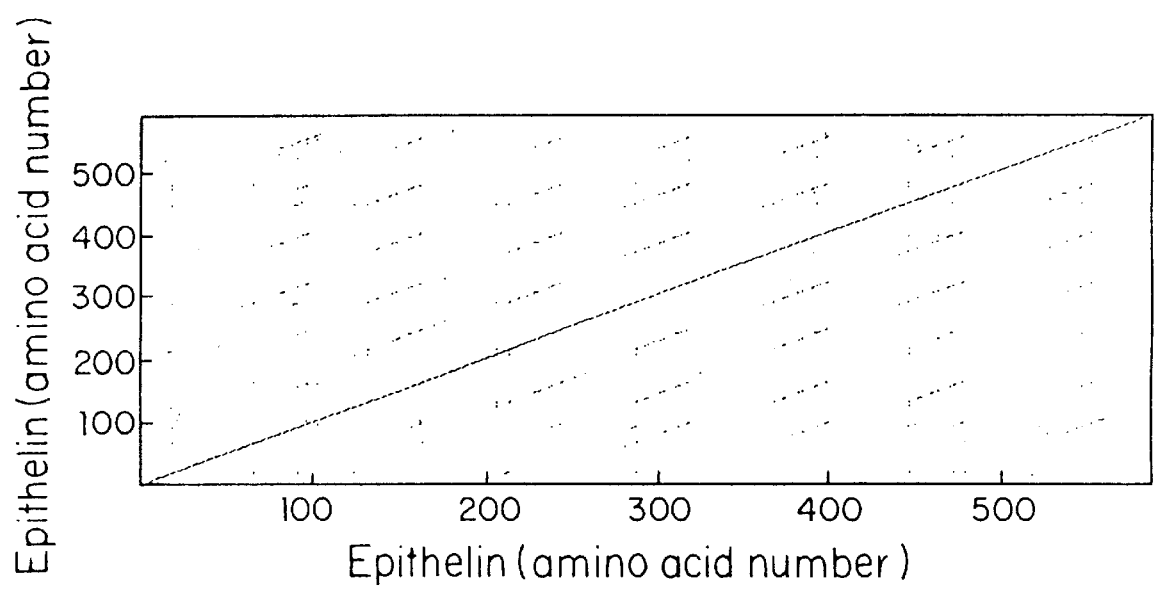

FIG. 19(a–B). (FIG. 19A) Composite secondary structure analysis of rat epithelin precursor. (FIG. 19B) Hydropathy of rat epithelin precursor.

Figure 20A:
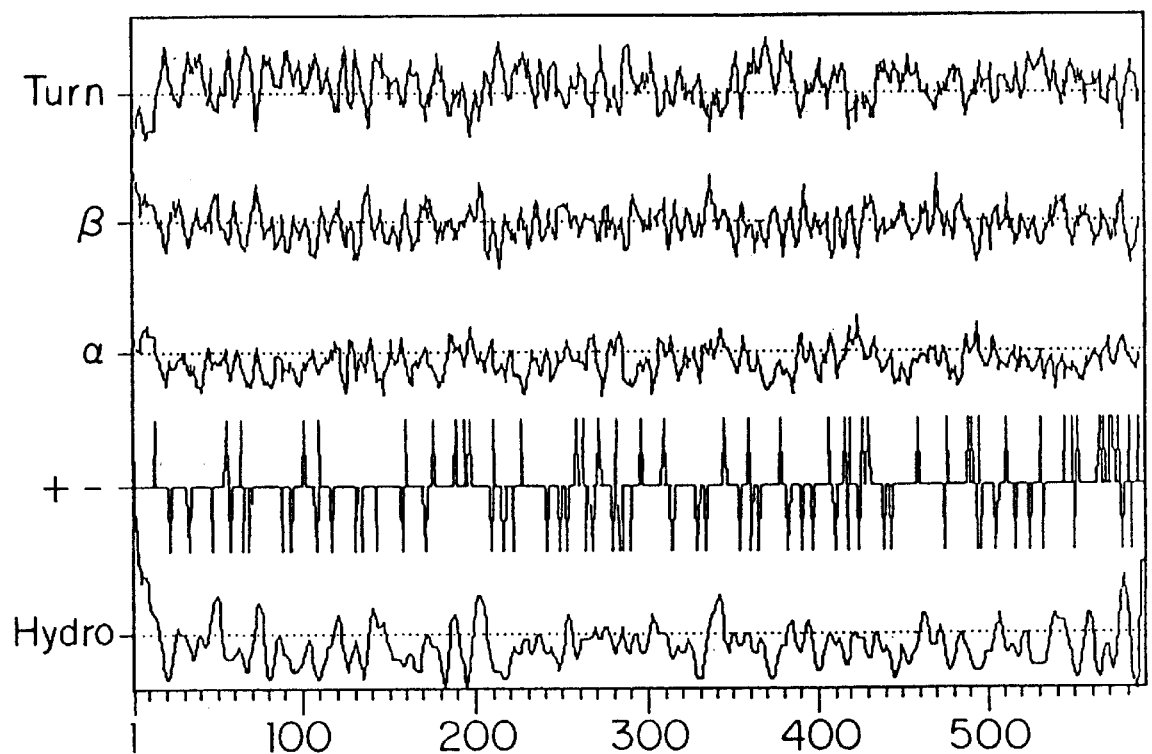
Figure 20B:
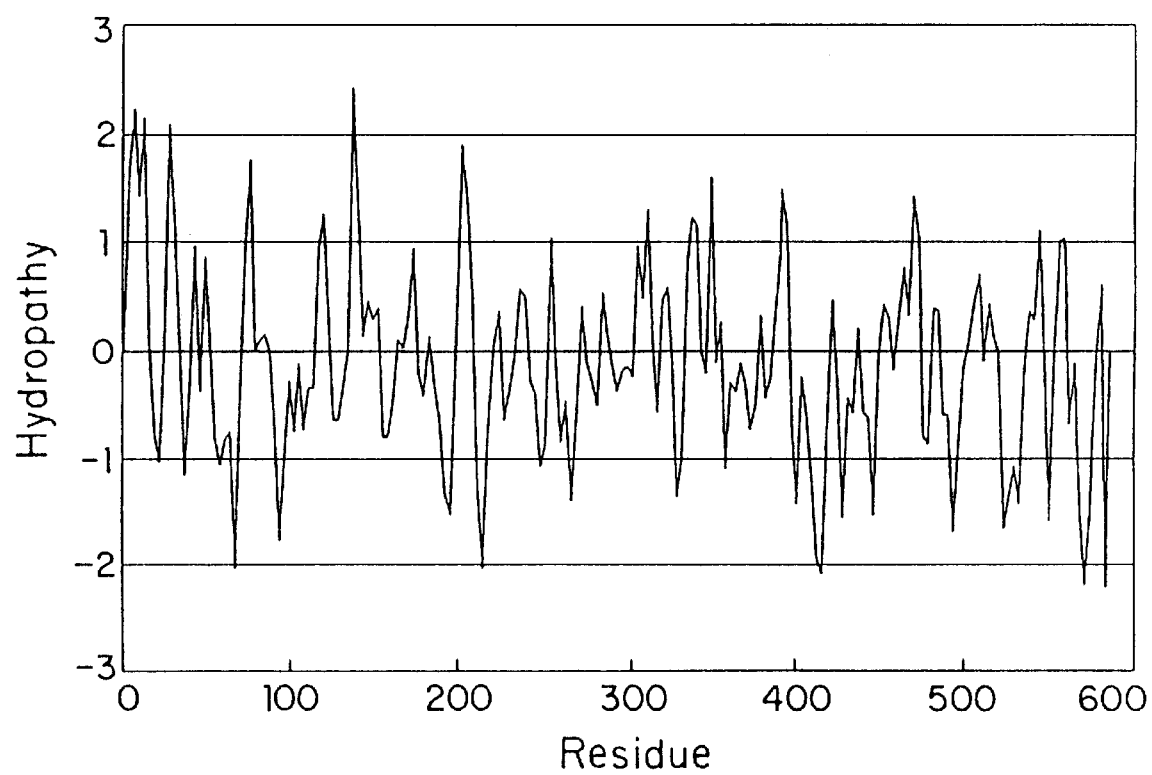

FIG. 20(A–B). (FIG. 20A) Protein sequence comparison between the human, rat, and mouse epithelin precursor deduced from cDNA clones. Sequences are displayed using the single-letter code with identical residues denoted with dots. Gaps were introduced for optimal alignment and are shown by a dash. The predicted rat epithelin signal sequence is underlined and the seven cysteine-rich motifs are boxed. Each sequence represents a consensus based on cDNA and PCR clones isolated from human, rat, or mouse kidney RNA. Arrows mark the boundaries of a 234 bp exon, a region absent in one rat cDNA clones. (FIG. 20B) Amino acid sequences of rat, mouse, and human epithelins. (FIG. 20C) Consensus cysteine motif conserved among the epithelins. (FIG. 20D) Alignment of the C-terminal domain (amino acids 254–315) of a tomato (*Lycopersicon esculentum*) thiol protease with epithelin 1 and 2.

FIG. 21(A–B). Expression of recombinant epithelin in COS cells. (FIG. 21A) $^{35}$S-cysteine labeled supernatants from COS cells transfected with the following cDM8-based expression constructs: lane 1, crEPN1.6 containing the complete rat epithelin coding region; lane 2, crEPN1.4, containing a rat epithelin cDNA isoform lacking a 234 bp exon; lane 3, mock-transfected control. (FIG. 21B) $^{35}$S-cysteine labeled supernatants from COS cells transfected with the following cDM8 expression constructs: lane 1, cβrEPN1, containing a simian TGF-β1 signal sequence preceding the coding region of mature rat epithelin 1; lane 2, cβrEPN2, a similar plasmid based on rat epithelin 2.

FIG. 22. Dendrogram representation of a cluster analysis between the epithelin cysteine-rich motifs from rat, mouse, and human sources. Below is a diagram of the epithelin precursor showing the position of the 7 motifs within the precursor. The 28 cysteine-rich motifs were aligned on PCGENE (Intellignetics, Inc. Mountain View, Calif.) using the CLUSTAL multiple alignment program. The pairwise similarity scores were transformed into a difference matrix which was analyzed using the Ward's method of cluster analysis (SPSS/PC+, Chicago, Ill.). This method uses squared Eclidean distances to place branch points.

5. DETAILED DESCRIPTION OF THE INVENTION

The present invention is directed to a novel family of growth regulatory proteins termed "epithelins". The epithelins appear to comprise several distinct members sharing significant structural homology. Two members of the epithelin family, epithelin 1 and epithelin 2, have been purified from natural sources, and cDNAs encoding these and several other members of the epithelin family have been isolated from rat, human, bovine, murine and chicken, among other cell sources.

More particularly, the invention is directed to each and every member of the epithelin family, epithelin derivatives and analogues, epithelin-encoding nucleic acid molecules (e.g., cDNAs, genomic DNAs, RNAs, anti-sense RNAs, etc.), traditional and recombinant DNA based methods for the production of epithelins, recombinant epithelin expression vectors, and diagnostic and/or therapeutic uses of mature and precursor epithelins, epithelin-encoding nucleic acid molecules, anti-epithelin antibodies and epithelin receptor(s).

5.1. PRODUCTION OF EPITHELINS

The individual epithelins may be produced by several general approaches, including isolation from natural sources, solid phase peptide synthesis, and recombinant DNA technology.

5.1.1. ISOLATION AND PURIFICATION OF EPITHELINS FROM NATURAL CELL SOURCES

Applicants' DNA cloning efforts have revealed that messenger RNAs encoding the various epithelins are expressed in a number of different cell types representing a broad species range. Therefore, applicants anticipate that the individual members of the epithelin family may be isolated from a wide variety of organs, tissues, and/or other cell sources. The epithelins may be separated from each other and purified from such cell sources by using various separation and purification techniques known in the art, including but not limited to chromatographic techniques (e.g., reversed phase liquid, gel permeation, liquid exchange, ion exchange, size exclusion, and affinity chromatography), centrifugation, electrophoretic procedures, differential solubility, etc.

In a specific embodiment of the invention, described more fully by way of example in Section 6., infra, two members of the epithelin family (epithelins 1 and 2) are isolated from rat kidney tissue and subsequently purified to apparent homogeneity using, inter alia, a combination of gel permeation and reversed phase high performance liquid chromatographies (HPLC). Epithelins 1 and 2 purified in this manner are single chain polypeptides comprising 56 and 57 amino acid residues, respectively, and share significant structural characteristics. Functionally, epithelin 1 appears to be a true bifunctional growth modulator, capable of stimulating and inhibiting cell growth. Epithelin 2 appears functionally distinct inasmuch as it specifically antagonizes the cell growth stimulatory activity induced by epithelin 1. Like epithelin 1, though generally to a lesser degree, epithelin 2 is also capable of inhibiting cell growth. The functional, structural, physical and other properties of epithelin 1 and epithelin 2 have been determined and are described in Section 6.4., infra. The six-step method of preparing purified epithelin 1 and epithelin 2 described in Section 6., infra, and/or modifications thereof, may also be used to isolate other members of the epithelin family.

5.1.2. CHEMICAL SYNTHESIS OF EPITHELINS

The individual members of the epithelin family may be produced using chemical methods to synthesize the corresponding amino acid sequences in whole or in part. For example, epithelins may be synthesized by solid phase techniques (Stewart and Young, *Solid Phase Peptide Synthesis*, 2nd edition, 1984). Purification and/or refolding into biologically active conformations of epithelins synthesized in this manner may be accomplished by various techniques known in the art. The amino acid compositions of the synthesized epithelins may be confirmed by amino acid analysis.

5.1.3. SYNTHESIS OF EPITHELINS USING RECOMBINANT DNA TECHNOLOGY

Biologically active mature and precursor epithelins may be produced by the expression of epithelin-encoding DNAs in a recombinant host cell system. General techniques for the isolation of gene sequences, the construction of vectors capable of directing the synthesis of encoded proteins, and the expression and/or secretion of biologically active recombinant proteins are well known in the art.

Production of an epithelin using recombinant DNA technology may be divided into a four-step process for the purposes of description: (1) isolation or generation of the coding sequence (gene) for a precursor or mature form of the epithelin; (2) construction of an expression vector capable of directing the synthesis of the desired epithelin; (3) transfection or transformation of appropriate host cells capable of replicating and expressing the epithelin gene and/or processing the gene product to produce the desired epithelin; and (4) identification and purification of the desired epithelin product.

The cloning of a rat epithelin precursor, its expression, and the expression of mature rat epithelin 1 and 2 are described by the examples presented in Section 7., et seq, infra.

5.1.3.1. ISOLATION OR GENERATION OF EPITHELIN GENES

The nucleotide coding sequences of the various individual epithelins, or functional equivalents thereof, may be used to construct recombinant expression vectors which will direct the expression of the desired epithelin product. Epithelin-encoding nucleotide sequences may be obtained from a variety of cell sources which produce epithelin-like activities or which express epithelin-encoding mRNA. Applicants have identified a number of suitable human and murine tissue sources in this regard, including but not limited to placenta, colon, kidney, testes, adrenal, breast, ovary, duodenum, thymus, and lung tissues.

Epithelin coding sequences may be obtained by cDNA cloning from RNA isolated and purified from such cell sources or by genomic cloning. Either cDNA or genomic libraries of clones may be prepared using techniques well known in the art and may be screened for particular epithelin-encoding DNAs with nucleotide probes designed from the known amino acid sequence of epithelin 1 or epithelin 2 and/or which are substantially complementary to any portion of the epithelin gene. Full length clones, i.e., those containing the entire coding region of the precursor or mature epithelin desired may be selected for constructing expression vectors.

Alternatively, epithelin-encoding DNAs may be synthesized in whole or in part by chemical synthesis using techniques standard in the art.

Due to the inherent degeneracy of nucleotide coding sequences, other DNA sequences which encode substantially the same or a functionally equivalent amino acid sequence may be used in the practice of the methods of the invention. Such alterations of epithelin nucleotide sequences include deletions, additions or substitutions of different nucleotides resulting in a sequence that encodes the same or a functionally equivalent gene product. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the resides involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

5.1.3.2. CONSTRUCTION OF EPITHELIN EXPRESSION VECTORS

In order to express biologically active, mature or precursor forms of the various epithelins, an expression vector/host system should be chosen which provides not only for high levels of transcription and translation but for the correct processing of the gene product. This may be especially important when employing the entire coding sequence of an epithelin precursor in the expression contructs since the mature forms of the epithelins appear to be derived from larger precursors via cellular processing events.

A variety of animal/host expression vector systems (i.e., vectors which contain the necessary elements for directing the replication, transcription and translation of epithelin coding sequences in an appropriate host cell) may be utilized equally well by the skilled artisan. These include, but are not limited to, virus expression vector/mammalian host cell systems (e.g., cytomegalovirus, vaccinia virus, adenovirus, and the like); insect virus expression vector/insect cell systems (e.g., baculovirus); or nonviral promoter expression systems derived from the genomes of mammalian cells (e.g., the mouse metallothionine promoter). Appropriate host cells include but are not limited to mammilian cells. For example, transient expression of mammalian proteins may be achieved using a COS cell host, while stable expression may be achieved using a CHO cell host.

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g. mouse metallothionine promoter) or from viruses that grow in these cells, (e.g. vaccinia virus 7.5K promoter or Moloney murine sarcoma virus long terminal repeat) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where an entire epithelin gene including its own initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the epithelin coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

Any of the methods previously described for the insertion of DNA fragments into a vector may be used to construct expression vectors containing the epithelin gene of interest and appropriate transcriptional/translational control signals. These methods may include in vitro recombinant DNA techniques, synthetic techniques and in vivo recombinations.

For example, in cases where an adenovirus is used as an expression vector, an epithelin coding sequence may be ligated to an adenoviris transcription/translation control complex, e.g., the late promoter and tripartite leader sequence. This chimeric gene may then be inserted in the adenovirus genome by in vitro or in vivo recombination. Insertion in a non-essential region of the viral genome that is viable and capable of expressing the epithelin in infected hosts. Similarly, the vaccinia 7.5K promoter may be used.

An alternative expression system which could be used to express epithelins is an insect system. In one such system, *Autographa californica* nuclear polyhedrosis virus (AcNPV) is used as a vector to express foreign genes. The virus grows in *Spodoptera frugiperda* cells. An epithelin coding sequence may be cloned into non-essential regions (for example the polyhedrin gene) of the virus and placed under control of an AcNPV promoter (for example the polyhedrin promoter). Successful insertion of an epithelin coding sequence will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed.

Retroviral vectors prepared in amphotropic packaging cell lines permit high efficiency expression in numerous cell types. This method allows one to assess cell-type specific processing, regulation or function of the inserted protein coding sequence.

In addition, a host cell strain may be chosen which modulates the expression of the inserted sequences, or modifies and processes the gene product in the fashion desired. Expression from certain promoters can be elevated in the presence of certain inducers, (e.g. zinc and cadmium ions for metallothionein promoters). Therefore, expression of the genetically engineered epithelins may be controlled. This is important if the protein product of the cloned foreign gene is lethal to the host cell. Furthermore, modifications (e.g. glycosylation) and processing (e.g., cleavage) of protein products are important for the function of the protein. Different host cells have characteristic and specific mechanisms for the post-translational processing and modification of proteins. Appropriate cell lines or host systems can be chosen to ensure the correct modification and processing of the expressed foreign protein.

5.1.3.3. IDENTIFICATION OF TRANSFECTANTS OR TRANSFORMANTS EXPRESSING EPITHELIN GENE PRODUCTS

The host cells which contain the recombinant coding sequence and which express the biologically active, mature product may be identified by at least four general approaches (a) DNA-DNA, DNA-RNA or RNA-antisense RNA hybridiation; (b) the presence or absence of "marker" gene functions; (c) assessing the level of transcription as measured by the expression of epithelin mRNA transcripts in the host cell; and (d) detection of the mature gene product as measured by immunoassay and, ultimately, by its biological activities.

In the first approach, the presence of epithelin coding sequences inserted into expression vectors can be detected by DNA-DNA hybridization using probes comprising nucleotide sequences that are homologous to epithelin coding sequences.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if an epithelin coding sequence is inserted within a marker gene sequence of the vector, recombinants containing that coding sequence can be identified by the absence of the marker gene function. Alternatively, a marker gene can be placed in tandem with the epithelin sequence under the control of the same or different promoter used to control the expression of the epithelin coding sequence. Expression of the marker in response to induction or selection indicates expression of the epithelin coding sequence.

In the third approach, transcriptional activity for an epithelin coding region can be assessed by hybridization assays. For example, polyadenylated RNA can be isolated and analyzed by Northern blot using a probe homologous to the appropriate epithelin coding sequence or particular portions thereof. Alternatively, total nucleic acids of the host cell may be extracted and assayed for hybridization to such probes.

In the fourth approach, the expression of the mature protein product can be assessed immunologically, for example by Western blots, immunoassays such as radioimmunoprecipitation, enzyme-linked immunoassays and the like. The ultimate test of the success of the expression system, however, involves the detection of the biologically active epithelin gene product. Where the host cell secretes the gene product, cell free media obtained from cultured transfectant host cells is assayed for epithelin activity. Where the gene product is not secreted, cell lysates may be assayed for such activity. In either case, biological assays such as the growth inhibition and stimulation assays described herein or the like may be used.

5.1.4. EPITHELIN DERIVATIVES, ANALOGS AND PEPTIDES

The production and use of derivatives, analogues, and peptides related to the epithelins are also envisioned and are within the scope of the invention. Such derivatives, analogues, and peptides which exhibit growth modulatory activity may, like the various epithelins, find applications in the diagnosis, prognosis, and treatment of a wide variety of neoplasias and other growth related diseases. Such derivatives, analogues, or peptides may have enhanced or diminished biological activities in comparison to native epithelins and/or may expand or limit epithelin growth inhibitory activity (GIA)-susceptible cell range and still be within the scope of the invention. Similarly, the production and use of derivatives, analogues, and peptides related to epithelins which exhibit enhanced or diminished growth stimulatory activity (GSA) and/or which expand or limit the range of cells responsive to epithelin GSA may find useful applications including, but not limited to, the treatment of wounds and burns.

Epithelin-related derivatives, analogues, and peptides of the invention may be produced by a variety of means known in the art. Procedures and manipulations at the genetic and protein levels are within the scope of the invention.

At the protein level, numerous chemical modifications could be used to produce epithelin-like derivatives, analogues, or peptides by techniques known in the art, including but not limited to acetylation, formylation, oxidation, specific chemical cleavage by endopeptidases (e.g. cyanogen bromide, trypsin, chymotrypsin, V8 protease, and the like) or exopeptidases, etc.

5.2. ANTI-EPITHELIN ANTIBODIES

Also within the scope of the invention is the production of polyclonal and monoclonal antibodies which recognize epithelins or related proteins.

Various procedures known in the art may be used for the production of polyclonal antibodies to epitopes of epithelins. For the production of antibodies, various host animals can be immunized by injection with an epithelin, or a synthetic epithelin peptide, including but not limited to rabbits, mice, rats, etc. Various adjuvants may be used to increase the immunological response, depending on the host species, including but not limited to Freund's (complete and incomplete), mineral gels (such as aluminum hydroxide), surface active substances (such as lysolecithin), pluronic polyols, polyanions, oil emulsions, keyhole limpet hemocyanins, dinitrophenol, and potentially useful human adjuvants such as BCG (bacille Calmette-Guerin) and *Corynebacterium parvum.*

A monoclonal antibody to an epitope of an epithelin can be prepared by using any technique which provides for the production of antibody molecules by continuous cell lines in culture. These include but are not limited to the hybridoma technique originally described by Kohler and Milstein (1975, Nature 256, 495–497), and the more recent human B-cell hybridoma technique (Kosbor et al., 1983, Immunology Today 4:72) and EBV-hybridoma technique (Cole et al., 1985, Monoclonal Antibodies and Cancer Therapy, Alan R. Liss, Inc., pp. 77–96).

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the two Fab fragments which can be generated by treating the antibody molecule with papain and a reducing agent.

Antibodies to epithelins may find use in the qualitative detection of mature epithelins and their precursor and subcomponent forms, in the affinity purification of epithelin proteins, and in the elucidation of epithelin biosynthesis, metabolism and function. Antibodies to epithelins may also be useful as diagnostic and therapeutic agents.

5.3. BIOLOGICAL PROFILE OF THE EPITHELINS

Applicants' initial cDNA cloning efforts indicate that the epithelin family of growth modulatory proteins is comprised of several structurally similar members. Moreover, it appears that epithelin-encoding mRNA is expressed in several tissue types over a broad range of chordates. Applicants' initial data regarding the structure of epithelin genes from these various chordate sources suggests that the epithelin gene has been in place and has remained remarkably constant for at least 250 million years. The various epithelins appear to be single chain low molecular weight proteins. None of the sequences obtained for the epithelins are significantly homologous to any previously known protein. Interestingly, several of the epithelins contain a region homologous with the active site of phospholipase A2.

Epithelin 1 and epithelin 2 purified from rat kidney tissue are proteins of 56 and 57 amino acids, respectively, sharing 47% amino acid sequence homology and 12 identically positioned cysteine residues. Thus, about one-fifth of the amino acids of both epithelins are cysteines. The positioning of these 12 cysteine residues suggests that, through the formation of disulfide linkages between them, the pattern directs the formation of a "cysteine cage" at the tertiary structural level, perhaps not unlike zinc finger structures. Applicants are not aware of any other protein having this particular, or a closely related, cysteine pattern. This unique cysteine pattern is observed not only in the primary structures of purified epithelins 1 and 2, but also in the structures deduced from the sequences of several epithelin-encoding cDNAs and PCR clones. It appears that this unique cysteine pattern is therefore a distinguishing characteristic of the epithelin family members, and likely plays an important functional role. In addition, some 15 other amino acids are conserved between these two purified epithelins.

A cDNA encoding the complete rat epithelin precursor has been isolated and its nucleotide and deduced amino acid sequences determined, as shown in SEQ ID NOS: 1 and 2, respectively. The rat epithelin precursor comprises a polypeptide of 589 amino acid residues, the amino-terminal 17 residues of which comprise its signal peptide. It appears that at least seven complete and distinct epithelin species are encoded within the rat epithelin precursor gene. The high level of sequence homology between the epithelins encoded by the rat epithelin precursor cDNA can be visualized by the 7.5-fold internal homology generated upon comparison of the rat epithelin precursor sequence to itself, as illustrated in FIG. 18. Composite secondary structure and hydropathy analyses of the rat epithelin precursor are shown in FIG. 19A and FIG. 19B, respectively. Amino acid sequence alignments between the rat, mouse and human epithelin precursors (SEQ ID NO:2,6, and 4, respectively) are shown in FIG. 20A.

Applicants have also isolated the complete human, mouse and rat epithelin precursor DNA sequences (SEQ ID NO:1, 5, and 3, respectively). A composite alignment of these epithelin sequences is illustrated in FIG. 20A. In addition, a number of PCR clones encoding various epithelins of bovine and avian origin have been obtained and the bovine and avian epithelin precursor structures partially determined (SEQ ID NO:7 and 8 (bovine) and SEQ ID NOS:9 and 10 (chicken)). Analysis of the various sequences indicates that the epithelins share, to somewhat different degrees, a distinct structural characteristic defined by the highly conserved cysteine motif (consensus) shown in FIG. 20C. While this consensus sequence appears to be generally conserved among the epithelins, a cysteine core motif of "CCx$_8$CCx$_6$CCx$_5$CC", is almost completely conserved in all epithelin species examined to date, regardless of origin. Exceptions include the first full repeat of the rat epithelin precursor (SEQ ID NO:2) where Cysteine to serine substitutions are present and the motif is "SCx$_9$CCx$_6$SCx$_5$CC". Furthermore, a histidine residue at the 25th position of the core motif also appears to be conserved among the epithelin species. Applicants believe that the core motif is a unique characteristic of all epithelins and, accordingly, intend that the present invention encompass all proteins having this structural feature. FIG. 20B shows the amino acid sequence of human, rat and mouse mature epithelins 1–7 aligned. The sequence represented by FIG. 21C is completely conserved between epithelins 2–7 in these three species. The epithelin 1 sequences diverge from this sequence only slightly.

Applicants have examined RNA from a large number of human and murine tissues and cell lines for the presence of epithelin transcripts, the results of which are sumarized in TABLE I, below.

TABLE I

DISTRIBUTION OF EPITHELIN TRANSCRIPT EXPRESSION IN VARIOUS HUMAN AND MURINE TISSUES AND CELLS

| HUMAN Strong + | Weak + | Negative (using Rat Probe) |
|---|---|---|
| Placenta | Ovary | Brain |
| Colon | Duodenum | Epidermis |
| Kidney Medulla | Thymus | Liver |
| Kidney Cortex | Lung | Pituitary |
| Testis | Kidney | Amnion |
| Adrenal | | Bone Marrow |
| Breast | | Cerebellum |
| CRL 7386 | HBL100 | |
| Caki-1 | HEPM | MCF-7 |
| CRL 1550 | CRO 1572 | HTB27 |
| Caki-2 | HTB132 | T47D |
| HUF | 1477 | CEMA-1 |
| CCL 137 | HSB2 | |
| | U937 | Breast Ca |
| | HTB131 | Wilm's Ca |
| | BT474 | |
| | HTB36 | |

TABLE I-continued

DISTRIBUTION OF EPITHELIN TRANSCRIPT EXPRESSION IN VARIOUS HUMAN AND MURINE TISSUES AND CELLS

MOUSE

| Strong + | Weak + | Negative |
|---|---|---|
| Fetal Intestine | Heart | NONE |
| Placenta | Ovary | |
| Kidney | Thymus | |
| | Pancreas | |
| Brain (Cortex) | Cerebellum | |
| | Lung | |
| | Embryo d15 | |
| | Embryo D6 | |
| | Liver | |
| | Colon | |
| | Duodenum | |
| | Skeletal Muscle | |
| | CCL51 | |
| | CCLS1 (TPA) | |

The biological characteristics of purified epithelin 1 and epithelin 2 are described in some detail in Section 6.4, infra. Both proteins are stable after treatment with 1M acetic acid, 1M ammonium hydroxide, 6M urea, 10 mM sodium metaperiodate, and heating at 56° C. for 30 minutes. The bioactivities of both proteins are sensitive to, inter alia, proteolytic enzymes and reducing agents. It is clear that at least some disulfide linkages in the epithelin structure are essential for bioactivity. It doesnot appear that oligosaccharides and/or lipid moieties are essential for the activity of either epithelin 1 or 2.

Epithelin 1 and epithelin 2 exhibit growth inhibitory activity on, inter alia, human epidermoid carcinoma cells. Applicants' data suggests, however, that epithelin 1 is a more potent inhibitor of cell growth. For example, the calculated specific activity of purified epithelin 1 is nearly ten times that of epithelin 2, and epithelin 1 appears to be some 36 times more potent than epithelin 2 in inhibiting the growth of A431 cells. Moreover, in at least one cell line tested, a human colon carcinoma cell line, epithelin 2 was incapable of triggering the inhibitory effect observed with epithelin 1.

Of additional interest is the functional divergence between epithelin 1 and epithelin 2 with respect to cell growth stimulatory bioactivity. Applicants have demonstrated that epithelin 1, in addition to its growth inhibitory bioactivity, is a potent stimulator of cell growth on several cell lines, leading applicants to conclude that epithelin 1 is a true bifunctional growth modulator. In contrast, applicants' data suggests that epithelin 2 is incapable of triggering a growth stimulatory effect, at least on the cell lines tested.

Perhaps most interesting of all is applicants' further discovery that epithelin 2 specifically antagonizes the stimulatory activities exerted by epithelin 1. Although the functional interrelationship among these and/or other epithelins is not understood at the present time, it is possible that epithelin 2 may function as a control on the stimulatory activity induced by epithelin 1. Applicants speculate that an agonist/antagonist functional relationship among epithelin 1 and epithelin 2, and/or among other members of the epithelin family, may control or otherwise influence the balance between normal and unrestrained cell growth and development. In this regard, cellular homeostatis may be altered or destroyed by the loss of a critical function provided by an epithelin or epithelins involved in such an interrelationship resulting, for example, in unrestrained cell proliferation.

Through the therapeutic use of epithelins, anti-epithelin antibodies, and/or epithelin receptors, cellular homeostasis may be modulated and/or restored.

The ability to express individual motifs from the epithelin precursor will assist in determining whether differential processing releases other active molecules. In order to select candidate effectors or blockers, the sequences of the cysteine-rich motifs shown in FIG. 20A were aligned and cluster analyzed. The results are represented by the dendrogram in FIG. 22. In all cases, the least dissimilar motif is found at the same position within the precursor of the other 2 species. Based on these findings, it is proposed that the primordial epithelin gene underwent a seven-fold replication prior to the divergence of rodents and humans. This analysis also shows that the fifth repeat of the epithelin precursor is most similar to epithelin 1, and is a candidate for having growth stimulatory activity. In addition, the second repeat is most similar to epithelin 2, and is a candidate antagonist of the mitogenic effects of epithelin 1.

The epithelin gene has several intriguing features. The gene's ubiquitous expression suggests it plays a role in the maintenance of normal epithelial cell growth, in contrast to previously described molecules that have a more restricted distribution. The highly repetitive and cysteine-rich structure of the epithelin precursor defines a novel and evolutionarily conserved motif. Furthermore, at least two of these motifs can be proteolytically processed into active growth regulators. This configuration is similar to that of proopiomelanocortin (POMC), a prohormone that is processed in a tissue-specific manner to release a variety of bioactive peptides. (Smith and Funder, 1988, Endocr. Rev. 9:159–79).

The opposing activities of epithelin 1 and 2 on the growth of epithelial cells is reminiscent of other systems where naturally occurring, structurally related molecules act as antagonists or suppressors of the parent molecule. Examples of this include; IL-1ra, an interleukin-1 receptor antagonist (Hannum et al., 1990, Nature 343:336–40; Eisenberg et al., 1990, Nature 343:341–46); Krev-1 (Kitayama et al., 1989, Cell 56:77–84), a protein that suppresses ras induced transformation; and inhibin (Ling et al., 1985, Proc. Natl. Acad. Sci. U.S.A. 82:7217–21), a gonadal protein that opposes the biological effects of activin (Ling et al., 1986, Nature 321:779–82). Further studies to identify cellular receptors for epithelin 1 and 2 are needed to define how these molecules mediate their opposing signals. The finding that both activities are products of the same transcript is provocative. Conceivably, tissue-, spatial-, or temporally-specific processing might provide a unique means of regulating epithelial homeostasis.

5.4. USES OF THE EPITHELINS, EPITHELIN-ENCODING NUCLEIC ACID MOLECULES, ANTI-EPITHELIN ANTIBODIES AND EPITHELIN RECEPTORS

Applicants envision a wide variety of uses for the compositions of the present invention, including diagnostic and/or therapeutic uses of the epithelin proteins, epithelin analogues and derivatives, epithelein-encoding nucleic acid molecules, anti-epithelin antibodies and epithelin receptors.

5.4.1. EPITHELIN PROTEINS

Epithelin proteins, analogues and derivatives, as well as compositions containing them, may be used alone or in combination with each other and/or with other biologically active growth factors, inhibitors, or immunomodulatory agents to regulate the growth and/or development of chordate cells in vivo and in vitro.

Different epithelins and epithelin compositions may be used to achieve different therapeutic objectives. In particular, given the observed functional diversity between epithelin 1 and epithelin 2, applicants envision that these two epithelins may be used for different purposes. However, notwithstanding their functional differences, both epithelin 1 and epithelin 2 may be useful as anti-tumor agents since they both demonstrate the ability to inhibit the growth of neoplastic cells, although applicants' initial data suggests that epithelin 1 may be a more powerful and/or effective tumor inhibitor. The particular combination of epithelins and/or other factors used will depend on the type of target cells involved as well as the particular objective(s) desired.

For in vivo use, the subject compositions may be administered in a variety of ways, including but not limited to, injection, infusion, topically, parenterally, etc. Administration may be in any physiologically acceptable carrier, including phosphate buffered saline, saline, sterilized water, etc. Epithelins and related molecules may also be encapsulated in liposomes and may be conjugated to antibodies which recognize and bind to tumor or cell specific antigens, thereby providing a means for "targeting" the compositions of the invention.

The epithelins may be useful in vivo for inducing terminal differentiation in tumor cells. Such cells have diverted from the ordinary course of cell differentiation characteristic of normal cells and are capable of continued proliferation. Normal cells, in contrast, differentiate into cells which are incapable, under most circumstances, of further cell division. Thus, the ability of the epithelins to reactivate normal cellular differentiation in tumors and, ultimately, to arrest continued tumor growth may find valuable use in tumor therapy regimens.

Epithelins and related derivatives, analogues, and peptides thereof may be used alone or with at least one other anti-proliferative compound, including, for example, an interferon, TFG-β, tumor necrosis factors, etc., in the treatment of neoplastic and other growth related diseases. Carcinomas may also be treated by inducing production of epithelins in the carcinoma cells.

The compounds of the invention may be used in vitro to inhibit the growth of cells or cell lines sensitive to epithelins as distinguished from cells which are not sensitive. In this way, heterogeneous mixtures or cell lines can be freed of undesirable cells, where the undesirable cells are sensitive to epithelin growth inhibitory activity. For example, the compounds of the invention may be used in vitro to eliminate malignant cells from marrow for autologous marrow transplants, and to eliminate or inhibit the proliferation of malignant cells in blood prior to reinfusion.

The most effective concentration of epithelins for inhibiting proliferation of a given cell may be determined by adding various concentrations of epithelins to the tumor cell of interest and monitoring the amount of inhibition of cell proliferation. The most effective concentration of individual inducers and/or combinations of inducers may be determined by monitoring the production of epithelins in the carcinoma cells.

Stimulation of cell growth can be induced by epithelin 1, epithelin 1-like molecules, and, perhaps, by other members of the epithelin family. A wide range of therapeutic applications based on this epithelin bioactivity are envisioned, including but not limited to wound healing and tissue remodeling. Moreover, antibodies capable of neutralizing the epithelin 1-inhibiting activity of epithelin 2 may also be useful in promoting wound healing and tissue remodeling, with or without the coadministration of epithelin 1 or epithelin 1-like molecules.

The compositions of the present invention may also find use in the treatment of human skin diseases involving the proliferation of normal cells, such as psoriasis. Although the pathogenesis of psoriasis is not known, the disease involves rapid epithelial cell proliferation and turnover. The accompanying rapid turnover of keratinocytes alters keratinization, resulting in thickened epidermis and scales characteristic of the disease. Since epithelin 1 stimulates the growth and proliferation of keratinocytes, effective therapy inhibiting this epithelin 1-induced activity may impede the onset and development of the disease. Therefore, compositions capable of inhibiting what may be endogenous or abnormally high levels of epithelin 1 in psoriasis patients may be effective in curing the disease. Applicants have demonstrated that epithelin 2 specifically inhibits the epithelin-I-induced stimulation of keratinocytes. In this regard, epithelin 2-containing compositions may be particularly useful in the treatment of psoriasis. Similarly, antibodies capable of neutralizing epithelin 1 stimulatory activity may be used to inhibit epithelin 1 activity.

Applicants also envision the use of epithelins and epithelin-like molecules for other therapeutic purposes, including but not limited to the modulation of angiogenesis, renal generation, bone resorption, immune responses, synaptic and neuronal effector functions, the arachidonic cascade, and gonadal and reproductive functions.

A number of diagnostic uses of epithelins and related molecules are envisioned. In the practice of the invention, the subject polypeptides may be joined to a label, such as a radioisotope, enzyme, fluorescer, chemiluminescer, enzyme fragment, particle, etc. Such compounds may be used to titrate the number of epithelin receptors on a cell. Identification of epithelin receptors is an indication of potential responsiveness of the cell to the biological effects of epithelins and related molecules. Epithelins, epithelin-related molecules, and/or antibodies thereto may be used in competitive assays for detection of epithelins in media, particularly in physiological media. A wide variety of diagnostic assays known in the art may be used.

The presence and levels of epithelins in body fluids and tissues may directly or inversely relate to the presence and pervasiveness of certain cancers and other growth related diseases. Assays which can detect and/or quantify epithelins may find use in diagnosis and prognosis of growth related diseases.

In addition, malignant cells expressing epithelin receptors may be detected by using labeled epithelins or epithelin-related molecules in a receptor binding assay, or by the use of antibodies to the epithelin receptor itself. Cells may be distinguished in accordance with the presence and density of epithelin receptors, thereby providing a means for predicting the susceptibility of such cells to the biological activities of epithelins.

5.4.2. EPITHELIN-ENCODING NUCLEIC ACID MOLECULES

Epithelin-encoding nucleic acid molecules or fragments thereof may be used as probes to detect and quantify mRNAs encoding epithelins. Assays which utilize nucleic acid probes to detect sequences comprising all or part of a known gene sequence are well known in the art. Epithelin mRNA levels may indicate emerging and/or existing neoplasia as well as the onset and/or progression of other human diseases including but not limited to psoriasis. Therefore, assays which can detect and quantify epithelin mRNA may provide a valuable diagnostic tool.

Anti-sense epithelin RNA molecules may be useful therapeutically to inhibit the translation of epithelin-encoding mRNAs where the therapeutic objective involves a desire to eliminate the presence of a given epithelin. Epithelin 1 anti-sense RNA, for example, could be useful as an epithelin 1 antagonizing agent in the treatment of diseases for which epithelin 1 is a causative agent. Additionally, epithelin anti-sense RNAs may be useful in elucidating epithelin functional mechanisms.

Epithelin-encoding nucleic acid molecules may be used for the production of recombinant epithelin proteins and related molecules, as separately discussed in Section 5.1.3., supra.

6. EXAMPLE: PREPARATION OF PURIFIED EPITHELIN 1 AND EPITHELIN 2 FROM RAT KIDNEY

6.1. PURIFICATION PROCEDURES

6.1.1. ACID ETHANOL EXTRACTION

Rat kidneys were obtained from Pel-Freeze (Rogers, Arkansas). Frozen rat kidneys (430 g wet weight) were suspended in 2370 ml of extraction buffer consisting of 2348 ml ethanol (98%), 19 ml of concentrated HCl, 81.5 mg phenylmethyl-sulfonyl fluoride and 2.8 ml of aprotonin (23 TIU/ml from bovine lung; Sigma Chemical Co.). The tissue was allowed to thaw at 4° C. for 4–6 hours and the mixture was homogenized in a Waring blender. The mixture was stirred at 4° C. overnight, centrifuged at 9,000 rpm in a Sorvall GS-3 rotor for 40 minutes and the supernatant carefully removed (2,200 ml). Chloroform (2,200 ml) and 220 ml of acidified water (375 ml water+7.5 ml of concentrated HCl) was added to the supernatant, the mixture stirred vigorously for approximately one hour, and allowed to stand at room temperature to separate into two phases. The upper aqueous phase was carefully removed and dialyzed against 17 liters of 0.1M acetic acid at 4° C. in No. 3 Spectropore dialysis tubing (molecular weight cut off approximately 3,000). The dialysis buffer was changed three times over a two-day period. The retenate was lyophilized and the lyophilized material (4.55 g), termed "crude extracts", was stored at −20° C. until further use.

6.1.2. PREPARATIVE GEL PERMEATION CHROMATOGRAPHY

A Bio-Sil TSK-250 column (21.5×600 mm) (BioRad) was attached to a high performance liquid chromatography (HPLC) system (Waters). The crude extract (25 mg/ml) was dissolved in 50% acetonitrile/water with 0.1% rifluoroacetic acid (TFA). A 3 ml aliquot of the mixture was injected and elution was performed isocratically with a mobile phase of 50% acetonitrile with 0.1% TFA. The flow rate was 4 ml/min and chart speed was set at 0.25 cm/min. Six ml fractions were collected. The chromatography was performed at room temperature. An aliquot from each fraction was evaporated and assayed in triplicate for growth inhibitory activity (GIA) on A431 human epidermoid carcinoma cells as described in Section 6.2.1., infra. (FIG. 1).

The late eluting minor peak (Fractions 25–28) contained the new activities of interest. Fractions 25–28 from 57 similar runs were pooled, concentrated and lyophilized. The lyophilized material weighed 473 mg and had a total of approximately $1.1 \times 10^5$ GIA units.

6.1.3. REVERSED-PHASE HPLC OF PREPARATIVE TSK-250 FRACTIONS

The lyophilized fractions (Section 6.1.2., supra) were dissolved in 240 ml of 0.1% TFA in water; the mixture was centrifuged, and the supernatant was carefully removed. The final volume was about 250 ml. 125 ml of this mixture was isocratically injected onto a preparative Partisil 10 ODS-3 column (10 micron, 2.2×25 cm; Whatman) attached to a HPLC system. The flow rate was set at 4 ml/min. Once the sample had passed onto the column, the column was washed with 150 ml of 0.1% TFA in water. The linear gradient was generated between the primary solvent, 0.1% TFA in water, and the secondary solvent, acetonitrile containing 0.1% TFA. The gradient conditions were: 0 to 45% in 270 minutes and 45 to 100% in 45 minutes. 14 ml fractions were collected and aliquots of each fraction were assayed for GIA. Four broad peaks of activity were seen (FIG. 2). A second run was performed as described above. Two early eluting peaks, peak a and peak b, contained epithelin 2 and epithelin 1, respectively, and they were further purified and characterized. The further purifications of epithelin 1 and epithelin 2 are described separately below.

6.1.4. FURTHER PURIFICATION OF EPITHELIN 1 BY REVERSED-PHASE AND GEL PERMEATION HPLC

Fractions 55–59 (FIG. 2) from two runs were pooled and diluted twofold with 0.1% TFA in water. The mixture was isocratically injected onto a semi-preparative $\mu$-Bondapak-C18 column (7.8×300 mm, Waters) at a flow rate of 2 ml/min at room temperature. The linear gradient conditions between primary solvent, water with 0.1% TFA, and the secondary solvent, acetonitrile with 0.1% TFA, were 0 to 18% in 1.8 minutes, 18 to 18% in 20 minutes, 18 to 34% in 240 minutes, and 34 to 100% in 10 minutes. The flow rate was 2 ml/min throughout the gradient; 7 ml fractions were collected. Aliquots were taken and assayed for GIA. Two peaks of activity were observed eluting at acetonitrile concentrations of approximately 24% and 25%, respectively (FIG. 3).

Fractions 30–34 were pooled. 45 ml of 0.1% TFA in water was added to the pooled fraction. The mixture was isocratically applied onto a $\mu$-Bondapak-CN column (3.9×300 mm, Waters) at a flow rate of 1 ml/min at room temperature. The gradient conditions were 0 to 10% in 1 minute, 10 to 10% in 19 minutes, 10 to 30% in 200 minutes, and 30 to 100% in 7 minutes. The flow rate was 0.5 ml/min and 1.5 ml fractions were collected. Most of the activity emerged from the column at about 21.5% acetonitrile concentration (FIG. 4).

Fractions 36–43 were pooled and diluted with 0.1% TFA/H$_2$O to a final volume of 115 ml and chromatographed exactly as described for fractions 30–34, above. Most of the activity eluted from the column in two peaks, eluting at approximately 22.5% and 23.5% acetonitrile (FIG. 5).

Fractions 51 and 52 (FIG. 4) were individually concentrated, using a speed-vac concentrator (Savant), to a volume of about 70 $\mu$l to which an equal volume of acetonitrile containing 0.1% TFA was added. This 140 $\mu$l sample was injected onto two Bio-Sil TSK-250 columns (7.5×300 mm each, Bio-Rad) arranged in tandem. The elution was performed isocratically with a mobile phase of 50% acetonitrile/H$_2$O with 0.1% TFA at room temperature. The flow rate was 0.4 ml/min and chart speed was 0.25 cm/min; 0.4 ml fractions were collected and aliquots were assayed for GIA. The chromatographic profiles of fractions 51 and 52 are shown in FIG. 6A and FIG. 6B, respectively.

Fractions 44 and 45 (FIG. 5) were individually concentrated to 70 μl and then subjected to gel permeation chromatography as described above. The chromatographic profiles are given in FIG. 7.

6.1.5. FURTHER PURIFICATION OF EPITHELIN 2 BY REVERSED-PHASE AND GEL PERMEATION HPLC

Fractions 50–54 (FIG. 2) from two runs were pooled and diluted twofold with 0.1% TFA/H$_2$O. The mixture was applied onto a semi-preparative μ-Bondapak-C18 column (7.8×30 mm, Waters) at a flow rate of 2 ml/min. The linear gradient conditions between primary solvent, water with 0.1% TFA, and the secondary solvent, acetonitrile with 0.1% TFA, were 0 to 18% in 1.8 minutes, 18 to 18% in 20 minutes, 18 to 34% in 240 minutes, and 34 to 100% in 10 minutes. The flow rate was 2 ml/min throughout the gradient; 7 ml fractions were collected. Aliquots were taken and assayed for GIA. The chromatographic profile is shown in FIG. 8. The major peak of activity eluted at approximately 20.5% acetonitrile concentration.

Fractions 18–23 were pooled and diluted with 0.1% TFA/H$_2$O to a final volume of 110 ml. The mixture was applied onto a μ-Bondapak-CN column (3.9×300 mm, Waters) at a flow rate of 1 ml/min at room temperature. The gradient conditions were 0 to 10% in 1 minute, 10 to 10% in 19 minutes, 10 to 30% in 200 minutes, and 30 to 100% in 7 minutes. The flow rate was 0.5 ml/min; 1.5 ml fractions were collected. The activity emerged from the column at an acetonitrile concentration of about 18% (FIG. 9).

Fractions 36–38 (FIG. 8) were individually concentrated to approximately 70 μl, to which an equal volume of acetonitrile containing 0.1% TFA was added. This 140 μl sample was applied onto two Bio-Sil TSK-250 columns (7.5×300 mm each, Bio-Rad) attached in tandem. The elution was performed isocratically with a mobile phase of 50% acetonitrile/H$_2$O with 0.1% TFA. The flow rate was 0.4 ml/min; 0.4 ml fractions were collected and aliquots were assayed for GIA. The chromatographic profiles of fractions 36, 37 and 38 are shown in FIG. 10A, 10B and 10C, respectively.

Figure 10A:
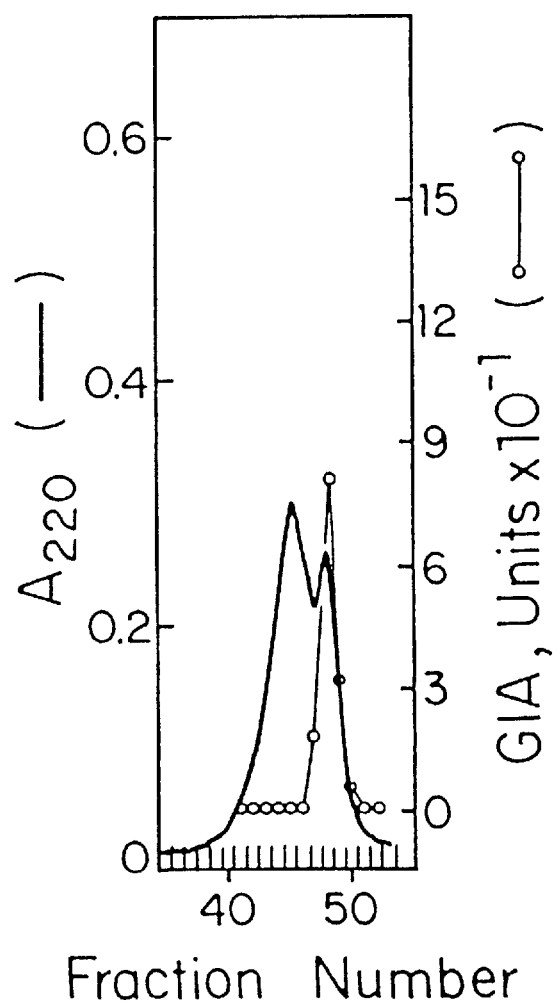
Figure 10B:
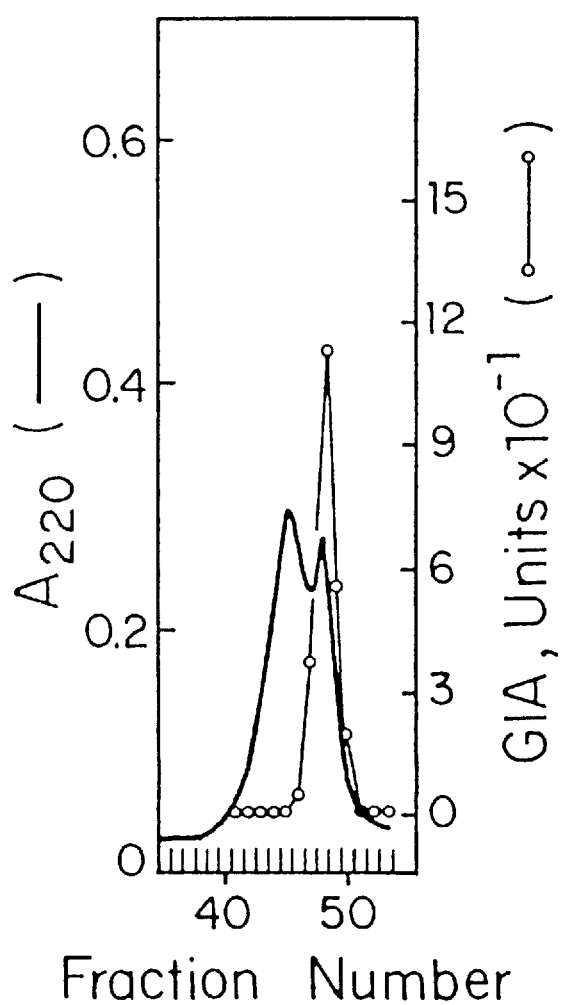
Figure 10C:
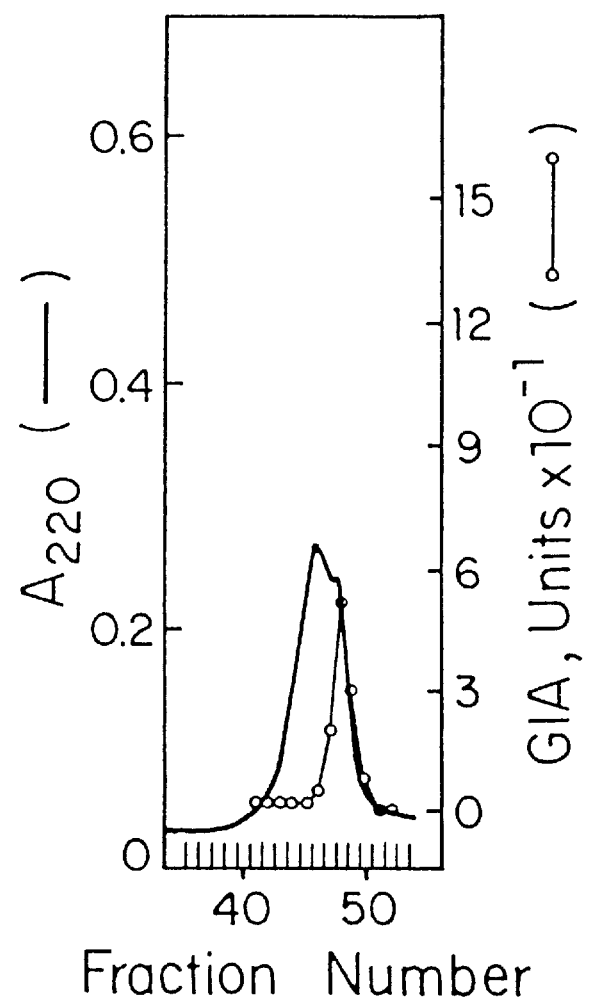
Figure 10D:
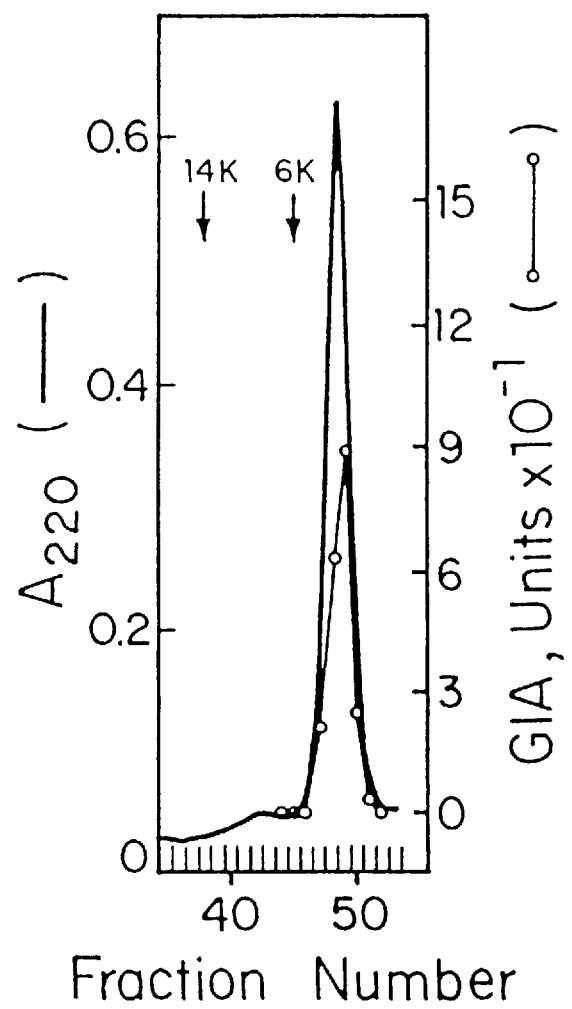

Fractions 48 and 49 from FIG. 10A–C were pooled and concentrated to about 70 μl and then subjected to gel permeation chromatography as described above. The rechromatographic profile is presented in FIG. 10D.

6.2. BIOASSAYS

6.2.1. CELL GROWTH INHIBITORY ACTIVITY USING $^{125}$I-DEOXYURIDINE INCORPORATION INTO DNA

The cell growth inhibitory activity (GIA) assays were performed in flat-bottom 96 well plates (Falcon 3072). Human epidermoid carcinoma of vulva cells (A431) were used as test cells for GIA. 3.5×10$^3$ cells in 50 μl of test medium (DMEM supplemented with 5% heat inactivated fetal bovine serum (FBS), penicillin/streptomycin (PS) and glutamine) were placed in all wells except peripheral wells. The peripheral wells received 50 μl PBS. Three hours later, 50 μl of test sample in test medium was added to each well, while control wells received only 50 μl of test medium. Three wells were used for each concentration of test sample. Plates were incubated at 37° C. for 2–3 days. Then, 100 μl of a solution of $^{125}$I-iodo-2'-$^{125}$I-deoxyuridine ($^{125}$I-IUdR, 4Ci/mg-0.5 mCi/ml, 2 μl/ml in test medium) was added to each well and plates were incubated at 37° C. After 4–6 hours, the medium was aspirated from the wells, which were then washed once with 200 μl PBS. Then, 200 μl methanol was added to each well, plates were incubated for 10 minutes at room temperature, and the methanol was removed by aspiration. 200 μl of 1M sodium hydroxide was added to each well, the plates were incubated for 30 minutes at 37° C. Sodium hydroxide was removed with titertek plugs (Flow Labs). The plugs were transferred into 12×75 mm plastic tubes and counted in a gamma counter to quantify $^{125}$I-IUdR incorporation.

6.2.2. CELL GROWTH INHIBITORY AND STIMULATORY ACTIVITY ASSAYS USING MURINE KERATINOCYTES

Balb/MK cells were plated at 1×10$^4$ cells per well in 1 ml of low calcium medium (Weissman and Aaronson, 1983, Cell 32:599–606; Carpenter and Zendegut, 1985, Anal. Biochem. 153:279–282) in 24-well Costar plates and incubated at 37° C. for 4–6 hours. Then media were removed and replaced with 1 ml of medium containing various concentrations of the test compound in triplicate. The control wells received only medium without any test material. The plates were incubated at 37° C. for 4 days, then medium was removed, wells were rinsed two times with 1 ml of phosphate-buffered saline, and the cells were detached with trypsin-EDTA and counted.

Balb/MK cells were also used as indicator cells in 96 well plates to assess the growth inhibitory activity (GIA) or growth stimulatory activity (GSA) of a test material using $^{125}$I-deoxyuridine incorporation into DNA as described in the previous section.

6.2.3. SOFT AGAR COLONY ASSAY

A 0.38 ml base layer of 0.5% agar (Agar Noble; Difco Laboratories, Detroit, Mich.) in DMEM containing 10% heat inactivated FBS was added to 24 well Costar tissue culture plates. 0.38 ml of 0.3% agar containing the same medium-FBS mixture, 6–12×103 test cells, and the test proteins at various concentrations were overlaid on the basal layer of agar. The plates were incubated at 37° C. in a humidified atmosphere of 5% CO$_2$ in air. Colonies were enumerated unfixed and unstained, and the number of colonies was scored between days 7 and 10. Colonies were defined as a cluster of at least eight cells.

6.3. PRIMARY STRUCTURE DETERMINATIONS

6.3.1. REDUCTION AND S-PYRIDYLETHYLATION

Protein (10–20 μg) was dried in a 1.5 ml microfuge polypropylene tube, suspended in 100 μl of 3M urea in 0.05M Tris-HCl, pH 7.5. Then, 4 μl of 2-mercaptoethanol was added to the mixture, the contents were mixed, flushed with nitrogen, and incubated at 25° C. After 2.5 hours, 4.5 μl of freshly distilled 4-vinylpyridine was added to the mixture, the tube was again flushed with nitrogen and incubated for 2 hours at 25° C. The reaction mixture was acidified to pH 2.0 with 10% TFA. S-pyridylethylated protein was purified by reversed phase HPLC using a Partisil 5 ODS-3 column (4.6×100 mm, Whatman). The concentration of acetonitrile was increased linearly (1%/min) during 55 minutes at a flow rate of 1 ml/min. The primary solvent was 0.1% TFA/H$_2$O. S-pyridylethylated-epithelin 1 (SPE-Epithelin 1) and SPE-Epithelin 2 eluted at about 25% and 23% of acetonitrile, respectively, approximately 2–3% higher acetonitrile concentrations than the untreated epithelins.

6.3.2. ENZYMATIC CLEAVAGE OF SPE-EPITHELIN 1 AND SPE-EPITHELIN 2

Cleavage with endopeptidase Lys-C and TPCK-trypsin was performed in 60 µl of 0.1M Tris-acetic acid buffer, pH 8.0 at 25° C. for 16 hours. The enzyme/substrate ratio was 1 to 5 (w/w). Endopeptidase-Arg and S. aureus V8 protease digestions were done in 80 µl of 0.05M Tris-HCl, pH 8.0, 0.1M ammonium-bicarbonate at 37° C. for 16 hours. The enzyme/substrate ratio was again 1 to 5.

6.3.3. PEPTIDE ISOLATION

Peptides were separated on a reversed phase HPLC C18 column (4.6×100 mm, Whatman) attached to a HPLC system (Waters). Acidified sample (pH 2.0) was applied onto a column equilibriated with 0.1% TFA.(primary solvent) at a flow rate of 1 min/ml and the column was further washed with about 15 ml of 0.1% TFA. Linear gradients were used between the primary solvent and the secondary solvent (acetonitrile with 0.1% TFA). The gradient conditions were 0 to 50% in 125 minutes at a flow rate of 0.5 ml/min.

6.3.4. AMINO ACID ANALYSIS

Dried samples were hydrolyzed with constant boiling HCl (5.7M, Pierce) containing 1% (v/v) phenol under reduced pressure in a Teflon-sealed glass hydrolysis bulb (Pierce) at 105° C. for 16 hr. The hydrolysates were dried in a Speed Vac concentrator (Savant Instruments) and derivitized with phenylisothiocyanate for 20 minutes at room temperature. Phenylthiocarbamyl amino acid derivatives were analyzed by reversed phase HPLC on a Octadecyl column (4.5×250 mm, IBM). The linear gradient was performed between primary solvent 0.15M sodium acetate pH 6.4, 0.05% triethylamine titrated to pH 6.4 with acetic acid and the secondary solent 60% acetonitrile at a flow rate of 1 ml/min at 38° C.

6.3.5. AMINO ACID SEQUENCE DETERMINATION

Peptide sequences were determined with an Applied Biosystem model 475 gas phase sequencer as described (Hewick et al., 1981, J. Biol. Chem. 256:7990–7997). Three precycles of Edman degradation were performed prior to sample application for each run. 25% TFA was used to convert the Triazoline derivatives to phenylthiohydantoin amino acids. Identification of phenylthiohydantoin amino acids was carried out, on-line, on a Model 120A PTH analyzer (Applied Biosystem) as described (Hunkapiller and Hood, 1983, Science 219:650–659).

6.3.6. TRICINE-SODIUM DODECYL SULFATE-POLYACRYLAMIDE GEL ELECTROPHORESIS

Proteins were analyzed on tricine/sodium dodecyl sulfate/polyacrylamide slab gels (normal or mini Bio-Rad system) by the method of Schager and Gebhard, 1987, Biochem. 166:368–379. Proteins were detected by silver staining (Wray et al., 1981, Anal. Biochem. 118:197–203).

6.4. CHARACTERISTICS OF THE EPITHELINS 1 AND 2

6.4.1. PHYSICAL AND CHEMICAL PROPERTIES

Epithelin 1 and epithelin 2 are resistant to treatment with 1M acetic acid, 1M ammonium hydroxide, 6M urea, 0.01M sodium metaperiodate, to heating at 56° C. for 30 minutes, and to treatment with various glycosidases or lipases. However, epithelin activity was sensitive to reduction, to reduction and 4-vinylpyridine treatment, and to digestion with proteinases such as trypsin, endoproteinase Lys-C, and endoproteinase Glu-C (V8). These results suggest that these factors are proteins containing cysteines in disulfide linkage (s) that are essential for biological activity. These proteins do not contain oligosaccharides and/or lipid moieties that are obligatory for biological activities.

6.4.2. PURIFICATION OF EPITHELIN 1 AND EPITHELIN 2 AND CERTAIN PHYSICAL PROPERTIES

Summaries of the purification of epithelin 1 and epithelin 2 are presented in Table I and Table II, respectively. Both factors were purified to apparent homogeneity by a similar six-step protocol. The early step fractions contain a multiple of growth inhibitory activities on A431 cells. Epithelins 1 and 2 constitute only a very minor fraction of total GIA in early fractions, making it very difficult to quantitate their specific activities at early stages of purification. The specific activity of purified epithelin 1 was about $2.1 \times 10^4$ units/mg protein, whereas purified epithelin 2 had a much lower specific activity of $3.8 \times 10^3$ units/mg protein.

TABLE II

Summary of Purification of Epithelin 1 (GIA)

| Fraction | Protein µg | GIA Units[1] | Specific Activity Units/mg | Yield % |
|---|---|---|---|---|
| Crude | 4,550,000 | 1,283,100[2] | 282 | — |
| Prep TSK-250 | 473,000 | 112,200[2] | 237 | — |
| Prep. ODS (b) | 17,600 | 14,100 | 801 | 100 |
| Semi Prep. C18 | | | | |
| 1b | 1,510 | 2,080 | 1,377 | 14.8 |
| 2b | 3,460 | 5,460 | 1,578 | 38.7 |
| Anal. Cyano | | | | |
| 1b | 60 | 713 | 11,889 | 3.4 |
| 2b | 73 | 1,190 | 16,301 | 8.4 |
| Anal. Tsk-250 | | | | |
| 1b | 41 | 845 | 20,609 | 6.0 |
| 2b | 62 | 1,305 | 21,048 | 9.3 |

[1] One unit of GIA is the amount of factor required to inhibit $^{125}$I-labeled deoxyuridine incorporation into A431 cells by 50%.
[2] Other growth inhibitory activities are present in these fractions. These values include all activities.

TABLE III

Summary of Purification of Epithelin 2 (GIA)

| Fraction | Protein µg | GIA Units[1] | Specific Activity Units/mg | Yield % |
|---|---|---|---|---|
| Crude | 4,550,000 | 1,283,100[2] | 282 | — |
| Prep TSK-250 | 473,000 | 112,200[2] | 237 | — |
| prep. ODS (b) | 24,500 | 9,567 | 432 | 100 |
| Semi Prep. C18 | 4,760 | 1,190 | 250 | 12.4 |
| Anal. Cyano | 169 | 460 | 2,741 | 4.8 |
| Anal TSK-250 | 37 | 141 | 3,810 | 1.5 |

[1] One unit of GIA is the amount of factor required to inhibit $^{125}$I-labeled deoxyuridine incorporation into A431 cells by 50%.
[2] Other growth inhibitory activities are present in these fractions. These values include all activities.

The molecular weight of epithelin 1 and eipthelin 2, as determined by gel permeation chromatography on TSK-250 columns, was ~4,500 and ~3,700, respectively (FIGS. 6, 7 and 10). SPE-epithelin 1 or 2 exhibited a molecular weight of ~13,000 by similar gel permeation chromatography.

FIG. 11 shows an analysis of epithelin 1 and epithelin 2 in an 18% polyacrylamide gel under reducing conditions. Epithelin 1 and epithelin 2 migrated in the gel as single bands with median relative molecular weights of about 5,500 and 6,000, respectively. Similar results were obtained when proteins were electrophoresed under nonreducing conditions. Thus, epithelins are single chain, low molecular weight proteins.

6.4.3. CHEMICAL STRUCTURE OF EPITHELIN 1 AND EPITHELIN 2

The amino acid sequences of epithelin 1 and epithelin 2 were deduced from microsequence analysis of S-pyridylethylated proteins, and fragments generated by endoproteinase Lys-C, *Staphylococcal aureus* V8 and TPCK trypsin. The amino acid sequences of epithelin 1 and epithelin 2 are presented in FIG. 12.

The protein sequences of epithelin 1 and epithelin 2 were compared with all proteins in the National Biomedical Research Foundation data base (release 22), Genetic Sequence Data Bank (Bolt Beranek and Newman, Los Alamos National Laboratory; release 61) and the European Molecular Biology Laboratory data base (release 20). These computer aided searches revealed that both proteins are novel and do not share any significant homology to any protein in the three data bases.

Epithelin 1 and epithelin 2 are single chain polypeptides of 56 and 57 amino acid residues, respectively, having calculated molecular weights of 6060 and 6094, respectively. Epithelin 1 and epithelin 2 share 47% homology at the amino acid level. Both proteins contain 12 cysteine residues with four double cysteine residues. Thus about 21% of amino acid residues in both proteins are cysteines. Moreover, the spacing of single cysteine residues and double cysteine residues in epithelin 1 and epithelin 2 is identical. Although the number or position of intrachain disulfide bonds in these proteins is not presently known, a similar or identical pattern is expected. Both proteins also contain about 13% hydroxy amino acids (serine and threonine together). The amino acid alignment of epithelin 1 and epithelin 2 is shown in FIG. 12. In addition the conservation of cysteine residues, 15 other residues are conserved between epithelin 1 and epithelin 2.

The hydropathy profiles of epithelins 1 and 2 are presented in FIG. 13. The hydropathy profile of epithelin 1 exhibits some similarity to that of epithelin 2, although epithelin 2 appears to be more hydrophilic than epithelin 1.

6.4.4. BIOLOGICAL PROPERTIES OF EPITHELIN 1 AND EPITHELIN 2

The inhibition of $^{125}$I-deoxyuridine incorporation into DNA of human epidermoid carcinoma A431 cells by different concentrations of purified epithelin 1 and epithelin 2 is given in FIG. 14. A 50% inhibition of DNA synthesis was seen at 12.8 ng/well of epithelin 1 and 450ng/well of epithelin 2. Thus, a 50% inhibition occurred at approximately 21 nM concentration of epithelin 1 and approximately 0.75 µm concentration of epithelin 2. Epithelin 1 is therefore about 36 times more potent than epithelin 2 in this assay.

The effect of epithelin on the incorporation of $^{125}$I-deoxyuridine into DNA of various tumor and non-tumor human cell lines, as well as several non-human cell lines, was investigated. Epithelin 1 (20 ng/ml, maximum dose tested) slighly inhibited the growth of human colon carcinoma cell line HCT 116, while epithelin 2 (270 ng/ml, maximum dose tested) did not show any effect on this cell line. Both proteins significantly inhibited the $^{125}$I-deoxyuridine incorporation into DNA of mink lung CCL 64 cells and monkey kidney COS1 cells. Neither protein exhibited any significant effect on human fibroblasts and several other human tumor cells at the maximum dose tested (20 ng/ml for epithelin 1 and 270 ng/ml for epithelin 2).

The effects of various concentrations of epithelin 1 and epithelin 2 on the incorporation of $^{125}$I-deoxyuridine into DNA of murine keratinocytes (Balb/MK cells) was investigated. Data are presented in FIG. 15A. Epithelin 1 stimulated the $^{125}$I-deoxyuridine incorporation in a dose-dependent manner, while epithelin 2 did not show any significant effect. However, epithelin 2 inhibited epithelin 1 elicited incorporation of $^{125}$I-deoxyuridine incorporation to Balb/MK cells (FIG. 15B). In this regard, a 50% inhibition was observed at ~21 nM epithelin 2. Thus, epithelin 2 antagonizes the effect of epithelin 1 in this system.

The continued growth of a murine keratinocyte cell line, Balb/MK, is dependent on EGF, TGFα or amphiregulin (AR). Balb/MK cells did not proliferate in the absence of EGF or epithelin 1 (FIG. 16A), whereas epithelin 2 did not exhibit any significant effect on the growth of these cells. However, epithelin 2 inhibited the epithelin 1-induced growth of Balb/MK cells in a dose-dependent manner (FIG. 16B); a 50% inhibition was observed at ~7 nM epithelin 2. EGF or TGFα induces anchorage-independent growth of rat kidney cells NRK-SA6 in the presence of TFGβ (Roberts et al., 1981, Proc. Natl. Acad. Sci. USA 78:5339–5344). Like EGF, epithelin 1 induced the anchorage-independent growth of NRK cells in a dose-dependent manner (FIG. 17), while epithelin 2 did not. Epithelin 2 (at a concentration of ~85 nM) inhibited about 50% of the epithelin 1-induced colony formation in soft agar. Furthermore, epithelin 1, but not epithelin 2, exhibited mitogenic activity on NRK cells in monolayer.

Neither epithelin 1 nor epithelin 2 significantly affected the binding of $^{125}$I-EGF to its receptors, suggesting that the epithelins do not mediate their biological effects through EGF receptors.

7. EXAMPLE:

cDNA CLONING OF THE EPITHELIN PRECURSOR AND TRANSIENT EXPRESSION OF PRECURSOR AND MATURE FORMS

7.1. PCR cDNA CLONING

Two pools of degenerate oligonucleotides were synthesized based on the peptide sequences KTQCPDD and HCCPQDT from epithelin 2 (the pools contained 256 and 128 degenerate oligonucleotides in the sense and antisense orientation, respectively). These oligonucletides were used as primers in a 40 cycle PCR amplification with a single stranded cDNA template derived from rat kidney RNA primed with XSCT17, an oligonucleotide containing a $T_{17}$ track on its 3'-end (Plowman et al, 1990, Proc. Natl. Acad. Sci. U.S.A. 87:4905–08). An oligonucleotide probe, based on the epithelin 2 sequence KYGCCPMP (256 fold degenerate 23-mer), was labeled with [γ-$^{32}$P]ATP and used to screen the PCR products.

Hybridization of this probe to a Southern blot of the PCR products revealed two major bands of 120 base pairs (bp)

and 600 bp, and a minor band of 325 bp. These fragments were subcloned and sequenced, revealing that they all had a common 5' end encoding epithelin 2. The 325 bp fragment had an open reading frame that encoded both epithelin 1 and 2, whereas the 600 bp band extended further 3' and contained an additional copy of the cysteine-rich motif. Therefore, epithelin 1 and 2 appear to be tandemly arranged products of a single transcript. These same PCR primers were used to isolate similar fragments of the epithelin precursor from human, bovine, mouse, and chicken cDNA, demonstrating strong evolutionary conservation of the cysteine-rich motif.

The complete epithelin cDNAs were obtained from rat, mouse, and human sources by using a PCR protocol to isolate the 5' and 3' ends of messages that have a known central sequence, and by screening λgt10 libraries. In particular, a PCR strategy with exact epithelin primers oriented in the 3' and 5' directions in combination with primers that anneal to the natural poly(A) tail, or a synthetic poly(A) track added onto the 5' extended cDNA was employed (Plowman et al., 1990, Proc. Natl. Acad. Sci. U.S.A. 87:4905–08). A rat kidney cDNA library was constructed in λgt10 (Plowman et al., 1990, Mol. Cell Biol. 10:1969–81), and a full length rat epithelin cDNA was isolated by screening 2.0×105 recombinants with PCR generated epithelin probes. These probes were also used to obtain the mouse epithelin gene from a mouse T-cell genomic library (Stratagene, La Jolla, Calif.). Several PCR-generated clones, rat cDNA clones, and the mouse genomic clones were sequenced on both strands by using T7 polymerase with oligonucleotide primers (Tabor and Richardson 1987, Proc. Natl. Acad. Sci. U.S.A. 84:4767–71.

The composite sequence of the rat epithelin cDNA (SEQ ID NO:1) is 2150 bp long, which closely approximates the 2.3 kilobase transcript seen by northern analysis with rat kidney mRNA. The sequence predicts a 589-residue preprotein with a 30 bp 5'-untranslated region and a 343 bp 3'-untranslated region. The first AUG is followed by an N-terminal hydrophobic signal peptide of 16 amino acids and the 573 amino acid mature epithelin precursor with a predicted $M_r$ of 61,597. The precursor has no transmembrane domain, 3 potential N-linked glycosylation sites, and 88 cysteine residues. The epithelin precursor has a highly repetitive organization (FIG. 18) containing 7 tandem copies of a 55–57 amino acid consensus motif: $VXCX_{5-6}CX_5CCX_8 CCX_6CCXDX_2HCCPX_4CX_{5-6}CX_2$. Two of the repeats represent the known active molecules, epithelin 1 and 2. The predicted amino acid sequences of the mouse and human epithelin precursors contain 589 and 593 residues, respectively, and exhibit 86% (mouse) and 75% (human) sequence identity with the rat protein (FIG. 20A). Additional isoforms of epithelin may also exist, since one rat cDNA clone has a deletion of 234 bp (FIG. 20A, amino acids 398–475), maintained the reading frame, and generated a chimeric motif. This deletion is likely the result of alternative splicing since its boundaries map precisely to the location of exon-intron junctions in the mouse epithelin gene.

Comparison of the epithelin sequence with available protein and DNA sequence databases reveals three regions with homology to known proteins. The first 41 amino acids following the signal sequence of the epithelin precursor contains 6 cysteine residues arranged in a pattern similar to the N-terminal half of the other seven cystein-rich motifs. The sequence CPDGQFCPVACC is completely conserved between human, rat and mouse epithelins, and conforms to a consensus pattern present in a family of snake toxins (Dufton, 1984, J. Mol. Evol. 20:128–34). A second region of homology exists within three of the cystein-rich motifs of rat epithelin ($CCX_2HX_2C$), and conforms to a consensus surrounding an active site of phospholipase A2 (Gomez et al., 1989, J. Eur. J. Biochem. 186:23–33). Finally, an extended homology exists between the 12 cysteine motif of epithelin and the C-terminal regulatory domain of a tomato thiol protease (FIG. 20D). This noncatalytic domain has been hypothesized to regulate the protease activity by binding to heavy metals. The alternating cysteine and histidine residues in the epithelin precursor is reminiscent of metal-binding domains of a variety of proteins, although the epithelin motif does not conform to that of any known metal-binding consensus. Northern analysis demonstrates that the 2.3 kilobase epithelin transcript is ubiquitously expressed, and is predominant in the adult kidney, placenta, heart, duodenum, colon, and cerebral cortex. In addition, it is present in a wide variety of epithelial tumor cell lines. Southern analysis indicates that the epithelin precursor is encoded by a single copy gene. These results suggest a post-transcriptional mechanism for the generation of active molecules from the epithelin precursor.

7.2. EXPRESSION IN COS CELLS

The biochemical properties of rat epithelin was determined by inserting its complete coding sequence into an expression vector under the control of the cytomegalovirus immediate-early promoter (Seed and Aruffo, 1987, Proc. Natl. Acad. Sci. U.S.A. 84:3365–69). Specifically, a 1.6 kb fragment containing the complete rat epithelin coding sequence was inserted into a cDM8 based expression vector, generating the expression vector crEPN1.6. A similar construct, crEPN1.4, was prepared by insertion of a 1.35 kb fragment from an epithelin cDNA that has a single exon deletion, thereby eliminating amino acids 398–475. The secretion plasmids, cβrEPN1 and cβrEPN2, were constructed by ligating a synthetic simian TGF-β1 signal sequence (SEQ ID NO:11) contained on the oligonucleotides

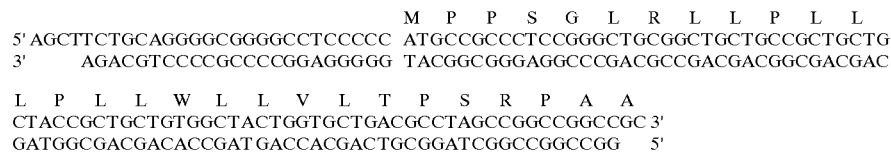

respectively, and PCR generated SacII-XbaI fragments containing the coding sequence of epithelin 1 and 2 into the cDM8SII plasmid digested with HindIII and XbaI. cDM8SII is a modified cDM8 vector, where the unique SacII site has been eliminated with Klenow. The new SacII site places a final glycine of the signal peptide in frame with the epithelin coding sequence. The expression plasmids were grown in competent MC1061/P3 bacteria, and introduced into COS-1 cells using the DEAE-dextran method (Seed and Aruffo, 1987, Proc. Natl. Acad. Sci. U.S.A. 84:3365–69). Forty-eight hours after transfection, the cells were washed with phosphate buffered saline, and labeled for 16 hours in serum free MEM (4 ml per 100 mm plate) supplemented with 250μCi/ml 35S-cysteine (1100 Ci/mmole, New England Nuclear). Labeled supernatants were dialyzed against 0.1N acetic acid, dried, and 1 ml equivalents run on 10% or 15% SDS-polyacrylamide gels.

The transiently expressed protein was readily detected by SDS-PAGE analysis of $^{35}$S-cysteine labeled supernatants. The recombinant protein had a molecular mass of about 75K, slightly more than the predicted 62K, possibly due to glycosylation (FIG. 21A, lane 1). A similar construct encoding an epithelin isoform, but lacking an exon in the C-terminal region, migrated with average $M_r$ of 68K, commensurate with the deletion of 78 amino acids. There was no evidence of the precursor being processed into smaller forms. To express the mature recombinant epithelin 1 and 2 proteins, their coding regions were placed into an expression vector behind a synthetic signal peptide sequence (cβrEPN1 and cβrEPN2, respectively), which resulted in secretion of the 6K proteins from COS cells (FIG. 21B). The cells transfected with these constructs were growth inhibited and exhibited an altered morphology with many cells showing a signet ring appearance, compared with the intact monolayer seen on a mock transfection. Supernatant from the cβrEPN1 transfection was partially purified on a Bio-Sil TSK-250 column (Shoyab et al., 1990, 87:4905–09) and fractions were assayed for growth inhibitory activity (GIA) on A431 cells. These cells secreted active epithelin 1 (approximately 25 GIA units/100 mm plate) whereas the supernatant from mock transfected cells had no detectable activity (one GIA unit corresponds to the amount of material required for 50% inhibition of cell growth).

Epithelin 1 has an inhibitory effect on A431 cells and it acts as mitogen on several normal epithelial cell lines (See Section 6., supra). In addition, epithelin 1 can induce anchorage-independent growth of rat kidney fibroblasts in the presence of transforming growth factor β (FIG. 17). In contrast, epithelin 2 has no effect on the growth of rodent keratinocytes or fibroblasts and it opposed the mitogenic effects of epithelin 1 (in a dose dependent manner) in both of these systems (FIG. 17). The unprocessed epithelin precursor had no activity in any of these assays. Perhaps the intact precursor serves an entirely different role than the processed forms, such as chelating metal ions, or regulation of proteases and phospholipases.

What is claimed is:

1. A method of inhibiting the growth of neoplastic epidermoid cells comprising contacting the neoplastic epidermoid cells with an amount of epithelin 1 effective at inhibiting epidermoid neoplastic cell growth.

2. The method of claim 1 wherein the epithelin 1 is human epithelin 1 having the amino acid sequence as depicted in SEQ ID NO:4 from about amino acid residue numbers 282 to 337.

3. The method of claim 1 wherein the epithelin 1 is rat epithelin 1 having the amino acid sequence as depicted in SEQ ID NO:2 from amino acid residue numbers 280 to 335.

4. The method of claim 1 wherein the epithelin 1 is mouse epithelin 1 having the amino acid sequence as depicted in SEQ ID NO:6 from amino acid residue number 280–335.

5. A method of treating epithelial neoplasia in an animal comprising administering to the animal epithelin 1 in an amount effective at inhibiting epithelial neoplastic cell proliferation.

6. The method of claim 5 wherein the epithelin 1 is human epithelin 1 having the amino acid sequence as depicted in SEQ ID NO:4 from about amino acid residue numbers 282 to 337.

7. The method of claim 5 wherein the epithelin 1 is rat epithelin 1 having the amino acid sequence as depicted in SEQ ID NO:2 from amino acid residue numbers 280 to 335.

8. The method of claim 5 wherein the epithelin 1 is mouse epithelin 1 having the amino acid sequence as depicted in SEQ ID NO:6 from amino acid residue numbers 280 to 335.

9. A method of modulating keratinocyte proliferation comprising administering to the keratinocytes epithelin 1 in an amount effective at stimulating keratinocyte cell proliferation.

10. The method of claim 9 wherein the epithelin 1 is human epithelin 1 having the amino acid sequence as depicted in SEQ ID NO:4 from about amino acid residue numbers 282–337.

11. The method of claim 9 wherein the epithelin 1 is rat epithelin 1 having the amino acid sequence as depicted in SEQ ID NO:2 from amino acid residues number 280 to 335.

12. The method of claim 9 wherein the epithelin 1 is mouse epithelin 1 having the amino acid sequence as depicted in SEQ ID NO:6 from amino acid residue number 280 to 335.

13. A method of inhibiting keratinocyte proliferation comprising administering to an individual a composition effective at inhibiting epithelin 1 growth stimulatory activity.

14. The method according to claim 13 wherein the composition comprises epithelin 2.

15. A method of inhibiting the growth of neoplastic epidermoid cells comprising contacting the neoplastic epidermoid cells with an amount of epithelin 2 effective at inhibiting epidermoid neoplastic cell growth.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 1767 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i x ) FEATURE:
( A ) NAME/KEY: CDS
( B ) LOCATION: 1..1767

( x i ) SEQUENCE DESCRIPTION: SEQ ID NO:1:

```
ATG  TGG  ATC  CTG  GTG  AGC  TGG  CTG  GCC  TTA  GTG  GCA  AGG  CTG  GTG  GCT        48
Met  Trp  Ile  Leu  Val  Ser  Trp  Leu  Ala  Leu  Val  Ala  Arg  Leu  Val  Ala
 1                  5                        10                       15

GGA  ACA  CAG  TGC  CCA  GAT  GGT  CAA  TTC  TGC  CCT  GTT  GCC  TGC  TGC  CTT        96
Gly  Thr  Gln  Cys  Pro  Asp  Gly  Gln  Phe  Cys  Pro  Val  Ala  Cys  Cys  Leu
                    20                       25                       30

GAC  CAG  GGA  GGA  GCC  AAC  TAC  AGC  TGC  TGT  AAC  CCT  CTT  CTG  GAC  ACA       144
Asp  Gln  Gly  Gly  Ala  Asn  Tyr  Ser  Cys  Cys  Asn  Pro  Leu  Leu  Asp  Thr
          35                       40                       45

TGG  CCT  ATA  ATA  ACG  AGC  CGT  CGT  CTA  GAT  GGC  TCC  TGC  CAG  ATC  CGT       192
Trp  Pro  Ile  Ile  Thr  Ser  Arg  Arg  Leu  Asp  Gly  Ser  Cys  Gln  Ile  Arg
     50                       55                       60

GAC  CAC  TGT  CCT  GAT  GGC  TAC  TCT  TGT  CTT  CTC  ACT  GTG  TCT  GGG  ACT       240
Asp  His  Cys  Pro  Asp  Gly  Tyr  Ser  Cys  Leu  Leu  Thr  Val  Ser  Gly  Thr
 65                       70                       75                       80

TCC  AGC  TGC  TGC  CCG  TTC  TCT  GAG  GGT  GTA  TCT  TGT  GAT  GAT  GGC  CAG       288
Ser  Ser  Cys  Cys  Pro  Phe  Ser  Glu  Gly  Val  Ser  Cys  Asp  Asp  Gly  Gln
                    85                       90                       95
```

| | | | | | | | | | | | | | | | | |
|---|---|---|---|---|---|---|---|---|---|---|---|---|---|---|---|---|
| CAC | TGC | TGC | CCC | CGG | GGC | TTC | CAC | TGT | AGT | GCG | GAT | GGG | AAA | TCC | TGC | 336 |
| His | Cys | Cys | Pro | Arg | Gly | Phe | His | Cys | Ser | Ala | Asp | Gly | Lys | Ser | Cys | |
| | | | 100 | | | | 105 | | | | | 110 | | | | |
| TCT | CAG | ATA | TCA | GAT | AGC | CTC | TTG | GGT | GCT | GTC | CAG | TGT | CCT | GGT | AGC | 384 |
| Ser | Gln | Ile | Ser | Asp | Ser | Leu | Leu | Gly | Ala | Val | Gln | Cys | Pro | Gly | Ser | |
| | | 115 | | | | | 120 | | | | | 125 | | | | |
| CAG | TTC | GAA | TGT | CCT | GAC | TCC | GCC | ACC | TGC | TGT | ATT | ATG | ATT | GAT | GGT | 432 |
| Gln | Phe | Glu | Cys | Pro | Asp | Ser | Ala | Thr | Cys | Cys | Ile | Met | Ile | Asp | Gly | |
| | 130 | | | | | 135 | | | | | | 140 | | | | |
| TCC | TGG | GGG | TGC | TGC | CCC | ATG | CCC | CAG | GCC | TCT | TGC | TGT | GAA | GAC | AGA | 480 |
| Ser | Trp | Gly | Cys | Cys | Pro | Met | Pro | Gln | Ala | Ser | Cys | Cys | Glu | Asp | Arg | |
| 145 | | | | | 150 | | | | | 155 | | | | | 160 | |
| GTG | CAT | TGC | TGT | CCC | CAC | GGG | GCC | TCC | TGT | GAC | CTG | GTT | CAC | ACG | CGA | 528 |
| Val | His | Cys | Cys | Pro | His | Gly | Ala | Ser | Cys | Asp | Leu | Val | His | Thr | Arg | |
| | | | | 165 | | | | | 170 | | | | | 175 | | |
| TGC | ATT | TCA | CCC | ACG | GGC | ACC | CAC | CCC | TTA | CTA | AAG | AAA | TTC | CCC | GCA | 576 |
| Cys | Ile | Ser | Pro | Thr | Gly | Thr | His | Pro | Leu | Leu | Lys | Lys | Phe | Pro | Ala | |
| | | | 180 | | | | | 185 | | | | | 190 | | | |
| CAA | AGG | ACC | AAC | AGG | GCA | GTG | GCT | TTC | CCT | TTT | TCC | GTG | GTG | TGC | CCT | 624 |
| Gln | Arg | Thr | Asn | Arg | Ala | Val | Ala | Phe | Pro | Phe | Ser | Val | Val | Cys | Pro | |
| | | 195 | | | | | 200 | | | | | 205 | | | | |
| GAT | GCT | AAG | ACC | CAG | TGC | CCT | GAT | GAC | TCT | ACC | TGC | TGT | GAG | CTA | CCC | 672 |
| Asp | Ala | Lys | Thr | Gln | Cys | Pro | Asp | Asp | Ser | Thr | Cys | Cys | Glu | Leu | Pro | |
| | 210 | | | | | 215 | | | | | 220 | | | | | |
| ACT | GGG | AAG | TAT | GGC | TGT | TGT | CCA | ATG | CCC | AAC | GCC | ATC | TGC | TGT | TCC | 720 |
| Thr | Gly | Lys | Tyr | Gly | Cys | Cys | Pro | Met | Pro | Asn | Ala | Ile | Cys | Cys | Ser | |
| 225 | | | | | 230 | | | | | 235 | | | | | 240 | |
| GAC | CAC | CTG | CAC | TGC | TGC | CCC | CAG | GAC | ACT | GTA | TGT | GAC | CTG | ATC | CAG | 768 |
| Asp | His | Leu | His | Cys | Cys | Pro | Gln | Asp | Thr | Val | Cys | Asp | Leu | Ile | Gln | |
| | | | | 245 | | | | | 250 | | | | | 255 | | |
| AGC | AAG | TGC | ATA | TCC | AAG | GAC | TAC | ACC | ACA | GAT | CTC | ATG | ACC | AAG | CTG | 816 |
| Ser | Lys | Cys | Ile | Ser | Lys | Asp | Tyr | Thr | Thr | Asp | Leu | Met | Thr | Lys | Leu | |
| | | | 260 | | | | | 265 | | | | | 270 | | | |
| CCT | GGA | TAC | CCA | GTG | AAT | GAG | GTG | AAG | TGC | GAC | TTG | GAG | GTG | AGC | TGT | 864 |
| Pro | Gly | Tyr | Pro | Val | Asn | Glu | Val | Lys | Cys | Asp | Leu | Glu | Val | Ser | Cys | |
| | | 275 | | | | | 280 | | | | | 285 | | | | |
| CCT | GAT | GGC | TAC | ACC | TGC | TGC | CGC | CTC | AAC | ACT | GGG | GCC | TGG | GGC | TGC | 912 |
| Pro | Asp | Gly | Tyr | Thr | Cys | Cys | Arg | Leu | Asn | Thr | Gly | Ala | Trp | Gly | Cys | |
| | 290 | | | | | 295 | | | | | 300 | | | | | |
| TGT | CCA | TTC | ACC | AAG | GCT | GTG | TGT | TGT | GAA | GAC | CAC | ATT | CAC | TGC | TGC | 960 |
| Cys | Pro | Phe | Thr | Lys | Ala | Val | Cys | Cys | Glu | Asp | His | Ile | His | Cys | Cys | |
| 305 | | | | | 310 | | | | | 315 | | | | | 320 | |
| CCA | GCC | GGG | TTT | CAG | TGT | CAC | ACA | GAG | ACA | GGA | ACC | TGT | GAA | CTG | GGA | 1008 |
| Pro | Ala | Gly | Phe | Gln | Cys | His | Thr | Glu | Thr | Gly | Thr | Cys | Glu | Leu | Gly | |
| | | | | 325 | | | | | 330 | | | | | 335 | | |
| GTC | CTT | CAG | GTA | CCC | TGG | ATG | AAA | AAG | GTC | ACG | GCC | TCC | CTC | AGC | CTG | 1056 |
| Val | Leu | Gln | Val | Pro | Trp | Met | Lys | Lys | Val | Thr | Ala | Ser | Leu | Ser | Leu | |
| | | | 340 | | | | | 345 | | | | | 350 | | | |
| CCA | GAC | CCA | CAG | ATC | TTG | AAG | AAT | GAT | GTC | CCC | TGT | GAT | GAC | TTC | AGT | 1104 |
| Pro | Asp | Pro | Gln | Ile | Leu | Lys | Asn | Asp | Val | Pro | Cys | Asp | Asp | Phe | Ser | |
| | | 355 | | | | | 360 | | | | | 365 | | | | |
| AGC | TGT | CCT | TCT | AAC | AAT | ACC | TGC | TGC | AGA | CTC | AGT | TCT | GGG | GAC | TGG | 1152 |
| Ser | Cys | Pro | Ser | Asn | Asn | Thr | Cys | Cys | Arg | Leu | Ser | Ser | Gly | Asp | Trp | |
| | 370 | | | | | 375 | | | | | 380 | | | | | |
| GGC | TGC | TGT | CCC | ATC | CCA | GAG | GCT | GTC | TGC | TGC | TTA | GAC | CAC | CAG | CAT | 1200 |
| Gly | Cys | Cys | Pro | Ile | Pro | Glu | Ala | Val | Cys | Cys | Leu | Asp | His | Gln | His | |
| 385 | | | | | 390 | | | | | 395 | | | | | 400 | |
| TGC | TGC | CCT | CAG | GGT | TTC | AAA | TGT | ATG | GAT | GAG | GGG | TAC | TGT | CAG | AAG | 1248 |
| Cys | Cys | Pro | Gln | Gly | Phe | Lys | Cys | Met | Asp | Glu | Gly | Tyr | Cys | Gln | Lys | |
| | | | | 405 | | | | | 410 | | | | | 415 | | |

| | | | | | | | | | | | | | | | |
|---|---|---|---|---|---|---|---|---|---|---|---|---|---|---|---|
| GGA | GAC | AGA | ATG | GTG | GCT | GGC | CTG | GAG | AAG | ATG | CCT | GTC | CGC | CAG | ACA | 1296 |
| Gly | Asp | Arg | Met 420 | Val | Ala | Gly | Leu | Glu 425 | Lys | Met | Pro | Val | Arg 430 | Gln | Thr | |
| ACT | CTG | CTC | CAA | CAT | GGA | GAT | ATT | GGT | TGT | GAC | CAG | CAT | ACC | AGC | TGC | 1344 |
| Thr | Leu | Leu 435 | Gln | His | Gly | Asp | Ile 440 | Gly | Cys | Asp | Gln | His 445 | Thr | Ser | Cys | |
| CCA | GTA | GGG | CAA | ACA | TGC | TGC | CCA | AGC | CTG | AAG | GGA | AGT | TGG | GCC | TGC | 1392 |
| Pro | Val 450 | Gly | Gln | Thr | Cys | Cys 455 | Pro | Ser | Leu | Lys | Gly 460 | Ser | Trp | Ala | Cys | |
| TGC | CAG | TTG | CCC | CAT | GCT | GTG | TGC | TGT | GAG | GAC | CGG | CAG | CAC | TGT | TGC | 1440 |
| Cys 465 | Gln | Leu | Pro | His 470 | Ala | Val | Cys | Cys | Glu 475 | Asp | Arg | Gln | His | Cys 480 | Cys | |
| CCG | GCT | GGG | TAC | ACC | TGC | AAC | GTG | AAG | GCG | AGA | ACC | TGT | GAG | AAG | GAT | 1488 |
| Pro | Ala | Gly | Tyr | Thr 485 | Cys | Asn | Val | Lys | Ala 490 | Arg | Thr | Cys | Glu | Lys 495 | Asp | |
| GCA | GGC | TCT | GTC | CAG | CCT | TCC | ATG | GAC | CTG | ACC | TTT | GGC | TCT | AAG | GTT | 1536 |
| Ala | Gly | Ser | Val 500 | Gln | Pro | Ser | Met | Asp 505 | Leu | Thr | Phe | Gly | Ser 510 | Lys | Val | |
| GGG | AAT | GTG | GAA | TGT | GGT | GCC | GGA | CAT | TTC | TGC | CAT | GAT | AAC | CAG | TCC | 1584 |
| Gly | Asn | Val 515 | Glu | Cys | Gly | Ala | Gly 520 | His | Phe | Cys | His | Asp 525 | Asn | Gln | Ser | |
| TGT | TGT | AAA | GAC | AGC | CAA | GGA | GGC | TGG | GCC | TGC | TGT | CCC | TAT | GTA | AAG | 1632 |
| Cys | Cys 530 | Lys | Asp | Ser | Gln | Gly 535 | Gly | Trp | Ala | Cys | Cys 540 | Pro | Tyr | Val | Lys | |
| GGT | GTC | TGC | TGT | AGA | GAT | GGA | CGT | CAC | TGT | TGT | CCC | ATT | GGC | TTC | CAC | 1680 |
| Gly | Val | Cys 545 | Cys | Arg | Asp | Gly 550 | Arg | His | Cys | Cys 555 | Pro | Ile | Gly | Phe | His 560 | |
| TGT | TCA | GCC | AAG | GGA | ACC | AAG | TGT | TTG | CGG | AAG | AAG | ACC | CCT | CGC | TGG | 1728 |
| Cys | Ser | Ala | Lys | Gly 565 | Thr | Lys | Cys | Leu | Arg 570 | Lys | Lys | Thr | Pro | Arg 575 | Trp | |
| GAC | ATA | CTT | TTG | AGG | GAT | CCA | GCC | CCA | AGA | CCG | CTA | CTG | | | | 1767 |
| Asp | Ile | Leu | Leu 580 | Arg | Asp | Pro | Ala | Pro 585 | Arg | Pro | Leu | Leu | | | | |

( 2 ) INFORMATION FOR SEQ ID NO:2:

( i ) SEQUENCE CHARACTERISTICS:
        ( A ) LENGTH: 589 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Trp | Ile | Leu | Val 5 | Ser | Trp | Leu | Ala | Leu 10 | Val | Ala | Arg | Leu | Val 15 | Ala |
| Gly | Thr | Gln | Cys 20 | Pro | Asp | Gly | Gln | Phe 25 | Cys | Pro | Val | Ala | Cys 30 | Cys | Leu |
| Asp | Gln | Gly 35 | Gly | Ala | Asn | Tyr | Ser 40 | Cys | Cys | Asn | Pro | Leu 45 | Leu | Asp | Thr |
| Trp | Pro 50 | Ile | Ile | Thr | Ser | Arg 55 | Arg | Leu | Asp | Gly | Ser 60 | Cys | Gln | Ile | Arg |
| Asp 65 | His | Cys | Pro | Asp | Gly 70 | Tyr | Ser | Cys | Leu | Leu 75 | Thr | Val | Ser | Gly | Thr 80 |
| Ser | Ser | Cys | Cys | Pro 85 | Phe | Ser | Glu | Gly | Val 90 | Ser | Cys | Asp | Asp | Gly 95 | Gln |
| His | Cys | Cys | Pro 100 | Arg | Gly | Phe | His | Cys 105 | Ser | Ala | Asp | Gly | Lys 110 | Ser | Cys |
| Ser | Gln | Ile 115 | Ser | Asp | Ser | Leu | Leu 120 | Gly | Ala | Val | Gln | Cys 125 | Pro | Gly | Ser |

```
Gln  Phe  Glu  Cys  Pro  Asp  Ser  Ala  Thr  Cys  Cys  Ile  Met  Ile  Asp  Gly
     130                 135                 140

Ser  Trp  Gly  Cys  Cys  Pro  Met  Pro  Gln  Ala  Ser  Cys  Cys  Glu  Asp  Arg
145                      150                 155                           160

Val  His  Cys  Cys  Pro  His  Gly  Ala  Ser  Cys  Asp  Leu  Val  His  Thr  Arg
                    165                 170                      175

Cys  Ile  Ser  Pro  Thr  Gly  Thr  His  Pro  Leu  Leu  Lys  Lys  Phe  Pro  Ala
               180                      185                      190

Gln  Arg  Thr  Asn  Arg  Ala  Val  Ala  Phe  Pro  Phe  Ser  Val  Val  Cys  Pro
          195                 200                 205

Asp  Ala  Lys  Thr  Gln  Cys  Pro  Asp  Asp  Ser  Thr  Cys  Cys  Glu  Leu  Pro
     210                 215                      220

Thr  Gly  Lys  Tyr  Gly  Cys  Pro  Met  Pro  Asn  Ala  Ile  Cys  Cys  Ser
225                      230                 235                           240

Asp  His  Leu  His  Cys  Cys  Pro  Gln  Asp  Thr  Val  Cys  Asp  Leu  Ile  Gln
                    245                 250                      255

Ser  Lys  Cys  Ile  Ser  Lys  Asp  Tyr  Thr  Thr  Asp  Leu  Met  Thr  Lys  Leu
               260                 265                      270

Pro  Gly  Tyr  Pro  Val  Asn  Glu  Val  Lys  Cys  Asp  Leu  Glu  Val  Ser  Cys
          275                 280                 285

Pro  Asp  Gly  Tyr  Thr  Cys  Cys  Arg  Leu  Asn  Thr  Gly  Ala  Trp  Gly  Cys
     290                 295                 300

Cys  Pro  Phe  Thr  Lys  Ala  Val  Cys  Cys  Glu  Asp  His  Ile  His  Cys  Cys
305                      310                 315                           320

Pro  Ala  Gly  Phe  Gln  Cys  His  Thr  Glu  Thr  Gly  Thr  Cys  Glu  Leu  Gly
                    325                 330                      335

Val  Leu  Gln  Val  Pro  Trp  Met  Lys  Lys  Val  Thr  Ala  Ser  Leu  Ser  Leu
               340                 345                      350

Pro  Asp  Pro  Gln  Ile  Leu  Lys  Asn  Asp  Val  Pro  Cys  Asp  Asp  Phe  Ser
          355                 360                 365

Ser  Cys  Pro  Ser  Asn  Asn  Thr  Cys  Cys  Arg  Leu  Ser  Ser  Gly  Asp  Trp
     370                 375                 380

Gly  Cys  Cys  Pro  Ile  Pro  Glu  Ala  Val  Cys  Cys  Leu  Asp  His  Gln  His
385                      390                 395                           400

Cys  Cys  Pro  Gln  Gly  Phe  Lys  Cys  Met  Glu  Gly  Tyr  Cys  Gln  Lys
                    405                 410                      415

Gly  Asp  Arg  Met  Val  Ala  Gly  Leu  Glu  Lys  Met  Pro  Val  Arg  Gln  Thr
               420                 425                      430

Thr  Leu  Leu  Gln  His  Gly  Asp  Ile  Gly  Cys  Asp  Gln  His  Thr  Ser  Cys
          435                 440                 445

Pro  Val  Gly  Gln  Thr  Cys  Cys  Pro  Ser  Leu  Lys  Gly  Ser  Trp  Ala  Cys
     450                 455                 460

Cys  Gln  Leu  Pro  His  Ala  Val  Cys  Cys  Glu  Asp  Arg  Gln  His  Cys  Cys
465                      470                 475                           480

Pro  Ala  Gly  Tyr  Thr  Cys  Asn  Val  Lys  Ala  Arg  Thr  Cys  Glu  Lys  Asp
                    485                 490                      495

Ala  Gly  Ser  Val  Gln  Pro  Ser  Met  Asp  Leu  Thr  Phe  Gly  Ser  Lys  Val
               500                 505                      510

Gly  Asn  Val  Glu  Cys  Gly  Ala  Gly  His  Phe  Cys  His  Asp  Asn  Gln  Ser
          515                 520                 525

Cys  Cys  Lys  Asp  Ser  Gln  Gly  Gly  Trp  Ala  Cys  Cys  Pro  Tyr  Val  Lys
     530                 535                 540

Gly  Val  Cys  Cys  Arg  Asp  Gly  Arg  His  Cys  Cys  Pro  Ile  Gly  Phe  His
```

|  |  |  |  |  |  |  |  |  |  |  |  |  |  |  |  |  |
|---|---|---|---|---|---|---|---|---|---|---|---|---|---|---|---|---|
| 545 |  |  |  | 550 |  |  |  | 555 |  |  |  | 560 |  |  |  |  |
| Cys | Ser | Ala | Lys | Gly | Thr | Lys | Cys | Leu | Arg | Lys | Lys | Thr | Pro | Arg | Trp |  |
|  |  |  |  | 565 |  |  |  | 570 |  |  |  | 575 |  |  |  |  |
| Asp | Ile | Leu | Leu | Arg | Asp | Pro | Ala | Pro | Arg | Pro | Leu | Leu |  |  |  |  |
|  |  |  |  | 580 |  |  |  | 585 |  |  |  |  |  |  |  |  |

( 2 ) INFORMATION FOR SEQ ID NO:3:

( i ) SEQUENCE CHARACTERISTICS:
        ( A ) LENGTH: 1779 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens
        ( F ) TISSUE TYPE: Kidney ( i x ) FEATURE:
        ( A ) NAME/KEY: CDS
        ( B ) LOCATION: 1..1779

( x i ) SEQUENCE DESCRIPTION: SEQ ID NO:3:

|  |  |  |  |  |  |  |  |  |  |  |  |  |  |  |  |  |
|---|---|---|---|---|---|---|---|---|---|---|---|---|---|---|---|---|
| ATG | TGG | ACC | CTG | GTG | AGC | TGG | GTG | GCC | TTA | ACA | GCA | GGG | CTG | GTG | GCT | 48 |
| Met | Trp | Thr | Leu | Val | Ser | Trp | Val | Ala | Leu | Thr | Ala | Gly | Leu | Val | Ala |  |
| 1 |  |  |  | 5 |  |  |  |  | 10 |  |  |  |  | 15 |  |  |
| GGA | ACG | CGG | TGC | CCA | GAT | GGT | CAG | TTC | TGC | CCT | GTG | GCC | TGC | TGC | CTG | 96 |
| Gly | Thr | Arg | Cys | Pro | Asp | Gly | Gln | Phe | Cys | Pro | Val | Ala | Cys | Cys | Leu |  |
|  |  |  | 20 |  |  |  |  | 25 |  |  |  |  | 30 |  |  |  |
| GAC | CCC | GGA | GGA | GCC | AGC | TAC | AGC | TGC | TGC | CGT | CCC | CTT | CTG | GAC | AAA | 144 |
| Asp | Pro | Gly | Gly | Ala | Ser | Tyr | Ser | Cys | Cys | Arg | Pro | Leu | Leu | Asp | Lys |  |
|  |  | 35 |  |  |  |  | 40 |  |  |  |  | 45 |  |  |  |  |
| TGG | CCC | ACA | ACA | CTG | AGC | AGG | CAT | CTG | GGT | GGC | CCC | TGC | CAG | GTT | GAT | 192 |
| Trp | Pro | Thr | Thr | Leu | Ser | Arg | His | Leu | Gly | Gly | Pro | Cys | Gln | Val | Asp |  |
|  | 50 |  |  |  |  | 55 |  |  |  |  | 60 |  |  |  |  |  |
| GCC | CAC | TGC | TCT | GCC | GGC | CAC | TCC | TGC | ATC | TTT | ACC | GTC | TCA | GGG | ACT | 240 |
| Ala | His | Cys | Ser | Ala | Gly | His | Ser | Cys | Ile | Phe | Thr | Val | Ser | Gly | Thr |  |
| 65 |  |  |  |  | 70 |  |  |  |  | 75 |  |  |  |  | 80 |  |
| TCC | AGT | TGC | TGC | CCC | TTC | CCA | GAG | GCC | GTG | GCA | TGC | GGG | GAT | GGC | CAT | 288 |
| Ser | Ser | Cys | Cys | Pro | Phe | Pro | Glu | Ala | Val | Ala | Cys | Gly | Asp | Gly | His |  |
|  |  |  |  | 85 |  |  |  |  | 90 |  |  |  |  | 95 |  |  |
| CAC | TGC | TGC | CCA | CGG | GGC | TTC | CAC | TGC | AGT | GCA | GAC | GGG | CGA | TCC | TGC | 336 |
| His | Cys | Cys | Pro | Arg | Gly | Phe | His | Cys | Ser | Ala | Asp | Gly | Arg | Ser | Cys |  |
|  |  |  | 100 |  |  |  |  | 105 |  |  |  |  | 110 |  |  |  |
| TTC | CAA | AGA | TCA | GGT | AAC | AAC | TCC | GTG | GGT | GCC | ATC | CAG | TGC | CCT | GAT | 384 |
| Phe | Gln | Arg | Ser | Gly | Asn | Asn | Ser | Val | Gly | Ala | Ile | Gln | Cys | Pro | Asp |  |
|  |  | 115 |  |  |  |  | 120 |  |  |  |  | 125 |  |  |  |  |
| AGT | CAG | TTC | GAA | TGC | CCG | GAC | TTC | TCC | ACG | TGC | TGT | GTT | ATG | GTC | GAT | 432 |
| Ser | Gln | Phe | Glu | Cys | Pro | Asp | Phe | Ser | Thr | Cys | Cys | Val | Met | Val | Asp |  |
|  | 130 |  |  |  |  | 135 |  |  |  |  | 140 |  |  |  |  |  |
| GGC | TCC | TGG | GGG | TGC | TGC | CCC | ATG | CCC | CAG | GCT | TCC | TGC | TGT | GAA | GAC | 480 |
| Gly | Ser | Trp | Gly | Cys | Cys | Pro | Met | Pro | Gln | Ala | Ser | Cys | Cys | Glu | Asp |  |
| 145 |  |  |  |  | 150 |  |  |  |  | 155 |  |  |  |  | 160 |  |
| AGG | GTG | CAC | TGC | TGT | CCG | CAC | GGT | GCC | TTC | TGC | GAC | CTG | GTT | CAC | ACC | 528 |
| Arg | Val | His | Cys | Cys | Pro | His | Gly | Ala | Phe | Cys | Asp | Leu | Val | His | Thr |  |
|  |  |  |  | 165 |  |  |  |  | 170 |  |  |  |  | 175 |  |  |
| CGC | TGC | ATC | ACA | CCC | ACG | GGC | ACC | CAC | CCC | CTG | GCA | AAG | AAG | CTC | CCT | 576 |
| Arg | Cys | Ile | Thr | Pro | Thr | Gly | Thr | His | Pro | Leu | Ala | Lys | Lys | Leu | Pro |  |
|  |  |  | 180 |  |  |  |  | 185 |  |  |  |  | 190 |  |  |  |
| GCC | CAG | AGG | ACT | AAC | AGG | GCA | GTG | GCC | TTG | TCC | AGC | TCG | GTC | ATG | TGT | 624 |
| Ala | Gln | Arg | Thr | Asn | Arg | Ala | Val | Ala | Leu | Ser | Ser | Ser | Val | Met | Cys |  |
|  | 195 |  |  |  |  | 200 |  |  |  |  | 205 |  |  |  |  |  |

| | | | | | | | | | | | | | | | |
|---|---|---|---|---|---|---|---|---|---|---|---|---|---|---|---|
| CCG | GAC | GCA | CGG | TCC | CGG | TGC | CCT | GAT | GGT | TCT | ACC | TGC | TGT | GAG | CTG | 672
| Pro | Asp | Ala | Arg | Ser | Arg | Cys | Pro | Asp | Gly | Ser | Thr | Cys | Cys | Glu | Leu |
| | 210 | | | | 215 | | | | | | 220 | | | | |
| CCC | AGT | GGG | AAG | TAT | GGC | TGC | TGC | CCA | ATG | CCC | AAC | GCC | ACC | TGC | TGC | 720
| Pro | Ser | Gly | Lys | Tyr | Gly | Cys | Cys | Pro | Met | Pro | Asn | Ala | Thr | Cys | Cys |
| 225 | | | | | 230 | | | | | 235 | | | | | 240 |
| TCC | GAT | CAC | CTG | CAC | TGC | TGC | CCC | CAA | GAC | ACT | GTG | TGT | GAC | CTG | ATC | 768
| Ser | Asp | His | Leu | His | Cys | Cys | Pro | Gln | Asp | Thr | Val | Cys | Asp | Leu | Ile |
| | | | | 245 | | | | | 250 | | | | | 255 | |
| CAG | AGT | AAG | TGC | CTC | TCC | AAG | GAG | AAC | GCT | ACC | ACG | GAC | CTC | CTC | ACT | 816
| Gln | Ser | Lys | Cys | Leu | Ser | Lys | Glu | Asn | Ala | Thr | Thr | Asp | Leu | Leu | Thr |
| | | | | 260 | | | | | 265 | | | | | 270 | |
| AAG | CTG | CCT | GCG | CAC | ACA | GTG | GGG | GAT | GTG | AAA | TGT | GAC | ATG | GAG | GTG | 864
| Lys | Leu | Pro | Ala | His | Thr | Val | Gly | Asp | Val | Lys | Cys | Asp | Met | Glu | Val |
| | | 275 | | | | | 280 | | | | | 285 | | | |
| AGC | TGC | CCA | GAT | GGC | TAT | ACC | TGC | TGC | CGT | CTA | CAG | TCG | GGG | GCC | TGG | 912
| Ser | Cys | Pro | Asp | Gly | Tyr | Thr | Cys | Cys | Arg | Leu | Gln | Ser | Gly | Ala | Trp |
| | 290 | | | | | 295 | | | | | 300 | | | | |
| GGC | TGC | TGC | CCT | TTT | ACC | CAG | GCT | GTG | TGC | TGT | GAG | GAC | CAC | ATA | CAC | 960
| Gly | Cys | Cys | Pro | Phe | Thr | Gln | Ala | Val | Cys | Cys | Glu | Asp | His | Ile | His |
| 305 | | | | | 310 | | | | | 315 | | | | | 320 |
| TGC | TGT | CCC | GCG | GGG | TTT | ACG | TGT | GAC | ACG | CAG | AAG | GGT | ACC | TGT | GAA | 1008
| Cys | Cys | Pro | Ala | Gly | Phe | Thr | Cys | Asp | Thr | Gln | Lys | Gly | Thr | Cys | Glu |
| | | | | 325 | | | | | 330 | | | | | 335 | |
| CAG | GGG | CCC | CAC | CAG | GTG | CCC | TGG | ATG | GAG | AAG | GCC | CCA | GCT | CAC | CTC | 1056
| Gln | Gly | Pro | His | Gln | Val | Pro | Trp | Met | Glu | Lys | Ala | Pro | Ala | His | Leu |
| | | | 340 | | | | | 345 | | | | | 350 | | |
| AGC | CTG | CCA | GAC | CCA | CAA | GCC | TTG | AAG | AGA | GAT | GTC | CCC | TGT | GAT | AAT | 1104
| Ser | Leu | Pro | Asp | Pro | Gln | Ala | Leu | Lys | Arg | Asp | Val | Pro | Cys | Asp | Asn |
| | | 355 | | | | | 360 | | | | | 365 | | | |
| GTC | AGC | AGC | TGT | CCC | TCC | TCC | GAT | ACC | TGC | TGC | CAA | CTC | ACG | TCT | GGG | 1152
| Val | Ser | Ser | Cys | Pro | Ser | Ser | Asp | Thr | Cys | Cys | Gln | Leu | Thr | Ser | Gly |
| | 370 | | | | | 375 | | | | | 380 | | | | |
| GAG | TGG | GGC | TGC | TGT | CCA | ATC | CCA | GAG | GCT | GTC | TGC | TGC | TCG | GAC | CAC | 1200
| Glu | Trp | Gly | Cys | Cys | Pro | Ile | Pro | Glu | Ala | Val | Cys | Cys | Ser | Asp | His |
| 385 | | | | | 390 | | | | | 395 | | | | | 400 |
| CAG | CAC | TGC | TGC | CCC | CAG | GGC | TAC | ACG | TGT | GTA | GCT | GAG | GGG | CAG | TGT | 1248
| Gln | His | Cys | Cys | Pro | Gln | Gly | Tyr | Thr | Cys | Val | Ala | Glu | Gly | Gln | Cys |
| | | | | 405 | | | | | 410 | | | | | 415 | |
| CAG | CGA | GGA | AGC | GAG | ATC | GTG | GCT | GGA | CTG | GAG | AAG | ATG | CCT | GCC | CGC | 1296
| Gln | Arg | Gly | Ser | Glu | Ile | Val | Ala | Gly | Leu | Glu | Lys | Met | Pro | Ala | Arg |
| | | | 420 | | | | | 425 | | | | | 430 | | |
| CGG | GCT | TCC | TTA | TCC | CAC | CCC | AGA | GAC | ATC | GGC | TGT | GAC | CAG | CAC | ACC | 1344
| Arg | Ala | Ser | Leu | Ser | His | Pro | Arg | Asp | Ile | Gly | Cys | Asp | Gln | His | Thr |
| | | 435 | | | | | 440 | | | | | 445 | | | |
| AGC | TGC | CCG | GTG | GGG | CAG | ACC | TGC | TGC | CCG | AGC | CTG | GGT | GGG | AGC | TGG | 1392
| Ser | Cys | Pro | Val | Gly | Gln | Thr | Cys | Cys | Pro | Ser | Leu | Gly | Gly | Ser | Trp |
| | 450 | | | | | 455 | | | | | 460 | | | | |
| GCC | TGC | TGC | CAG | TTG | CCC | CAT | GCT | GTG | TGC | TGC | GAG | GAT | CGC | CAG | CAC | 1440
| Ala | Cys | Cys | Gln | Leu | Pro | His | Ala | Val | Cys | Cys | Glu | Asp | Arg | Gln | His |
| 465 | | | | | 470 | | | | | 475 | | | | | 480 |
| TGC | TGC | CCG | GCT | GGC | TAC | ACC | TGC | AAC | GTG | AAG | GCT | CGA | TCC | TGC | GAG | 1488
| Cys | Cys | Pro | Ala | Gly | Tyr | Thr | Cys | Asn | Val | Lys | Ala | Arg | Ser | Cys | Glu |
| | | | | 485 | | | | | 490 | | | | | 495 | |
| AAG | GAA | GTG | GTC | TCT | GCC | CAG | CCT | GCC | ACC | TTC | CTG | GCC | CGT | AGC | CCT | 1536
| Lys | Glu | Val | Val | Ser | Ala | Gln | Pro | Ala | Thr | Phe | Leu | Ala | Arg | Ser | Pro |
| | | | 500 | | | | | 505 | | | | | 510 | | |
| CAC | GTG | GGT | GTG | AAG | GAC | GTG | GAG | TGT | GGG | GAA | GGA | CAC | TTC | TGC | CAT | 1584
| His | Val | Gly | Val | Lys | Asp | Val | Glu | Cys | Gly | Glu | Gly | His | Phe | Cys | His |
| | | 515 | | | | | 520 | | | | | 525 | | | |

```
GAT  AAC  CAG  ACC  TGC  TGC  CGA  GAC  AAC  CGA  CAG  GGC  TGG  GCC  TGC  TGT     1632
Asp  Asn  Gln  Thr  Cys  Cys  Arg  Asp  Asn  Arg  Gln  Gly  Trp  Ala  Cys  Cys
     530                      535                      540

CCC  TAC  CGC  CAG  GGC  GTC  TGT  TGT  GCT  GAT  CGG  CGC  CAC  TGC  TGT  CCT     1680
Pro  Tyr  Arg  Gln  Gly  Val  Cys  Cys  Ala  Asp  Arg  Arg  His  Cys  Cys  Pro
545                      550                      555                      560

GCT  GGC  TTC  CGC  TGC  GCA  GCC  AGG  GGT  ACC  AAG  TGT  TTG  CGC  AGG  GAG     1728
Ala  Gly  Phe  Arg  Cys  Ala  Ala  Arg  Gly  Thr  Lys  Cys  Leu  Arg  Arg  Glu
               565                          570                     575

GCC  CCG  CGC  TGG  GAC  GCC  CCT  TTG  AGG  GAC  CCA  GCC  TTG  AGA  CAG  CTG     1776
Ala  Pro  Arg  Trp  Asp  Ala  Pro  Leu  Arg  Asp  Pro  Ala  Leu  Arg  Gln  Leu
               580                     585                     590

CTG                                                                                 1779
Leu
```

(2) INFORMATION FOR SEQ ID NO:4:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Trp  Thr  Leu  Val  Ser  Trp  Val  Ala  Leu  Thr  Ala  Gly  Leu  Val  Ala
 1             5                     10                      15

Gly  Thr  Arg  Cys  Pro  Asp  Gly  Gln  Phe  Cys  Pro  Val  Ala  Cys  Cys  Leu
               20                      25                      30

Asp  Pro  Gly  Gly  Ala  Ser  Tyr  Ser  Cys  Cys  Arg  Pro  Leu  Leu  Asp  Lys
               35                      40                      45

Trp  Pro  Thr  Thr  Leu  Ser  Arg  His  Leu  Gly  Gly  Pro  Cys  Gln  Val  Asp
     50                      55                      60

Ala  His  Cys  Ser  Ala  Gly  His  Ser  Cys  Ile  Phe  Thr  Val  Ser  Gly  Thr
 65                      70                      75                      80

Ser  Ser  Cys  Cys  Pro  Phe  Pro  Glu  Ala  Val  Ala  Cys  Gly  Asp  Gly  His
               85                      90                      95

His  Cys  Cys  Pro  Arg  Gly  Phe  His  Cys  Ser  Ala  Asp  Gly  Arg  Ser  Cys
               100                     105                     110

Phe  Gln  Arg  Ser  Gly  Asn  Asn  Ser  Val  Gly  Ala  Ile  Gln  Cys  Pro  Asp
               115                     120                     125

Ser  Gln  Phe  Glu  Cys  Pro  Asp  Phe  Ser  Thr  Cys  Cys  Val  Met  Val  Asp
     130                     135                     140

Gly  Ser  Trp  Gly  Cys  Cys  Pro  Met  Pro  Gln  Ala  Ser  Cys  Cys  Glu  Asp
145                      150                     155                     160

Arg  Val  His  Cys  Cys  Pro  His  Gly  Ala  Phe  Cys  Asp  Leu  Val  His  Thr
               165                     170                     175

Arg  Cys  Ile  Thr  Pro  Thr  Gly  Thr  His  Pro  Leu  Ala  Lys  Lys  Leu  Pro
               180                     185                     190

Ala  Gln  Arg  Thr  Asn  Arg  Ala  Val  Ala  Leu  Ser  Ser  Ser  Val  Met  Cys
               195                     200                     205

Pro  Asp  Ala  Arg  Ser  Arg  Cys  Pro  Asp  Gly  Ser  Thr  Cys  Cys  Glu  Leu
     210                     215                     220

Pro  Ser  Gly  Lys  Tyr  Gly  Cys  Cys  Pro  Met  Pro  Asn  Ala  Thr  Cys  Cys
225                      230                     235                     240

Ser  Asp  His  Leu  His  Cys  Cys  Pro  Gln  Asp  Thr  Val  Cys  Asp  Leu  Ile
               245                     250                     255
```

```
Gln  Ser  Lys  Cys  Leu  Ser  Lys  Glu  Asn  Ala  Thr  Thr  Asp  Leu  Leu  Thr
               260                 265                          270

Lys  Leu  Pro  Ala  His  Thr  Val  Gly  Asp  Val  Lys  Cys  Asp  Met  Glu  Val
          275                      280                          285

Ser  Cys  Pro  Asp  Gly  Tyr  Thr  Cys  Cys  Arg  Leu  Gln  Ser  Gly  Ala  Trp
     290                      295                     300

Gly  Cys  Cys  Pro  Phe  Thr  Gln  Ala  Val  Cys  Cys  Glu  Asp  His  Ile  His
305                      310                     315                          320

Cys  Cys  Pro  Ala  Gly  Phe  Thr  Cys  Asp  Thr  Gln  Lys  Gly  Thr  Cys  Glu
                    325                     330                          335

Gln  Gly  Pro  His  Gln  Val  Pro  Trp  Met  Glu  Lys  Ala  Pro  Ala  His  Leu
               340                      345                     350

Ser  Leu  Pro  Asp  Pro  Gln  Ala  Leu  Lys  Arg  Asp  Val  Pro  Cys  Asp  Asn
               355                 360                     365

Val  Ser  Ser  Cys  Pro  Ser  Ser  Asp  Thr  Cys  Cys  Gln  Leu  Thr  Ser  Gly
     370                      375                     380

Glu  Trp  Gly  Cys  Cys  Pro  Ile  Pro  Glu  Ala  Val  Cys  Cys  Ser  Asp  His
385                      390                     395                          400

Gln  His  Cys  Cys  Pro  Gln  Gly  Tyr  Thr  Cys  Val  Ala  Glu  Gly  Gln  Cys
                    405                     410                          415

Gln  Arg  Gly  Ser  Glu  Ile  Val  Ala  Gly  Leu  Glu  Lys  Met  Pro  Ala  Arg
               420                      425                     430

Arg  Ala  Ser  Leu  Ser  His  Pro  Arg  Asp  Ile  Gly  Cys  Asp  Gln  His  Thr
               435                 440                     445

Ser  Cys  Pro  Val  Gly  Gln  Thr  Cys  Cys  Pro  Ser  Leu  Gly  Gly  Ser  Trp
     450                      455                     460

Ala  Cys  Cys  Gln  Leu  Pro  His  Ala  Val  Cys  Cys  Glu  Asp  Arg  Gln  His
465                      470                     475                          480

Cys  Cys  Pro  Ala  Gly  Tyr  Thr  Cys  Asn  Val  Lys  Ala  Arg  Ser  Cys  Glu
                    485                     490                          495

Lys  Glu  Val  Val  Ser  Ala  Gln  Pro  Ala  Thr  Phe  Leu  Ala  Arg  Ser  Pro
               500                 505                     510

His  Val  Gly  Val  Lys  Asp  Val  Glu  Cys  Gly  Glu  Gly  His  Phe  Cys  His
          515                      520                     525

Asp  Asn  Gln  Thr  Cys  Cys  Arg  Asp  Asn  Arg  Gln  Gly  Trp  Ala  Cys  Cys
     530                      535                     540

Pro  Tyr  Arg  Gln  Gly  Val  Cys  Cys  Ala  Asp  Arg  Arg  His  Cys  Cys  Pro
545                      550                     555                          560

Ala  Gly  Phe  Arg  Cys  Ala  Ala  Arg  Gly  Thr  Lys  Cys  Leu  Arg  Arg  Glu
               565                      570                          575

Ala  Pro  Arg  Trp  Asp  Ala  Pro  Leu  Arg  Asp  Pro  Ala  Leu  Arg  Gln  Leu
               580                 585                     590

Leu
```

( 2 ) INFORMATION FOR SEQ ID NO:5:

( i ) SEQUENCE CHARACTERISTICS:
        ( A ) LENGTH: 1767 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Mus musculus
        ( F ) TISSUE TYPE: Kidney ( i x ) FEATURE:
    ( A ) NAME/KEY: CDS
    ( B ) LOCATION: 1..1767

( x i ) SEQUENCE DESCRIPTION: SEQ ID NO:5:

```
ATG TGG GTC CTG ATG AGC TGG CTG GCC TTC GCG GCA GGG CTG GTA GCC        48
Met Trp Val Leu Met Ser Trp Leu Ala Phe Ala Ala Gly Leu Val Ala
 1               5                  10                  15

GGA ACA CAG TGT CCA GAT GGG CAG TTC TGC CCT GTT GCC TGC TGC CTT        96
Gly Thr Gln Cys Pro Asp Gly Gln Phe Cys Pro Val Ala Cys Cys Leu
             20                  25                  30

GAC CAG GGA GGA GCC AAC TAC AGC TGC TGT AAC CCT CTT CTG GAC ACA       144
Asp Gln Gly Gly Ala Asn Tyr Ser Cys Cys Asn Pro Leu Leu Asp Thr
         35                  40                  45

TGG CCT AGA ATA ACG AGC CAT CAT CTA GAT GGC TCC TGC CAG ACC CAT       192
Trp Pro Arg Ile Thr Ser His His Leu Asp Gly Ser Cys Gln Thr His
     50                  55                  60

GGC CAC TGT CCT GCT GGC TAT TCT TGT CTT CTC ACT GTG TCT GGG ACT       240
Gly His Cys Pro Ala Gly Tyr Ser Cys Leu Leu Thr Val Ser Gly Thr
 65                  70                  75                  80

TCC AGC TGC TGC CCG TTC TCT AAG GGT GTG TCT TGT GGT GAT GGC TAC       288
Ser Ser Cys Cys Pro Phe Ser Lys Gly Val Ser Cys Gly Asp Gly Tyr
                 85                  90                  95

CAC TGC TGC CCC CAG GGC TTC CAC TGT AGT GCA GAT GGG AAA TCC TGC       336
His Cys Cys Pro Gln Gly Phe His Cys Ser Ala Asp Gly Lys Ser Cys
             100                 105                 110

TTC CAG ATG TCA GAT AAC CCC TTG GGT GCT GTC CAG TGT CCT GGG AGC       384
Phe Gln Met Ser Asp Asn Pro Leu Gly Ala Val Gln Cys Pro Gly Ser
         115                 120                 125

CAG TTT GAA TGT CCT GAC TCT GCC ACC TGC TGC ATT ATG GTT GAT GGT       432
Gln Phe Glu Cys Pro Asp Ser Ala Thr Cys Cys Ile Met Val Asp Gly
     130                 135                 140

TCG TGG GGA TGT TGT CCC ATG CCC CAG GCC TCT TGC TGT GAA GAC AGA       480
Ser Trp Gly Cys Cys Pro Met Pro Gln Ala Ser Cys Cys Glu Asp Arg
145                 150                 155                 160

GTG CAT TGC TGT CCC CAT GGG GCC TCC TGT GAC CTG GTT CAC ACA CGA       528
Val His Cys Cys Pro His Gly Ala Ser Cys Asp Leu Val His Thr Arg
                 165                 170                 175

TGC GTT TCA CCC ACG GGC ACC CAC ACC CTA CTA AAG AAG TTC CCT GCA       576
Cys Val Ser Pro Thr Gly Thr His Thr Leu Leu Lys Lys Phe Pro Ala
             180                 185                 190

CAA AAG ACC AAC AGG GCA GTG TCT TTG CCT TTT TCT GTC GTG TGC CCT       624
Gln Lys Thr Asn Arg Ala Val Ser Leu Pro Phe Ser Val Val Cys Pro
         195                 200                 205

GAT GCT AAG ACC CAG TGT CCC GAT GAT TCT ACC TGC TGT GAG CTA CCC       672
Asp Ala Lys Thr Gln Cys Pro Asp Asp Ser Thr Cys Cys Glu Leu Pro
     210                 215                 220

ACT GGG AAG TAT GGC TGC TGT CCA ATG CCC AAT GCC ATC TGC TGT TCC       720
Thr Gly Lys Tyr Gly Cys Cys Pro Met Pro Asn Ala Ile Cys Cys Ser
225                 230                 235                 240

GAC CAC CTG CAC TGC TGC CCC CAG GAC ACT GTA TGT GAC CTG ATC CAG       768
Asp His Leu His Cys Cys Pro Gln Asp Thr Val Cys Asp Leu Ile Gln
                 245                 250                 255

AGT AAG TGC CTA TCC AAG AAC TAC ACC ACG GAT CTC CTG ACC AAG CTG       816
Ser Lys Cys Leu Ser Lys Asn Tyr Thr Thr Asp Leu Leu Thr Lys Leu
             260                 265                 270

CCT GGA TAC CCA GTG AAG GAG GTG AAG TGC GAC ATG GAG GTG AGC TGC       864
Pro Gly Tyr Pro Val Lys Glu Val Lys Cys Asp Met Glu Val Ser Cys
         275                 280                 285

CCT GAA GGA TAT ACC TGC TGC CGC CTC AAC ACT GGG GCC TGG GGC TGC       912
Pro Glu Gly Tyr Thr Cys Cys Arg Leu Asn Thr Gly Ala Trp Gly Cys
```

```
                290                            295                           300
TGT   CCA   TTT   GCC   AAG   GCC   GTG   TGT   TGT   GAG   GAT   CAC   ATT   CAT   TGC   TGC     960
Cys   Pro   Phe   Ala   Lys   Ala   Val   Cys   Cys   Glu   Asp   His   Ile   His   Cys   Cys
305                     310                           315                           320

CCG   GCA   GGG   TTT   CAG   TGT   CAC   ACA   GAG   AAA   GGA   ACC   TGC   GAA   ATG   GGT    1008
Pro   Ala   Gly   Phe   Gln   Cys   His   Thr   Glu   Lys   Gly   Thr   Cys   Glu   Met   Gly
                        325                           330                           335

ATC   CTC   CAA   GTA   CCC   TGG   ATG   AAG   AAG   GTC   ATA   GCC   CCC   CGC   CGC   CTG    1056
Ile   Leu   Gln   Val   Pro   Trp   Met   Lys   Lys   Val   Ile   Ala   Pro   Arg   Arg   Leu
                  340                                 345                           350

CCA   GAC   CCA   CAG   ATC   TTG   AAG   AGT   GAT   ACA   CCT   TGT   GAT   GAC   TTC   ACT    1104
Pro   Asp   Pro   Gln   Ile   Leu   Lys   Ser   Asp   Thr   Pro   Cys   Asp   Asp   Phe   Thr
            355                                 360                     365

AGG   TGT   CCT   ACA   AAC   AAT   ACC   TGC   TGC   AAA   CTC   AAT   TCT   GGG   GAC   TGG    1152
Arg   Cys   Pro   Thr   Asn   Asn   Thr   Cys   Cys   Lys   Leu   Asn   Ser   Gly   Asp   Trp
      370                           375                           380

GGC   TGC   TGT   CCC   ATC   CCA   GAG   GCT   GTC   TGC   TGC   TCA   GAC   AAC   CAG   CAT    1200
Gly   Cys   Cys   Pro   Ile   Pro   Glu   Ala   Val   Cys   Cys   Ser   Asp   Asn   Gln   His
385                           390                           395                     400

TGC   TGC   CCT   CAG   GGC   TTC   ACA   TGT   CTG   GCT   CAG   GGG   TAC   TGT   CAG   AAG    1248
Cys   Cys   Pro   Gln   Gly   Phe   Thr   Cys   Leu   Ala   Gln   Gly   Tyr   Cys   Gln   Lys
                        405                           410                           415

GGA   GAC   ACA   ATG   GTG   GCT   GGC   CTG   GAG   AAG   ATA   CCT   GCC   CGC   CAG   ACA    1296
Gly   Asp   Thr   Met   Val   Ala   Gly   Leu   Glu   Lys   Ile   Pro   Ala   Arg   Gln   Thr
                  420                                 425                           430

ACC   CCG   CTC   CAA   ATT   GGA   GAT   ATC   GGT   TGT   GAC   CAG   CAT   ACC   AGC   TGC    1344
Thr   Pro   Leu   Gln   Ile   Gly   Asp   Ile   Gly   Cys   Asp   Gln   His   Thr   Ser   Cys
            435                           440                           445

CCA   GTA   GGG   CAA   ACC   TGC   TGC   CCA   AGC   CTC   AAG   GGA   AGT   TGG   GCC   TGC    1392
Pro   Val   Gly   Gln   Thr   Cys   Cys   Pro   Ser   Leu   Lys   Gly   Ser   Trp   Ala   Cys
      450                           455                           460

TGC   CAG   CTG   CCC   CAT   GCT   GTG   TGC   TGT   GAG   GAC   CGG   CAG   CAC   TGT   TGC    1440
Cys   Gln   Leu   Pro   His   Ala   Val   Cys   Cys   Glu   Asp   Arg   Gln   His   Cys   Cys
465                           470                           475                     480

CCG   GCC   GGG   TAC   ACC   TGC   AAT   GTG   AAG   GCG   AGG   ACC   TGT   GAG   AAG   GAT    1488
Pro   Ala   Gly   Tyr   Thr   Cys   Asn   Val   Lys   Ala   Arg   Thr   Cys   Glu   Lys   Asp
                        485                           490                           495

GTC   GAT   TTT   ATC   CAG   CCT   CCC   GTG   CTC   CTG   ACC   CTC   GGC   CCT   AAG   GTT    1536
Val   Asp   Phe   Ile   Gln   Pro   Pro   Val   Leu   Leu   Thr   Leu   Gly   Pro   Lys   Val
                  500                                 505                           510

GGG   AAT   GTG   GAG   TGT   GGA   GAA   GGG   CAT   TTC   TGC   CAT   GAT   AAC   CAG   ACC    1584
Gly   Asn   Val   Glu   Cys   Gly   Glu   Gly   His   Phe   Cys   His   Asp   Asn   Gln   Thr
            515                           520                           525

TGT   TGT   AAA   GAC   AGT   GCA   GGA   GTC   TGG   GCC   TGC   TGT   CCC   TAC   CTA   AAG    1632
Cys   Cys   Lys   Asp   Ser   Ala   Gly   Val   Trp   Ala   Cys   Cys   Pro   Tyr   Leu   Lys
      530                           535                           540

GGT   GTC   TGC   TGT   AGA   GAT   GGA   CGT   CAC   TGT   TGC   CCC   GGT   GGC   TTC   CAC    1680
Gly   Val   Cys   Cys   Arg   Asp   Gly   Arg   His   Cys   Cys   Pro   Gly   Gly   Phe   His
545                     550                           555                           560

TGT   TCA   GCC   AGG   GGA   ACC   AAG   TGT   TTG   CGA   AAG   AAG   ATT   CCT   CGC   TGG    1728
Cys   Ser   Ala   Arg   Gly   Thr   Lys   Cys   Leu   Arg   Lys   Lys   Ile   Pro   Arg   Trp
                        565                           570                           575

GAC   ATG   TTT   TTG   AGG   GAT   CCG   GTC   CCA   AGA   CCG   CTA   CTG                      1767
Asp   Met   Phe   Leu   Arg   Asp   Pro   Val   Pro   Arg   Pro   Leu   Leu
                  580                                 585
```

( 2 ) INFORMATION FOR SEQ ID NO:6:

( i ) SEQUENCE CHARACTERISTICS:
        ( A ) LENGTH: 589 amino acids
        ( B ) TYPE: amino acid ( D ) TOPOLOGY: linear ( i i ) MOLECULE TYPE: protein ( x i ) SEQUENCE DESCRIPTION: SEQ ID NO:6:

| Met | Trp | Val | Leu | Met | Ser | Trp | Leu | Ala | Phe | Ala | Ala | Gly | Leu | Val | Ala |
|---|---|---|---|---|---|---|---|---|---|---|---|---|---|---|---|
| 1 | | | | 5 | | | | | 10 | | | | | 15 | |

| Gly | Thr | Gln | Cys | Pro | Asp | Gly | Gln | Phe | Cys | Pro | Val | Ala | Cys | Cys | Leu |
|---|---|---|---|---|---|---|---|---|---|---|---|---|---|---|---|
| | | | 20 | | | | | 25 | | | | | 30 | | |

| Asp | Gln | Gly | Gly | Ala | Asn | Tyr | Ser | Cys | Cys | Asn | Pro | Leu | Leu | Asp | Thr |
|---|---|---|---|---|---|---|---|---|---|---|---|---|---|---|---|
| | | | 35 | | | | 40 | | | | | 45 | | | |

| Trp | Pro | Arg | Ile | Thr | Ser | His | His | Leu | Asp | Gly | Ser | Cys | Gln | Thr | His |
|---|---|---|---|---|---|---|---|---|---|---|---|---|---|---|---|
| | | 50 | | | | | 55 | | | | | 60 | | | |

| Gly | His | Cys | Pro | Ala | Gly | Tyr | Ser | Cys | Leu | Leu | Thr | Val | Ser | Gly | Thr |
|---|---|---|---|---|---|---|---|---|---|---|---|---|---|---|---|
| 65 | | | | | 70 | | | | | 75 | | | | | 80 |

| Ser | Ser | Cys | Cys | Pro | Phe | Ser | Lys | Gly | Val | Ser | Cys | Gly | Asp | Gly | Tyr |
|---|---|---|---|---|---|---|---|---|---|---|---|---|---|---|---|
| | | | | 85 | | | | | 90 | | | | | 95 | |

| His | Cys | Cys | Pro | Gln | Gly | Phe | His | Cys | Ser | Ala | Asp | Gly | Lys | Ser | Cys |
|---|---|---|---|---|---|---|---|---|---|---|---|---|---|---|---|
| | | | 100 | | | | | 105 | | | | | 110 | | |

| Phe | Gln | Met | Ser | Asp | Asn | Pro | Leu | Gly | Ala | Val | Gln | Cys | Pro | Gly | Ser |
|---|---|---|---|---|---|---|---|---|---|---|---|---|---|---|---|
| | | 115 | | | | | 120 | | | | | 125 | | | |

| Gln | Phe | Glu | Cys | Pro | Asp | Ser | Ala | Thr | Cys | Cys | Ile | Met | Val | Asp | Gly |
|---|---|---|---|---|---|---|---|---|---|---|---|---|---|---|---|
| | 130 | | | | | 135 | | | | | 140 | | | | |

| Ser | Trp | Gly | Cys | Cys | Pro | Met | Pro | Gln | Ala | Ser | Cys | Cys | Glu | Asp | Arg |
|---|---|---|---|---|---|---|---|---|---|---|---|---|---|---|---|
| 145 | | | | | 150 | | | | | 155 | | | | | 160 |

| Val | His | Cys | Cys | Pro | His | Gly | Ala | Ser | Cys | Asp | Leu | Val | His | Thr | Arg |
|---|---|---|---|---|---|---|---|---|---|---|---|---|---|---|---|
| | | | | 165 | | | | | 170 | | | | | 175 | |

| Cys | Val | Ser | Pro | Thr | Gly | Thr | His | Thr | Leu | Leu | Lys | Lys | Phe | Pro | Ala |
|---|---|---|---|---|---|---|---|---|---|---|---|---|---|---|---|
| | | | 180 | | | | | 185 | | | | | 190 | | |

| Gln | Lys | Thr | Asn | Arg | Ala | Val | Ser | Leu | Pro | Phe | Ser | Val | Val | Cys | Pro |
|---|---|---|---|---|---|---|---|---|---|---|---|---|---|---|---|
| | | 195 | | | | | 200 | | | | | 205 | | | |

| Asp | Ala | Lys | Thr | Gln | Cys | Pro | Asp | Asp | Ser | Thr | Cys | Cys | Glu | Leu | Pro |
|---|---|---|---|---|---|---|---|---|---|---|---|---|---|---|---|
| | 210 | | | | | 215 | | | | | 220 | | | | |

| Thr | Gly | Lys | Tyr | Gly | Cys | Cys | Pro | Met | Pro | Asn | Ala | Ile | Cys | Cys | Ser |
|---|---|---|---|---|---|---|---|---|---|---|---|---|---|---|---|
| 225 | | | | | 230 | | | | | 235 | | | | | 240 |

| Asp | His | Leu | His | Cys | Cys | Pro | Gln | Asp | Thr | Val | Cys | Asp | Leu | Ile | Gln |
|---|---|---|---|---|---|---|---|---|---|---|---|---|---|---|---|
| | | | | 245 | | | | | 250 | | | | | 255 | |

| Ser | Lys | Cys | Leu | Ser | Lys | Asn | Tyr | Thr | Thr | Asp | Leu | Leu | Thr | Lys | Leu |
|---|---|---|---|---|---|---|---|---|---|---|---|---|---|---|---|
| | | | 260 | | | | | 265 | | | | | 270 | | |

| Pro | Gly | Tyr | Pro | Val | Lys | Glu | Val | Lys | Cys | Asp | Met | Glu | Val | Ser | Cys |
|---|---|---|---|---|---|---|---|---|---|---|---|---|---|---|---|
| | | 275 | | | | | 280 | | | | | 285 | | | |

| Pro | Glu | Gly | Tyr | Thr | Cys | Cys | Arg | Leu | Asn | Thr | Gly | Ala | Trp | Gly | Cys |
|---|---|---|---|---|---|---|---|---|---|---|---|---|---|---|---|
| | 290 | | | | | 295 | | | | | 300 | | | | |

| Cys | Pro | Phe | Ala | Lys | Ala | Val | Cys | Cys | Glu | Asp | His | Ile | His | Cys | Cys |
|---|---|---|---|---|---|---|---|---|---|---|---|---|---|---|---|
| 305 | | | | | 310 | | | | | 315 | | | | | 320 |

| Pro | Ala | Gly | Phe | Gln | Cys | His | Thr | Glu | Lys | Gly | Thr | Cys | Glu | Met | Gly |
|---|---|---|---|---|---|---|---|---|---|---|---|---|---|---|---|
| | | | | 325 | | | | | 330 | | | | | 335 | |

| Ile | Leu | Gln | Val | Pro | Trp | Met | Lys | Lys | Val | Ile | Ala | Pro | Arg | Arg | Leu |
|---|---|---|---|---|---|---|---|---|---|---|---|---|---|---|---|
| | | | 340 | | | | | 345 | | | | | 350 | | |

| Pro | Asp | Pro | Gln | Ile | Leu | Lys | Ser | Asp | Thr | Pro | Cys | Asp | Asp | Phe | Thr |
|---|---|---|---|---|---|---|---|---|---|---|---|---|---|---|---|
| | | 355 | | | | | 360 | | | | | 365 | | | |

| Arg | Cys | Pro | Thr | Asn | Asn | Thr | Cys | Cys | Lys | Leu | Asn | Ser | Gly | Asp | Trp |
|---|---|---|---|---|---|---|---|---|---|---|---|---|---|---|---|
| | 370 | | | | | 375 | | | | | 380 | | | | |

| Gly | Cys | Cys | Pro | Ile | Pro | Glu | Ala | Val | Cys | Cys | Ser | Asp | Asn | Gln | His |
|---|---|---|---|---|---|---|---|---|---|---|---|---|---|---|---|
| 385 | | | | | 390 | | | | | 395 | | | | | 400 |

| | | | | | | | | | | | | | | |
|---|---|---|---|---|---|---|---|---|---|---|---|---|---|---|
|Cys|Cys|Pro|Gln|Gly<br>405|Phe|Thr|Cys|Leu|Ala<br>410|Gln|Gly|Tyr|Cys|Gln<br>415|Lys
|Gly|Asp|Thr|Met<br>420|Val|Ala|Gly|Leu|Glu<br>425|Lys|Ile|Pro|Ala|Arg<br>430|Gln|Thr
|Thr|Pro|Leu<br>435|Gln|Ile|Gly|Asp|Ile<br>440|Gly|Cys|Asp|Gln|His<br>445|Thr|Ser|Cys
|Pro|Val<br>450|Gly|Gln|Thr|Cys|Cys<br>455|Pro|Ser|Leu|Lys|Gly<br>460|Ser|Trp|Ala|Cys
|Cys<br>465|Gln|Leu|Pro|His|Ala<br>470|Val|Cys|Cys|Glu|Asp<br>475|Arg|Gln|His|Cys|Cys<br>480
|Pro|Ala|Gly|Tyr|Thr<br>485|Cys|Asn|Val|Lys|Ala<br>490|Arg|Thr|Cys|Glu|Lys<br>495|Asp
|Val|Asp|Phe|Ile<br>500|Gln|Pro|Pro|Val|Leu<br>505|Leu|Thr|Leu|Gly|Pro<br>510|Lys|Val
|Gly|Asn|Val<br>515|Glu|Cys|Gly|Glu|Gly<br>520|His|Phe|Cys|His|Asp<br>525|Asn|Gln|Thr
|Cys|Cys<br>530|Lys|Asp|Ser|Ala|Gly<br>535|Val|Trp|Ala|Cys|Cys<br>540|Pro|Tyr|Leu|Lys
|Gly<br>545|Val|Cys|Cys|Arg|Asp<br>550|Gly|Arg|His|Cys|Cys<br>555|Pro|Gly|Gly|Phe|His<br>560
|Cys|Ser|Ala|Arg|Gly<br>565|Thr|Lys|Cys|Leu|Arg<br>570|Lys|Lys|Ile|Pro|Arg<br>575|Trp
|Asp|Met|Phe|Leu<br>580|Arg|Asp|Pro|Val|Pro<br>585|Arg|Pro|Leu|Leu| | |

( 2 ) INFORMATION FOR SEQ ID NO:7:

( i ) SEQUENCE CHARACTERISTICS:
        ( A ) LENGTH: 539 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Bos taurus
        ( F ) TISSUE TYPE: Kidney ( i x ) FEATURE:
        ( A ) NAME/KEY: CDS
        ( B ) LOCATION: 1..537

( x i ) SEQUENCE DESCRIPTION: SEQ ID NO:7:

| | | | | | | | | | | | | | | | |
|---|---|---|---|---|---|---|---|---|---|---|---|---|---|---|---|
|AAG|TGG|GGG|TGT|TGC|CCG|ATG|CCC|AAT|GCC|ATT|TGC|TGC|TCC|GAC|CAC|48
|Lys<br>1|Trp|Gly|Cys|Cys<br>5|Pro|Met|Pro|Asn|Ala<br>10|Ile|Cys|Cys|Ser|Asp<br>15|His|
|CTG|CAC|TGC|TGC|CCC|CAG|AAC|ACT|GTG|TGT|GAC|CTG|ACC|CAG|AGT|AAG|96
|Leu|His|Cys|Cys|Pro<br>20|Gln|Asn|Thr|Val|Cys<br>25|Asp|Leu|Thr|Gln|Ser<br>30|Lys|
|TGC|CTC|TCC|AAG|GAG|AAC|GCT|ACG|GAC|CTC|CTC|ACC|AAG|CTG|CCC|GCA|144
|Cys|Leu|Ser<br>35|Lys|Glu|Asn|Ala|Thr<br>40|Asp|Leu|Leu|Thr|Lys<br>45|Leu|Pro|Ala|
|CAC|ACA|GTG|CAG|GAT|GTC|AAG|TGC|GAC|ATG|GAG|GTG|AGC|TGC|CCA|GAC|192
|His|Thr<br>50|Val|Gln|Asp|Val|Lys<br>55|Cys|Asp|Met|Glu|Val<br>60|Ser|Cys|Pro|Asp|
|GAC|TAC|ACC|TGC|TGC|CGC|CTA|CAG|TCC|GGG|GCC|TGG|GGC|TGC|TGC|CCT|240
|Asp|Tyr|Thr|Cys|Cys<br>65|Arg|Leu|Gln|Ser|Gly<br>70|Ala|Trp|Gly|Cys|Cys<br>75|Pro<br>80|
|TTT|GTG|CAG|GCC|GTG|TGC|TGT|GAG|GAC|CAT|GTG|CAC|TGC|TGC|CCG|TCC|288
|Phe|Val|Gln|Ala|Val|Cys|Cys|Glu|Asp|His|Val|His|Cys|Cys|Pro|Ser|

|     |     |     |     |     | 85  |     |     |     |     | 90  |     |     |     |     | 95  |     |     |     |
|-----|-----|-----|-----|-----|-----|-----|-----|-----|-----|-----|-----|-----|-----|-----|-----|-----|-----|-----|
| GGG | TTT | AGG | TGT | GAC | ACA | GAG | AAG | GGT | GTG | TGT | GAG | CAG | GGG | ACC | CGC | 336 |
| Gly | Phe | Arg | Cys | Asp | Thr | Glu | Lys | Gly | Val | Cys | Glu | Gln | Gly | Thr | Arg | |
|     |     |     | 100 |     |     |     | 105 |     |     |     |     | 110 |     |     |     |     |

```
CAG GTG CCG TGG ATG AAG AAA GCC CCA GCC CAC CTC AGC CTG CTG GAC        384
Gln Val Pro Trp Met Lys Lys Ala Pro Ala His Leu Ser Leu Leu Asp
        115             120                 125

CTC GGA GCA GTG GAG GGG GAC GTC CCC TGT GAT AAC GTC ACC AGC TGT        432
Leu Gly Ala Val Glu Gly Asp Val Pro Cys Asp Asn Val Thr Ser Cys
    130             135                 140

CCT TCT TCC ACT ACC TGC TGT CGA CTC AAG TCT GGG GAG TGG GCC TGC        480
Pro Ser Ser Thr Thr Cys Cys Arg Leu Lys Ser Gly Glu Trp Ala Cys
145             150                 155                 160

TGT CCT GCT CCA GAG GCT GTC TGC TGC TCG GAC CAC CAG CAC TGC TGT        528
Cys Pro Ala Pro Glu Ala Val Cys Cys Ser Asp His Gln His Cys Cys
                165                 170                 175

CCC CAA GAT AC                                                          539
Pro Gln Asp
```

(2) INFORMATION FOR SEQ ID NO:8:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO:8:

```
Lys Trp Gly Cys Cys Pro Met Pro Asn Ala Ile Cys Cys Ser Asp His
  1               5                  10                  15

Leu His Cys Cys Pro Gln Asn Thr Val Cys Asp Leu Thr Gln Ser Lys
                20                  25                  30

Cys Leu Ser Lys Glu Asn Ala Thr Asp Leu Leu Thr Lys Leu Pro Ala
            35                  40                  45

His Thr Val Gln Asp Val Lys Cys Asp Met Glu Val Ser Cys Pro Asp
        50                  55                  60

Asp Tyr Thr Cys Cys Arg Leu Gln Ser Gly Ala Trp Gly Cys Cys Pro
 65                     70                  75                  80

Phe Val Gln Ala Val Cys Cys Glu Asp His Val His Cys Cys Pro Ser
                    85                  90                  95

Gly Phe Arg Cys Asp Thr Glu Lys Gly Val Cys Glu Gln Gly Thr Arg
                100                 105                 110

Gln Val Pro Trp Met Lys Lys Ala Pro Ala His Leu Ser Leu Leu Asp
            115                 120                 125

Leu Gly Ala Val Glu Gly Asp Val Pro Cys Asp Asn Val Thr Ser Cys
        130                 135                 140

Pro Ser Ser Thr Thr Cys Cys Arg Leu Lys Ser Gly Glu Trp Ala Cys
145                 150                 155                 160

Cys Pro Ala Pro Glu Ala Val Cys Cys Ser Asp His Gln His Cys Cys
                    165                 170                 175

Pro Gln Asp
```

(2) INFORMATION FOR SEQ ID NO:9:

(i) SEQUENCE CHARACTERISTICS:
        (A) LENGTH: 341 base pairs
        (B) TYPE: nucleic acid
        (C) STRANDEDNESS: single
        (D) TOPOLOGY: linear ( i i ) MOLECULE TYPE: cDNA ( v i ) ORIGINAL SOURCE:
  ( A ) ORGANISM: Gallus domesticus
  ( F ) TISSUE TYPE: Kidney ( i x ) FEATURE:
  ( A ) NAME/KEY: CDS
  ( B ) LOCATION: 1..339

( x i ) SEQUENCE DESCRIPTION: SEQ ID NO:9:

| | | | | | | | | | | | | | | | | |
|---|---|---|---|---|---|---|---|---|---|---|---|---|---|---|---|---|
| AAG | TGG | GGT | TGT | TGC | CCC | ATG | CCG | AGA | GGC | GTG | TGC | TGC | CGG | GAT | GAG | 48 |
| Lys | Trp | Gly | Cys | Cys | Pro | Met | Pro | Arg | Gly | Val | Cys | Cys | Arg | Asp | Glu | |
| 1 | | | | 5 | | | | | 10 | | | | | 15 | | |
| GAG | CAC | TGC | TGT | CCC | CAC | TCC | ACC | AGC | TGT | GAT | TTG | GAG | CGC | GGG | CGC | 96 |
| Glu | His | Cys | Cys | Pro | His | Ser | Thr | Ser | Cys | Asp | Leu | Glu | Arg | Gly | Arg | |
| | | | 20 | | | | | 25 | | | | | 30 | | | |
| TGT | GTG | TCC | CCT | ACG | GGG | GAC | GTC | CCC | ATG | GCC | ACC | AAA | TTC | CCG | GCC | 144 |
| Cys | Val | Ser | Pro | Thr | Gly | Asp | Val | Pro | Met | Ala | Thr | Lys | Phe | Pro | Ala | |
| | | 35 | | | | | 40 | | | | | 45 | | | | |
| TGG | AAG | AGA | CCG | CGC | GGT | GCT | GCG | GCA | CAG | CCC | CGG | CTC | CGC | GTC | CCA | 192 |
| Trp | Lys | Arg | Pro | Arg | Gly | Ala | Ala | Ala | Gln | Pro | Arg | Leu | Arg | Val | Pro | |
| | 50 | | | | | 55 | | | | | 60 | | | | | |
| GCA | GTG | GTT | GGT | GAC | GTG | AAG | TGT | GAC | GAT | GAG | ATG | AGC | TGT | CCC | GAC | 240 |
| Ala | Val | Val | Gly | Asp | Val | Lys | Cys | Asp | Asp | Glu | Met | Ser | Cys | Pro | Asp | |
| 65 | | | | | 70 | | | | | 75 | | | | | 80 | |
| GGG | AAC | ACG | TGC | TGC | AGG | CTG | AGC | TCC | GGG | CAG | TGG | GGG | TGC | TGC | CCG | 288 |
| Gly | Asn | Thr | Cys | Cys | Arg | Leu | Ser | Ser | Gly | Gln | Trp | Gly | Cys | Cys | Pro | |
| | | | | 85 | | | | | 90 | | | | | 95 | | |
| CTG | GAG | CAG | GCC | GTG | TGC | TGC | CCC | GAC | CAC | ATC | CAC | TGC | TGC | CCC | CAA | 336 |
| Leu | Glu | Gln | Ala | Val | Cys | Cys | Pro | Asp | His | Ile | His | Cys | Cys | Pro | Gln | |
| | | | 100 | | | | | 105 | | | | | 110 | | | |
| GAT | AC | | | | | | | | | | | | | | | 341 |
| Asp | | | | | | | | | | | | | | | | |

( 2 ) INFORMATION FOR SEQ ID NO:10:

( i ) SEQUENCE CHARACTERISTICS:
  ( A ) LENGTH: 113 amino acids
  ( B ) TYPE: amino acid
  ( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Lys | Trp | Gly | Cys | Cys | Pro | Met | Pro | Arg | Gly | Val | Cys | Cys | Arg | Asp | Glu |
| 1 | | | | 5 | | | | | 10 | | | | | 15 | |
| Glu | His | Cys | Cys | Pro | His | Ser | Thr | Ser | Cys | Asp | Leu | Glu | Arg | Gly | Arg |
| | | | 20 | | | | | 25 | | | | | 30 | | |
| Cys | Val | Ser | Pro | Thr | Gly | Asp | Val | Pro | Met | Ala | Thr | Lys | Phe | Pro | Ala |
| | | 35 | | | | | 40 | | | | | 45 | | | |
| Trp | Lys | Arg | Pro | Arg | Gly | Ala | Ala | Ala | Gln | Pro | Arg | Leu | Arg | Val | Pro |
| | 50 | | | | | 55 | | | | | 60 | | | | |
| Ala | Val | Val | Gly | Asp | Val | Lys | Cys | Asp | Asp | Glu | Met | Ser | Cys | Pro | Asp |
| 65 | | | | | 70 | | | | | 75 | | | | | 80 |

```
Gly Asn Thr Cys Cys Arg Leu Ser Ser Gly Gln Trp Gly Cys Cys Pro
                85                  90                  95

Leu Glu Gln Ala Val Cys Cys Pro Asp His Ile His Cys Cys Pro Gln
            100             105             110

Asp
```

( 2 ) INFORMATION FOR SEQ ID NO:11:

( i ) SEQUENCE CHARACTERISTICS:
        ( A ) LENGTH: 110 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Cercopithecus aethiops
        ( H ) CELL LINE: BSC-1

( i x ) FEATURE:
        ( A ) NAME/KEY: CDS
        ( B ) LOCATION: 28..108

( x i ) SEQUENCE DESCRIPTION: SEQ ID NO:11:

```
AGCTTCTGCA GGGGCGGGGC CTCCCCC ATG CCG CCC TCC GGG CTG CGG CTG          51
                              Met Pro Pro Ser Gly Leu Arg Leu
                               1               5

CTG CCG CTG CTG CTA CCG CTG CTG TGG CTA CTG GTG CTG ACG CCT AGC        99
Leu Pro Leu Leu Leu Pro Leu Leu Trp Leu Leu Val Leu Thr Pro Ser
     10              15                  20

CGG CCG GCC GC                                                         110
Arg Pro Ala
 25
```

( 2 ) INFORMATION FOR SEQ ID NO:12:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Pro Pro Ser Gly Leu Arg Leu Leu Pro Leu Leu Leu Pro Leu Leu
 1               5               10                  15

Trp Leu Leu Val Leu Thr Pro Ser Arg Pro Ala
             20                  25
```